United States Patent
Kapeller-Libermann et al.

(10) Patent No.: US 7,410,785 B2
(45) Date of Patent: Aug. 12, 2008

(54) ACTR-1, A NOVEL HUMAN ACYLTRANSFERASE AND USES THEREOF

(75) Inventors: Rosana Kapeller-Libermann, Chestnut Hill, MA (US); Thomas Joseph Logan, Springfield, PA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/325,013

(22) Filed: Jan. 4, 2006

(65) Prior Publication Data

US 2006/0121518 A1    Jun. 8, 2006

Related U.S. Application Data

(62) Division of application No. 09/935,290, filed on Aug. 21, 2001, now Pat. No. 7,052,858.

(60) Provisional application No. 60/226,509, filed on Aug. 21, 2000.

(51) Int. Cl.
  *C12N 9/10*   (2006.01)
  *C07K 1/00*   (2006.01)

(52) U.S. Cl. .................... 435/193; 530/350

(58) Field of Classification Search .......... 435/190; 530/350
  See application file for complete search history.

(56) References Cited

U.S. PATENT DOCUMENTS 5,888,793 A    3/1999    Hillman et al.
2003/0165831 A1 *  9/2003   Lee et al.

FOREIGN PATENT DOCUMENTS

| WO | WO 01/60860 | * | 8/2001 |
| WO | WO 01/73051 A2 | | 10/2001 |
| WO | WO 02/00857 A2 | | 1/2002 |
| WO | WO 02/00857 A3 | | 1/2002 |
| WO | WO 02/26950 A2 | | 4/2002 |
| WO | WO 02/40666 A2 | | 5/2002 |

OTHER PUBLICATIONS

Hegde et al. Database: EST, Accession No. AW976326.*
Shin et al. "transcriptional regulation of p90 with sequence homology to *Escherichia coli* glycerol-3-phophate acyltransferase" J. Biol. Chem. 266 (35), 23834-23839 (1991).*
Bhat et al. "Rat sy-glycerol-3-phosphate acyltransferase: molecular cloning and characterization of the CDNA and expressed protein" Biochim. Biophys. Acta 1439, 415-423 (1999).*
Wilkison, W. O. and Bell, R. M., Biochim. Biophys. Acta 1348:3-9 (1997).
Dircks, L. and Sul H. S., Prog. Lipid Res. 38:461-479 (1999).
Dircks, L. et al., J. Biol. Chem. 274(49):34728-34734 (1999).
Yet, S-F. et al., Biochemistry 32:9486-9491 (1993).
Yet, S-F. et al., Biochemistry 34:7303-7310 (1995).
Yamashita, A. et al., J. Biochem. 122:1-16 (1997).
Lewin, T. M. et al., Biochemistry 38:5764-5771 (1999).
Heath, R. and Rock, C. O., J. Bacteriol. 181(6):1944-1946 (1999).
Schlossman, D. M., and Bell, R. M., J. Biol. Chem. 251(18):5738-5744 (1976).
Bhat, B. G., et al., Biochim. Biophys. Acta 1439:415-423 (1999).
Zhang, Y. et al., Nature 372:425-432 (1994).
Garg A., Grundy S. M., Ann Intern Med 121:416-422 (1994).
Kuroki S. et al., Lipids 34(8):817-823 (1999).
Elmore, M.A., "Mammalian Lyso Phosphatidic Acid Acyl Transferases." Research Disclosure, Kenneth Mason Publications, Hampshire, GB, No. 400 (Aug. 1, 1997) pp. 551-553 (XP000726660) ISSN: 0374-4353).

* cited by examiner

*Primary Examiner*—Maryam Monshipouri

(57) ABSTRACT

The invention provides isolated nucleic acid molecules, designated ACTR-1 nucleic acid molecules, which encode novel acyltransferase family members. The invention also provides antisense nucleic acid molecules, recombinant expression vectors containing ACTR-1 nucleic acid molecules, host cells into which the expression vectors have been introduced, and nonhuman transgenic animals in which an ACTR-1 gene has been introduced or disrupted. The invention still further provides isolated ACTR-1 proteins, fusion proteins, antigenic peptides and anti-ACTR-1 antibodies. Diagnostic methods utilizing compositions of the invention are also provided.

8 Claims, 32 Drawing Sheets

FIG. 1A

```
Input file Fbh56919FL2.seq
Sequence length 3003

TTCGGCACCAGGCTGCTGCGGGGGACTCTTTCTGAGGTTACTGTGGAGCACCCAAAGTCTGTCAGCCTCTGCCGTGC

AAACAGGCACCCAGAGGAACCAGACCTTGCTTATTCACCCACAGCCTGGACTGTCTCTTCCAGAGTCTCCATCAGCTT

TGCTAATCGACTGATTGGAAATAATTCCTCAAACACCACCAAGTCAAGGATACAGGCAGCAGCGGCTCCCCTGTTGTAT

GGACATTCTGCACCCGAAACTGATAGCTGAGTCCTGAAGTTTTATGTTATGAAACAGAAGAACTTTCATCCCAGCACAT
```

|   |   |   |   |   |   |   |   |   |   |   |   |   |   |
|---|---|---|---|---|---|---|---|---|---|---|---|---|---|
|   |   |   | M | D | E | S | A | L | T | L | G | T | I | D | V | 13 |
| GATTTGGGAATTACACTTTGTGAC ATG GAT GAA TCT GCA CTG ACC CTT GGT ACA ATA GAT GTT | 39 |

| S | Y | L | P | H | S | S | E | Y | S | V | G | R | C | K | H | T | S | E | E | 33 |
| TCT TAT CTG CCA CAT TCA TCA GAA TAC AGT GTT GGT CGA TGT AAG CAC AGT GAG GAA | 99 |

| W | G | E | C | G | F | R | P | T | V | F | S | A | T | L | K | W | K | E | 53 |
| TGG GGT GAG TGT GGC TTT AGA CCC ACC GTC TTC GCA TCT ACT TTA AAA TGG AAA GAA | 159 |

| S | L | M | S | R | K | R | P | F | V | G | R | C | C | Y | S | C | T | P | Q | 73 |
| AGC CTA ATG AGT CGG AAA AGG CCA TTT GTT GGA AGA TGT TGT TAC TCC TGC ACT CCC CAG | 219 |

| S | W | D | K | F | F | N | P | S | I | P | S | L | G | R | L | R | N | V | I | Y | 93 |
| AGC TGG GAC AAA TTT TTC AAC CCC AGT ATC CCG TCT TTG GGT TTG CGG AAT GTT ATT TAT | 279 |

| I | N | E | T | H | T | R | H | T | R | W | L | A | R | R | L | S | Y | V | L | 113 |
| ATC AAT GAA ACT CAC ACA AGA AGA CAC TGG CTT GCA AGA CGC CTT TCT TAC GTT CTT | 339 |

| F | I | Q | E | R | D | V | H | K | G | M | F | A | T | N | V | T | E | N | V | 133 |
| TTT ATT CAA GAG CGA GAT GTG CAT AAG GGC ATG TTT GCC ACC AAT GTG ACT GAA AAT GTG | 399 |

FIG. 1B

```
  L   N   S   S   R   V   Q   E   A   I   A   E   V   A   A   E   L   N   P   D    153
CTG AAC AGC AGT AGA GTA CAA GAG GCA ATT GCA GAA GTG GCT GCT GAA TTA AAC CCT GAT    459

G   S   A   Q   Q   Q   S   K   A   V   N   K   V   K   K   A   K   R   I        173
GGT TCT GCC CAG CAG CAA TCA AAA GCC GTT AAC AAA GTG AAG AAA GCT AAA AGG ATT        519

L   Q   E   M   V   A   T   V   S   P   A   M   I   R   L   T   G   W   V   L    193
CTT CAA GAA ATG GTT GCC ACT GTC TCA CCG GCA ATG ATC AGA CTG ACT GGG TGG GTG CTG    579

L   K   F   N   S   F   W   N   I   Q   I   H   G   Q   L   E   M                213
CTA AAA CTG TTC AAC AGC TTC TGG AAC ATT CAA CAC GGT CAA CTT GAG ATG                639

V   K   A   A   T   E   T   L   F   L   P   V   H   R   S   H                    233
GTT AAA GCT GCA ACT GAG ACG ACG CTA CTG CCA GTT CAT AGA TCC CAT                    699

I   D   Y   L   L   T   T   I   F   C   H   N   I   K   A   P   Y   I            253
ATT GAC TAT CTG CTC ACT TTC TGC CAT AAC ATC AAA GCA CCA TAC ATT                    759

A   S   G   N   N   L   N   I   P   I   F   S   T   L   H   K   L   G   G        273
GCT TCA GGC AAT AAT CTC AAC ATC CCA ATC TTC AGT ACC TTG CAT AAG CTT GGG GGC        819

F   F   I   R   R   R   H   D   V   E   L   P   D   R   K   Q   Q   L   Y   R    293
TTC TTC ATA CGA AGG CGA CAT GAT GTT GAA CTC CCA GAT CGG AAA CAG CAG GTT CTC TAT AGA 879

A   L   H   G   I   V   E   L   R   Q   Q   F   L   E   I   F                    313
GCT TTG CTC CAT GGG CAT ATA GTT GAA CTT CGA CAA CAG TTC TTG GAG ATC TTC            939

L   E   T   R   S   R   S   G   K   T   S   C   A   R   A   G   L   S            333
CTG GAA ACA CGT TCT AGG AGT GGA AAA ACC TCT TGT GCT CGG GCA GGA CTT TCA            999
```

FIG. 1C

```
  V   V   D   T   L   S   T   N   V   I   P   D   I   L   I   P   V   G              353
GTT GTG GTA GAT ACT CTG TCT ACC AAT GTC ATC CCA GAC ATC TTG ATA CCT GTT GGA          1059

I   S   Y   D   R   I   E   G   H   Y   N   G   E   Q   L   K   P   K              373
ATC TCC TAT GAT CGC ATT ATC GAA CAC TAC AAT GGT GAA CAA CTG AAA CCT AAG              1119

K   N   E   S   L   W   S   V   A   R   G   V   I   R   M   L   R   K   N   Y      393
AAG AAT GAG AGC CTG TGG AGT GTA GCA AGA GGT GTT ATT AGA ATG TTA CGA AAA AAC TAT      1179

G   C   V   R   V   D   F   A   Q   P   F   S   L   E   Y   L   K   E   S   Q      413
GGT TGT GTC CGA GTG GAT TTT GCA CAG CCA TTT TCC TTA GAA TAT TTA AAG GAA AGC CAA      1239

S   Q   K   P   V   S   D   A   A   L   L   L   E   Q   A   L   P   A   I   L      433
AGT CAG AAA CCG GTG TCT GCT GAT GCT CTT CTC GAG CAA GCG TTG TTA CCA GCT ATA CTT      1299

P   S   R   P   S   D   E   G   R   D   T   S   I   N   E   S   R              453
CCT TCA AGA CCC AGT GAT GAA GGT AGA GAC ACG TCC ATT AAT GAG TCC AGA                  1359

N   A   T   D   E   S   K   S   L   R   R   L   I   A   N   L   A   E   H   I   L  473
AAT GCA ACA GAT GAA TCC AAG AGC CTA CGA AGG TTG ATT GCA AAT CTG GCT GAG CAT ATT CTA  1419

F   T   A   S   K   S   C   A   I   M   S   T   L   V   E   D   F   V   M   K   L  493
TTC ACT GCT AGC AAG TCC TGT GCC ATT ATG TCC ACA TTG GTC GAA GAC TTC TTT GTG ATG AAA CTC  1479

Y   R   H   Q   G   I   D   L   S   T   L   V   E   D   F   V   M   K   L          513
TAC AGA CAC AGG CAG GGA ATT GAT CTC TCC ACA TTG GTC GAA GAC TTC TTT GTG ATG AAA CTC  1539

E   E   V   L   A   R   D   F   D   L   G   F   S   G   N   S   E   D   V          533
GAG GAA GTC CTG GCT CGT GAT TTT GAC CTG GGG TTC TCA GGA AAT TCA GAA GAT GTA GTA      1599
```

FIG. 1D

| | | | | | | | | | | | | | | | | | | | | |
|---|---|---|---|---|---|---|---|---|---|---|---|---|---|---|---|---|---|---|---|---|
| M | H | A | I | Q | L | L | G | N | C | V | T | I | T | H | T | S | R | N | D | 553 |
| ATG | CAT | GCC | ATA | CAG | CTG | CTG | GGA | AAT | TGT | GTC | ACA | ATC | ACC | CAC | ACT | AGC | AGG | AAC | GAT | 1659 |
| E | F | F | I | T | P | S | T | T | V | P | S | V | F | E | L | N | F | Y | S | 573 |
| GAG | TTT | TTT | ATC | ACC | CCC | AGC | ACA | ACT | GTC | CCA | TCA | GTC | TTC | GAA | CTC | AAC | TTC | TAC | AGC | 1719 |
| N | G | V | L | H | V | F | M | I | A | I | C | S | L | Y | A | V | 593 |
| AAT | GGG | GTA | CTT | CAT | GTC | TTT | ATG | ATC | GCC | ATA | TGC | AGC | CTT | TAT | GCA | GTT | 1779 |
| L | N | K | R | G | L | R | K | A | A | S | P | N | L | I | S | Q | E | 613 |
| CTG | AAC | AAG | AGG | GGA | CTG | AGG | AAG | GCG | GCC | AGC | CCT | AAC | CTG | ATC | AGC | CAG | GAG | 1839 |
| Q | L | V | R | K | T | F | Y | C | Y | L | S | N | E | T | I | S | 633 |
| CAG | CTG | GTG | CGG | AAG | ACA | TTT | TAC | TGC | TAC | CTC | TCC | AAT | GAA | GGC | ACC | ATC | TCA | 1899 |
| L | P | C | Q | T | V | Q | V | C | H | E | T | G | K | F | I | Q | Y | 653 |
| CTG | CCT | TGC | CAG | ACA | GTC | CAA | GTC | TGC | CAT | GAA | ACA | GGA | AAG | TTT | ATC | CAG | TAT | 1959 |
| G | I | L | T | V | A | E | H | D | Q | E | P | L | S | P | S | L | A | E | 673 |
| GGC | ATT | CTT | ACA | GTG | GCA | GAG | CAC | GAC | CAG | GAA | CCT | TTG | TCT | CCT | AGT | CTT | GCT | GAG | 2019 |
| Q | Q | W | D | K | E | E | L | P | R | D | W | R | S | D | E | E | D | E | 693 |
| CAG | CAG | TGG | GAC | AAG | GAG | GAA | CTT | CCA | AGA | GAT | TGG | TCT | AGA | AGT | GAT | GAA | GAA | GAA | 2079 |
| D | S | F | G | E | E | Q | R | D | C | Y | L | K | V | S | Q | S | K | E | 713 |
| GAT | AGT | TTT | GGG | GAG | GAA | CAG | CGA | GAT | TGC | TAC | CTG | AAG | GTG | AGC | CAA | TCC | AAG | GAG | 2139 |
| H | Q | F | I | T | F | L | Q | R | L | G | P | L | L | E | A | Y | S | 733 |
| CAC | CAG | CAG | TTT | ATC | ACC | TTC | TTA | CAG | AGA | CTC | CTT | GGG | CCT | TTG | CTG | GAG | GCC | TAC | AGC | 2199 |

FIG. 1E

```
  S   A   A   I   F   V   H   N   F   S   G   P   V   P   E   P   E   Y   L   Q       753
TCT GCT GCC ATC TTT GTT CAC AAC TTC AGT GGT CCT GTT CCA GAA CCT GAG TAT CTG CAA      2259

K   L   H   K   Y   L   I   T   R   T   E   R   N   V   A   V   Y   A   E   S       773
AAG TTG CAC AAA TAC CTA ATA ACC AGA ACA GAA AAT GTT GCA GTA TAT GCT GAG AGT          2319

A   T   Y   C   L   V   K   N   A   V   K   M   F   K   D   I   G   V   F   K       793
GCC ACA TAT TGT CTT GTG AAG AAT GCT GTG AAA ATG TTT AAG GAT ATT GGG GTT TTC AAG      2379

E   T   K   Q   K   R   V   S   V   L   E   L   S   T   F   L   P   Q   C           813
GAG ACC AAA CAA AAG AGA GTG TCT GTT TTA GAA CTG AGC AGC ACT TTT CTA CCT CAA TGC      2439

N   R   Q   K   L   L   E   Y   I   L   S   F   V   V   L   *                       829
AAC CGA CAA AAA CTT CTA GAA TAT ATT CTG AGT TTT GTG GTG CTG TAG                      2487
```

GTAACGTGTGTGGCACTGCTGTGGCAAATGAAGGTCATGAGATGAGTTCCTTGTAGGTACCAGCTTCTGGCTCAAGAGTTTGA

AGGTGCCTTCGCAGGGGTCAGGCCTGCCCTGTNCCGAAGTGATCTCCTGGAAGACAAGTGCCTTCTNCCTCCATGGATC

TGAGATCTTCCCAGCTTT

FIG. 3A

Protein Family / Domain Matches, HMMer version 2

```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).

HMM file:       /prod/ddm/seqanal/PFAM/pfam6.4/Pfam
Sequence file:  /prod/ddm/wspace/orfanal/oa-script.21255.seq Query:  56919

Scores for sequence family classification (score includes all domains):
Model             Description                                      Score    E-value   N
-----             -----------                                      -----    -------  ---
Acyltransferase   Acyltransferase                                  126.1    6.4e-34   1

Parsed for domains:
Model            Domain  seq-f  seq-t    hmm-f hmm-t        score    E-value
-----            ------  -----  -----    ----- -----        -----    -------
Acyltransferase   1/1     215    412 ..     1   195 []      126.1    6.4e-34
```

FIG. 3B

```
Alignments of top-scoring domains:
Acyltransferase: domain 1 of 1, from 215 to 412: score 126.1, E = 6.4e-34
                *->lenlpkkgpaivvsNHrSylDilvlsaalprrgpwlvrrlvfiakke
                   +  ++++ p  ++ + HrS++D+l+l  ++l++++       ++   +ia ++
      56919  215    KAATETNLPLLFLPVHRSHIDYLLLTFILFCHN----IKAPYIASGN   257 llkvPllfGwlmrlagaifidRnnra.....kdalaaadelvrvlellrk
                   +l++P+ f++l+ ++g +fi+R+ +++++++kd l++a+ + + +elir+
      56919  258    NLNIPI-FSTLIHKLGGFFIRRRLDEtpdgrKDVLYRALLHGHIVELLRQ   306 grsvliFPEGTRsrsgellppfKkGia.....afrlAlkagvpivPvviv
                   +  + iF EGTRsrsg++ +    ++G+++      + ++    i+Pv+i
      56919  307    QQFLEIFLEGTRSRSGKTSC-ARAGLLsvvvdTLSTNVIPDILIIPVGI-   354 sgteelepkneagkllLrlarkkgpvtvrvlppipld..pedikelaerlr
                   s++   ++e ++++ +      +++kk+++++ v +++   ++++ +++++ +
      56919  355    SYDRIIEGHYNGEQ--LGKPKKNESLWSVARGVIRMlrKNYGCVRVDFAQ   402 dilvqaleel<-*
                   +    ++++ e+
      56919  403    PFSLKEYLES     412
```

FIG. 4A

ProDom Matches

| ProdomId | Start | End | Description |
|---|---|---|---|
| View Prodom PD347660 | 1 | 55 | p2001.1 (2) PLSB(2) // ACYLTRANSFERASE PHOSPHOLIPID BIOSYNTHESIS PRECURSOR TRANSMEMBRANE GLYCEROL-3-PHOSPHATE GPAT MITOCHONDRION MITOCHONDRIAL |
| View Prodom PD087501 | 51 | 158 | p2001.1 (1) // AIP2-DLD1 |
| View Prodom PD353751 | 56 | 152 | p2001.1 (2) PLSB(2) // ACYLTRANSFERASE PHOSPHOLIPID BIOSYNTHESIS PRECURSOR TRANSMEMBRANE GLYCEROL-3-PHOSPHATE GPAT MITOCHONDRION MITOCHONDRIAL |
| View Prodom PD037846 | 128 | 259 | p2001.1 (15) PLSB(5) DAPT(2) // ACYLTRANSFERASE GLYCEROL-3-PHOSPHATE PHOSPHOLIPID GPAT BIOSYNTHESIS MITOCHONDRIAL TRANSMEMBRANE PRECURSOR MITOCHONDRION |
| View Prodom PD042466 | 259 | 590 | p2001.1 (16) PLSB(4) DAPT(2) // ACYLTRANSFERASE GLYCEROL-3-PHOSPHATE BIOSYNTHESIS PHOSPHOLIPID GPAT PRECURSOR MITOCHONDRIAL TRANSMEMBRANE MITOCHONDRION |
| View Prodom PD025192 | 462 | 649 | p2001.1 (4) PLSB(3) // ACYLTRANSFERASE PHOSPHOLIPID MITOCHONDRIAL BIOSYNTHESIS PRECURSOR TRANSMEMBRANE GLYCEROL-3-PHOSPHATE GPAT MITOCHONDRION |

FIG. 4B

```
View Prodom PD042027    465  673    p2001.1 (6) PLSB(2) // ACYLTRANSFERASE      458
                                    GLYCEROL-3-PHOSPHATE MEMBRANE
                                    PHOSPHOLIPID GPAT BIOSYNTHESIS MUTANT View Prodom PD042760    650  828    p2001.1 (2) PLSB(2) // ACYLTRANSFERASE       80
                                    PHOSPHOLIPID BIOSYNTHESIS PRECURSOR
                                    TRANSMEMBRANE GLYCEROL-3-PHOSPHATE
                                    GPAT MITOCHONDRION MITOCHONDRIAL View Prodom PD042760                                                            799

>PD042760 p2001.1 (2) PLSB(2) // ACYLTRANSFERASE PHOSPHOLIPID BIOSYNTHESIS
         PRECURSOR TRANSMEMBRANE GLYCEROL-3-PHOSPHATE GPAT MITOCHONDRION
         MITOCHONDRIAL
         Length = 179

Score = 799 (286.3 bits), Expect = 1.2e-79, P = 1.2e-79
 Identities = 155/179 (86%), Positives = 161/179 (89%)

Query:   650  FIQYGILTVAEHDDQEDISPSLAEQQWDKKLPEPLSWRXXXXXXXXXXXQRDCYLKVS    709
              FIQYGILTVAE DDQED+SP LAEQQW+KKLPEPL+WR          QRDCYLKVS
Sbjct:     1  FIQYGILTVAEQDDQEDVSPGLAEQQWNKKLPEPLNWRSDEEDEDSDFGEEQRDCYLKVS   60

Query:   710  QSKEHQQFITFLQRLLGPLLEAYSSAAIFVHNFSGPVPEPEYLQKLHKYLITRTERNVAV  769
              Q+KEHQQFITFLQRLLGPLLEAYSSAAIFVHNF GPVPE EYLQKLH+YLITRTERNVAV
Sbjct:    61  QAKEHQQFITFLQRLLGPLLEAYSSAAIFVHNFRGPVPESEYLQKLHRYLITRTERNVAV  120

Query:   770  YAESATYCLVKNAVKMFKDIGVFKETKQKRVSVLELSSTFLPQCNRQKLLEYILSFVVL   828
              YAESATYCLVKNAVKMFKDIGVFKETKQKR SVLELS+TFLPQCNRQKLLEYILSFVVL
Sbjct:   121  YAESATYCLVKNAVKMFKDIGVFKETKQKRASVLELSTTFLPQCNRQKLLEYILSFVVL   179
```

FIG. 4C

View Prodom PD353751

>PD353751 p2001.1 (2) PLSB(2) // ACYLTRANSFERASE PHOSPHOLIPID BIOSYNTHESIS
    PRECURSOR TRANSMEMBRANE GLYCEROL-3-PHOSPHATE GPAT MITOCHONDRION
    MITOCHONDRIAL
    Length = 97

Score = 500 (181.1 bits), Expect = 2.1e-47, P = 2.1e-47
Identities = 90/97 (92%), Positives = 97/97 (100%)

Query:   56  MSRKRPFVGRCCYSCTPQSWDKFFNPSIPSLGLRNVIYINETHTRHRGWLARRLSYVLFI  115
             MSRKRPFVGRCCYSCTPQSW++FFNPSIPSLGLRNVIYINETHTRHRGWLARRLSY+LF+
Sbjct:   1   MSRKRPFVGRCCYSCTPQSWERFFNPSIPSLGLRNVIYINETHTRHRGWLARRLSYILFV   60

Query:  116  QERDVHKGMFATNVTENVLNSSRVQEAIAEVAAELNP  152
             QERDVHKGMFAT++T+NVLNSSRVQEAIAEVAAELNP
Sbjct:   61  QERDVHKGMFATSITDNVLNSSRVQEAIAEVAAELNP   97

View Prodom PD025192

>PD025192 p2001.1 (4) PLSB(3) // ACYLTRANSFERASE PHOSPHOLIPID MITOCHONDRIAL
    BIOSYNTHESIS PRECURSOR TRANSMEMBRANE GLYCEROL-3-PHOSPHATE GPAT
    MITOCHONDRION
    Length = 194

Score = 458 (166.3 bits), Expect = 8.7e-43, P = 8.7e-43
Identities = 95/192 (49%), Positives = 126/192 (65%)

Query:  462  RRLIANLAEHILFTASKSCAIMSTHIVACLLLYRHRQGIDLSTLVEDFFVMKEEVLARDF  521
             R LI ++ EH++F  S    C+IMSTH+VACLLL R R G+    STL ED    + E++LA
Sbjct:   3   RNLIRSIGEHVVFDCSMMCSIMSTHVVACLLLTRWRNGVHRSTLEEDCDWLCEKILAEGG   62

FIG. 4D

```
Query:  522 DL-GFSGNS---EDVVMHAIQLLGNCVTITHTSRNDEFFITPSTTVPSVFELNFYSNGVL 577
            D+ GFSG S      +V +A +LLG+CVT+T  RNDEF+I+P +VPS EL +YSN V+
Sbjct:   63 DIVGFSGKSTKGSQIVKYACELLGSCVTVTDEDRNDEFYISPKNSVPSFIELAYYSNSVI 122

Query:  578 HVFIMEAIIACSLYAVLNKRGLGGPTSTPPNLISQEQLVRKAASLCYLLSNEGTISLPCQ 637
            F +++IIAC++Y++ NK   GG    NLISQEQLV  A SLC L E    PCQ
Sbjct:  123 CHFALKSIIACTIYSLPNKTKNGGEAGGLGNLISQEQLVEDALSLCDWLQYEFMFCRPCQ 182

Query:  638 TFYQVCHETVGK 649
            T ++CH T+GK
Sbjct:  183 TLRELCHNTLGK 194
```

View Prodom PD042466

>PD042466 p2001.1 (16) PLSB(4) DAPT(2) // ACYLTRANSFERASE GLYCEROL-3-PHOSPHATE BIOSYNTHESIS PHOSPHOLIPID GPAT PRECURSOR MITOCHONDRIAL TRANSMEMBRANE MITOCHONDRION
Length = 299

Score = 413 (150.4 bits), Expect = 4.7e-42, Sum P(2) = 4.7e-42
Identities = 79/152 (51%), Positives = 108/152 (71%)

```
Query:  259 LNIPIFSTLIHKLGGFFIRRRLDETPDGRKDVLYRALLHGHIVELLRQQQFLEIFLEGTR 318
            L++PI  +L+ + G FFIRR  D TP+G+ D LYRA+ H ++ +L+  +   +E F+EGTR
Sbjct:    2 LSMPIMGSLLRRTGAFFIRRSFDPTPEGKGDQLYRAVFHEYVAQLISKGYNIEFFIEGTR 61

Query:  319 SRSGKTSCARAGLLSVVVDTLSTNVIPDILIIPVGISYDRIIEGH-YNGEQLGKPKKNES 377
            SR+GK      + GLLS+VV+         +PDIL++PV ISYDRIIEG+ Y E  G PKK ES
Sbjct:   62 SRTGKMLPPKTGLLSMVVEAFLRGSVPDILLVPVSISYDRIIEGNTYAHELRGAPKKKES 121
```

FIG. 4E

```
Query:  378  LWSVARGVIRMLRKNYGCVRVDFAQPFSLKEY  409
             LW + RGV +IRML+ +NYG V VDF +P SL+EY
Sbjct:  122  LWQLFRGVRKMLKRNYGQVYVDFGEPISLREY  153

Score = 64 (27.6 bits), Expect = 4.7e-42, Sum P(2) = 4.7e-42
Identities = 30/143 (20%), Positives = 59/143 (41%)

Query:  453  RNATDESLRRRLIANLAEHILFTASKSCAIMSTHIVACLLLYRHRQGIDLSTL---VEDF  509
             RN + + +R + + ++ + + +T +V+ LLL + L L ++D
Sbjct:  160  RNTYNCAPKRLALQKMSFEVAWRILQATPVTATGLVSALLLTTRGTALTLDQLHHTLQDS  219

Query:  510  FVMKEEVLARDFDLGFSGNSEDVVMHAIQLL--GNCVTITHTSRNDEFFITPSTTVPSVF  567
             E +           S + V  A  L G+ VT + R   ++I P   + F
Sbjct:  220  LDYLERKQSPVSTSALRLRSREGVRAAADALSNGHPVTRVDSGREPVWYIAPDDEHAAAF  279

Query:  568  ELNFYSNGVLHVFIMEAIIACSL  590
             Y N V+H F+   +I+   +L
Sbjct:  280  ----YRNSVIHAFLETSIVELAL  298
```

View Prodom PD037846

>PD037846 p2001.1 (15) PLSB(5) DAPT(2) // ACYLTRANSFERASE GLYCEROL-3-PHOSPHATE
   PHOSPHOLIPID GPAT BIOSYNTHESIS MITOCHONDRIAL TRANSMEMBRANE PRECURSOR
   MITOCHONDRION
   Length = 345

Score = 258 (95.9 bits), Expect = 3.4e-21, P = 3.4e-21
Identities = 56/132 (42%), Positives = 79/132 (59%)

FIG. 4F

```
Query:  128  NVTENVLNSSRVQEAIAEVAAELNPDGSAQQQSXXXXXXXXXXXXRILQEMVATVSPAMIR  187
             N+ +NVLNS   +   I +         A++ S                RIL EM  T++ MIR
Sbjct:  223  NLKKNVLNSEEIHYVIEQ------EAKESSTSIDKVRREAREILDEMSHTLNMGMIR     273

Query:  188  LTGWVLLKLENSFFWNIQIHKGQLEMVKAATETNLPLLELPVHRSHIDYLLLTFILFCHN  247
             GWVL K+FN  F   I +++ Q+E +K ATE   P+++LP HRSHIDYLL+FIL+ ++
Sbjct:  274  FCGWVLSKIFNRIFSGICVNEEQIEKIKRATEQGHPVIYLPSHRSHIDYLLLSFILYHYD  333

Query:  248  IKAPYIASGNNL  259
             IK P+IA+G NL
Sbjct:  334  IKVPHIAAGMNL  345
```

View Prodom PD347660

>PD347660 p2001.1 (2) PLSB(2) // ACYLTRANSFERASE PHOSPHOLIPID BIOSYNTHESIS
PRECURSOR TRANSMEMBRANE GLYCEROL-3-PHOSPHATE GPAT MITOCHONDRION
MITOCHONDRIAL
Length = 55

Score = 250 (93.1 bits), Expect = 2.4e-20, P = 2.4e-20
Identities = 43/55 (78%), Positives = 53/55 (96%)

```
Query:  1  MDESALTLGTIDVSYLPHSSEYSVGRCKHTSEEWGECGFRPTVFRSATLKWKESL  55
           M+ES++T+GTIDVSYLP+SSEYS+GRCKHT+E+W +CGF+PT FRSATLKWKESL
Sbjct:  1  MEESSVTIGTIDVSYLPNSSEYSLGRCKHTNEDWVDCGFKPTFFRSATLKWKESL  55
```

FIG. 4G

View Prodom PD042027

>PD042027 p2001.1 (6) PLSB(2) // ACYLTRANSFERASE GLYCEROL-3-PHOSPHATE MEMBRANE
PHOSPHOLIPID GPAT BIOSYNTHESIS MUTANT
Length = 345

```
Score = 80 (33.2 bits), Expect = 0.11, Sum P(2) = 0.10
Identities = 31/129 (24%), Positives = 60/129 (46%)

Query:  465  IANLAEHILFTASKSCAIMSTHIVACLLLYRHRQGIDLSTLVE--DFFVMKEEVLARDFD  522
             + +LA+ I+ + + A+ ++ A LL ++ + L+E D ++     D
Sbjct:  32   VNHLAKQIMTHINDAAAVNPMNLCATALLSTRQRALGEEQLIEQLDCYLKLLRNVPYSTD  91

Query:  523  LGFSGNS-EDVVMHAIQ--LLGNCVTITHTSRNDEFFITPSTTVPSVFELNFYSNGVLHV  579
             ++ E ++ HA Q  LLG VT+ + D + V + +Y N VLH+
Sbjct:  92   ATLPDHTPERLIEHAEQMNLLG--VTVEKDTLGDILRLDRDNAVL----MTYRNNVLHL  145

Query:  580  FIMEAIIAC  588
             F + A++AC
Sbjct:  146  FALPALVAC  154

Score = 62 (26.9 bits), Expect = 0.11, Sum P(2) = 0.10
Identities = 22/105 (20%), Positives = 48/105 (45%)

Query:  569  LNFYSNGVLHVFIMEAIIACSLYAVLNKRGLGGPTSTPPNLISQEQLVRKAASLCYLLSN  628
             + +Y N VLH+ + A++AC N+R IS++ L+R +L L
Sbjct:  135  MTYYRNNVLHLFALPALVACCFKN--NRR------ISRDALLRFVRALYPELQA  180

Query:  629  EGTISLPCQTFYQVCHETVGKFIQYGILTVAEHDDQEDISPSLAE  673
             E + +F++ G+L A + ++ + ++
Sbjct:  181  ELFLRWNEDELNDHIDQWINEFVRQGLLLSAGNQEDDTLTRNTSQ  225
```

FIG. 4H

View Prodom PD087501

>PD087501 p2001.1 (1) // AIP2-DLD1
 Length = 170

Score = 77 (32.2 bits), Expect = 5.1, P = 0.994
Identities = 31/114 (27%), Positives = 44/114 (38%)

Query:  51  WKES--LMSRKRPFVGRCCYSCTPQSWDKFFNPSIPSLGLRNVIYINETHTRHRGWLARR  108
            W ES   L+ RK  F RCC    P  K   P K   + L   N   +H  W
Sbjct:  12  WNESEVLVDRKSKFQARCC----PLQNQKDIPSILQELTQNNKSVSKASHMHMYAWRTAE  67

Query: 109  LSYVLFIQERDVHKGMFATNVTENVLNSSR---VQ-EAIAEVAAELNPDGSAQQ  158
            +S  L +Q+     G  A   + +N SR   VQ + I +    A+    G+  Q+
Sbjct:  68  VSNNLHLQQEQKKGNKANKSNNSHVNKSRNITVQPKNIEQGCADCGEAGAGQR  121

FIG. 5A

```
              10        20        30        40
1    MDESALTLGTIDVSYLPHSSEYSVGRCKHTSEEWGECGFR   56919.pro
1    MEESSVTVGTIDVSYLPSSSEYSLGRCKHTSEDWVDCGFK   MouseGPAT.PRO
1    MEESSVTIGTIDVSYLPNSSEYSLGRCKHTNEDWVDCGFK   RatGPAT.PRO 50        60        70        80
41   PTVFRSATLKWKESLMSRKRPFVGRCCYSCTPQSWDKFFN   56919.pro
41   PTFFRSATLKWKESLMSRKRPFVGRCCYSCTPQSWERFFN   MouseGPAT.PRO
41   PTFFRSATLKWKESLMSRKRPFVGRCCYSCTPQSWERFFN   RatGPAT.PRO 90        100       110       120
81   PSIPSLGLRNVIYINETHTRHRGWLARRLSYVLFIQERDV   56919.pro
81   PSIPSLGLRNVIYINETHTRHRGWLARRLSYILFVQERDV   MouseGPAT.PRO
81   PSIPSLGLRNVIYINETHTRHRGWLARRLSYILFVQERDV   RatGPAT.PRO 130       140       150       160
121  HKGMFATNVTENVLNSSRVQEAIAEVAAELNPDGSAQQQS   56919.pro
121  HKGMFATSVTENVLSSSRVQEAIAEVAAELNPDGSAQQQS   MouseGPAT.PRO
121  HKGMFATSITDNVLNSSRVQEAIAEVAAELNPDGSAQQQS   RatGPAT.PRO 170       180       190       200
161  KAVNKVKKKAKRILQEMVATVSPAMIRLTGWVLLKLFNSF   56919.pro
161  KAIQKVKRKARKILQEMVATVSPGMIRLTGWVLLKLFNSF   MouseGPAT.PRO
161  KAIQKVKRKARKILQEMVATVSPGMIRLTGWVLLKLFNSF   RatGPAT.PRO 210       220       230       240
201  FWNIQIHKGQLEMVKAATETNLPLLFLPVHRSHIDYLLLT   56919.pro
201  FWNIQIHKGQLEMVKAATETNLPLLFLPVHRSHIDYLLLT   MouseGPAT.PRO
201  FWNIQIHKGQLEMVKAATETNLPLLFLPVHRSHIDYLLLT   RatGPAT.PRO 250       260       270       280
241  FILFCHNIKAPYIASGNNLNIPIFSTLIHKLGGFFIRRRL   56919.pro
241  FILFCHNIKAPYIASGNNLNIPVFSTLIHKLGGFFIRRRL   MouseGPAT.PRO
241  FILFCHNIKAPYIASGNNLNIPIFSTLIHKLGGFFIRRRL   RatGPAT.PRO 290       300       310       320
281  DETPDGRKDVLYRALLHGHIVELLRQQQFLEIFLEGTRSR   56919.pro
281  DETPDGRKDILYRALLHGHVVELLRQQQFLEIFLEGTRSR   MouseGPAT.PRO
281  DETPDGRKDILYRALLHGHIVELLRQQQFLEIFLEGTRSR   RatGPAT.PRO 330       340       350       360
321  SGKTSCARAGLLSVVVDTLSTNVIPDILIIPVGISYDRII   56919.pro
321  SGKTSCARAGVLSVVVNTLSSNTIPDILVIPVGISYDRII   MouseGPAT.PRO
321  SGKTSCARAGLLSVVVDTLSSNTIPDILVIPVGISYDRII   RatGPAT.PRO
```

FIG. 5B

```
              370       380       390       400
361 EGHYNGEQLGKPKKNESLWSVARGVIRMLRKNYGCVRVDF 56919.pro
361 EGHYNGEQLGKPKKNESLWSVARGVIRMLRKNYGYVRVDF MouseGPAT.PRO
361 EGHYNGEQLGKPKKNESLWSVARGVIRMLRKNYGYVRVDF RatGPAT.PRO 410       420       430       440
401 AQPFSLKEYLESQSQKPVSALLSLEQALLPAILPSRPSDA 56919.pro
401 AQPFSLKEYLEGQSQKPVSAPLSLEQALLPAILPSRPNDV MouseGPAT.PRO
401 AQPFSLKEYLEGQSQKPVSAPLSLEQALLPAILPSRPDAA RatGPAT.PRO 450       460       470       480
441 ADEGRDTSINESRNATDESLRRRLIANLAEHILFTASKSC 56919.pro
441 ADEHQDLSINESRNPADEAFRRRLIANLAEHILFTASKSC MouseGPAT.PRO
441 AAEHEDMSINESRNAADEAFRRRLIANLAEHILFTASKSC RatGPAT.PRO 490       500       510       520
481 AIMSTHIVACLLLYRHRQGIDLSTLVEDFFVMKEEVLARD 56919.pro
481 AIMSTHIVACLLLYRHRQGIHLSTLVEDFFVMKEEVLARD MouseGPAT.PRO
481 AIMSTHIVACLLLYRHRQGIHLSTLVEDFFVMKEEVLARD RatGPAT.PRO 530       540       550       560
521 FDLGFSGNSEDVVMHAIQLLGNCVTITHTSRNDEFFITPS 56919.pro
521 FDLGFSGNSEDVVMHAIQLLGNCVTITHTSRKDEFFITPS MouseGPAT.PRO
521 FDLGFSGNSEDVVMHAIQLLGNCVTITHTSRKDEFFITPS RatGPAT.PRO 570       580       590       600
561 TTVPSVFELNFYSNGVLHVFIMEAIIACSLYAVLNKRGLG 56919.pro
561 TTVPSVFELNFYSNGVLHVFIMEAIIACSLYAVLNKRCSG MouseGPAT.PRO
561 TTVPSVFELNFYSNGVLHVFIMEAIIACSLYAVQNKRGSG RatGPAT.PRO 610       620       630       640
601 GPTSTPPNLISQEQLVRKAASLCYLLSNEGTISLPCQTFY 56919.pro
601 GPTSTPPNLISQEQLVRKAASLCYLLSNEGTISLPCQTFY MouseGPAT.PRO
601 GPTSTPPNLISQEQLVRKAASLCYLLSNEGTISLPCQTFY RatGPAT.PRO 650       660       670       680
641 QVCHETVGKFIQYGILTVAEHDDQEDISPSLAEQQWDKKL 56919.pro
641 QVCHETVGKFIQYGILTVAEQDDQEDVSPGLAEQQWDKKL MouseGPAT.PRO
641 QVCQETVGKFIQYGILTVAEQDDQEDVSPGLAEQQWNKKL RatGPAT.PRO 690       700       710       720
681 PEPLSWRSDEEDEDSDFGEEQRDCYLKVSQSKEHQQFITF 56919.pro
681 PE-LNWRSDEEDEDSDFGEEQRDCYLKVSQSKEHQQFITF MouseGPAT.PRO
681 PEPLNWRSDEEDEDSDFGEEQRDCYLKVSQAKEHQQFITF RatGPAT.PRO
```

FIG. 5C

```
            730        740        750        760
721 LQRLLGPLLEAYSSAAIFVHNFSGPVPEPEYLQKLHKYLI    56919.pro
721 LQRLLGPLLEAYSSAAIFVHNFSGPVPEPEYLQRLHKYLI    MouseGPAT.PRO
721 LQRLLGPLLEAYSSAAIFVHTFRGPVPEPEYLQRLHKYLI    RatGPAT.PRO 770        780        790        800
761 TRTERNVAVYAESATYCLVKNAVKMFKDIGVFKETKQKRV    56919.pro
761 TRTERNVAVYAESATYCLVKNAVKMFKDIGVFKETKQKRV    MouseGPAT.PRO
761 TRTERNVAVYAESATYCLVKNAVKMFKDIGVFKETKQKRA    RatGPAT.PRO 810        820
801 SVLELSSTFLPQCNRQKLLEYILSFVVL               56919.pro
801 SVLELSSTFLPQCNRQKLLEYILSFVVL               MouseGPAT.PRO
801 SVLELSSTFLPQCNRQKLLEYILSFVVL               RatGPAT.PRO
```

FIG.6

Acyltransferase catalytic motif-I

| | |
|---|---|
| IFLEGTRSR | 56919.pro |
| IFLEGTRSR | MouseGPAT.PRO |
| IFLEGTRSR | RatGPAT.PRO |
| YFVEGGRSR | EcoliGPAT.PRO |

Acyltransferase catalytic motif-II

| | |
|---|---|
| HRSHID | 56919.pro |
| HRSHID | MouseGPAT.PRO |
| HRSHID | RatGPAT.PRO |
| HRSHMD | EcoliGPAT.PRO |

Acyltransferase catalytic motif-III

| | |
|---|---|
| ILIIPV | 56919.pro |
| ILVIPV | MouseGPAT.PRO |
| ILVIPV | RatGPAT.PRO |
| ITLIPI | EcoliGPAT.PRO |

Acyltransferase signature motif

| | |
|---|---|
| GGFFIRR | 56919.pro |
| GGFFIRR | MouseGPAT.PRO |
| GGFFIRR | RatGPAT.PRO |
| GAFFIRR | EcoliGPAT.PRO |

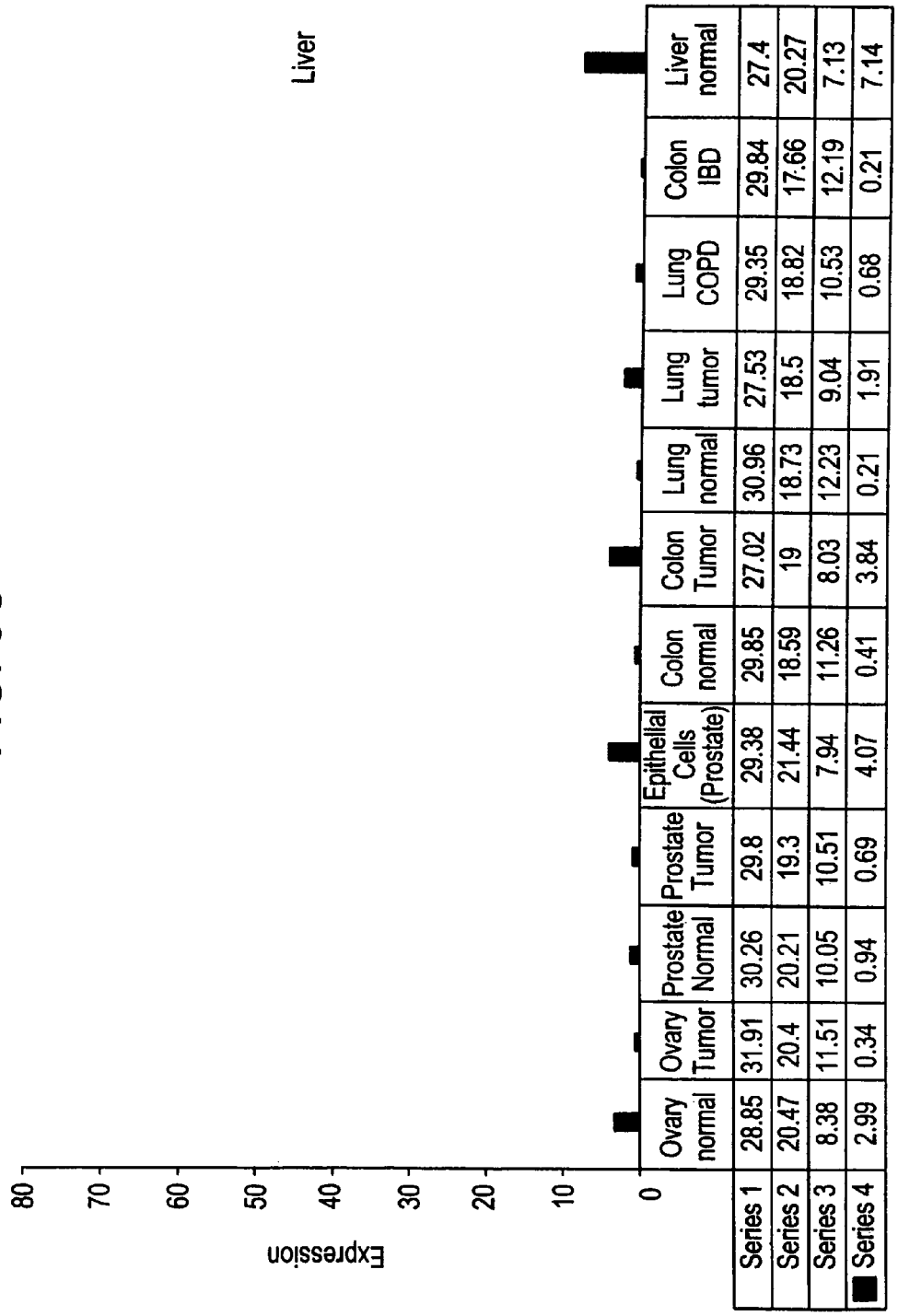

| | Liver fibrosis | Dermal Cells-fibroblasts | Spleen normal | Tonsil normal | Lymph node | Small Intestine | Skin-Decubitus | Synovium | BM-MNC (Bone marrow) | Activated PBMC |
|---|---|---|---|---|---|---|---|---|---|---|
| Series 1 | 27.16 | 30.01 | 30.19 | 26.22 | 30.2 | 30.15 | 31.3 | 31.18 | 28.62 | 28.3 |
| Series 2 | 21.89 | 20.05 | 19.88 | 17.32 | 18.7 | 20.15 | 21.07 | 19.45 | 17 | 16.04 |
| Series 3 | 5.26 | 9.96 | 10.31 | 10.9 | 11.49 | 10 | 10.23 | 11.73 | 11.62 | 12.26 |
| ■ Series 4 | 25.74 | 1.00 | 0.79 | 0.52 | 0.35 | 0.98 | 0.83 | 0.30 | 0.32 | 0.20 |

ACTR-1, A NOVEL HUMAN ACYLTRANSFERASE AND USES THEREOF

RELATED APPLICATIONS

This application is a divisional of U.S. patent application Ser. No. 09/935,290, filed Aug. 21, 2001, now U.S. Pat. No. 7,052,858, which claims the benefit of U.S. provisional patent application Ser. No. 60/226,509, filed Aug. 21, 2000. The contents of these patent applications are incorporated herein by reference in their entirety.

BACKGROUND OF THE INVENTION

Acyltransferases comprise a large family of enzymes that regulate biological processes by catalyzing the transfer of acyl groups to a wide variety of biological and chemical substrates, including proteins, lipids, and nucleic acids (E. C. Webb ed., *Enzyme Nomenclature*, pp. 178-201, ©1992 Academic Press, Inc. San Diego, Calif.).

The biosynthesis of complex lipids involves specific acylation reactions catalyzed by acyltransferases. Lipids are ubiquitous biomolecules that play a critical role in cell structure and metabolism. For example, triacylglycerols are the principal storage form of energy; cholesterol is a component of cell membranes and a precursor of steroid hormones and bile acids; glycolipids and phospholipids are major components of biological membranes; and arachidonate is a precursor of pleiotropic intercellular mediators including the prostaglandins, prostacyclins, thromboxanes, and leukotrienes.

The de novo biosynthesis of glycerophospholipids, which include phospholipids and triacylglycerol, involves the esterification of glycerol-3-phosphate with a fatty acyl-CoA in the sn-1 position by glycerol-3-phosphate acyltransferase (GPAT) to form 1-acylglycerol-3-phosphate (lysophosphatidic acid). Lysophosphatidic acid is then esterified in the sn-2 position with a fatty acyl-CoA by 1-acylglycerol-3-phosphate acyltransferase (AGPAT) to form 1,2-diacylglycerol-3-phosphate (phosphatidic acid). Ultimately, phosphatidic acid can be converted to phosphatidylinositol, phosphatidylglycerol and cardiolipin via a CDP-diacylglycerol intermediate. Alternatively, phosphatidic acid can be dephosphorylated to form diacylglycerol, which is used for the synthesis of triacylglycerol, as well as phospholipids including phosphatidylcholine and phosphatidlyethanolamine.

Glycerol-3-phosphate acyltransferase (GPAT) is the first committed, and presumably rate-limiting, step in glycerophospholipid biosynthesis (Wilkison, WO and Bell, R M (1997) *Biochim. Biophys. Acta* 1348:3-9; Dircks, L and Sul H S (1999) *Prog. Lipid Res.* 38:461-479). Two isoforms of this enzyme have been detected in mammals, a mitochondrial and an endoplasmic reticulum isoform, which can be distinguished by differential sensitivity to N-ethylmaleimide (NEM). Treatment of mitochondrial GPAT with arginine-modifying agents, phenylglyoxal and cyclohexanedione, incativated the enzyme (Dircks, L et al. (1999) *J. Biol. Chem.* 274:34728-34). The expression of mitochondrial GPAT is under nutritional and hormonal control in lipogenic tissues such as liver and adipose tissue, as is regulated during adipocyte differentiation (Yet, S-F et al. (1993) *Biochemistry* 32:9486-91; Yet, S-F et al. (1995) *Biochemistry* 34:7303-10).

Acyltransferases also play an important role in the fatty acid remodeling of phospholipids, as well as the metabolism of bioactive lipids (Yamashita, A et al. (1997) *J. Biochem.* 122:1-16). Fatty acid remodeling is central to physiological processes including the regulation of the physiochemical properties of membranes, e.g., membrane fluidity, and the regulation of the distribution and accumulation of biologically active fatty acids, e.g., arachidonic acid. The phospholipid bilayer of biological membranes serves as a permeability barrier to compartmentalize specialized functions in the cell, and mediates cellular functions such as ion and metabolite transport, electron transport, and signal transduction. Moreover, fatty acylation of cellular proteins may have important functional consequences such as the modulation of subcellular localization (e.g., membrane targeting) and signaling. Therefore, acyltransferases contribute to the ability of the cell to grow and differentiate, to proliferate, to adhere and move, and to interact and communicate with other cells.

SUMMARY OF THE INVENTION

The present invention is based, at least in part, on the discovery of novel acyltransferase family members, referred to herein as "Acyltransferase-1" or "ACTR-1" nucleic acid and protein molecules. In particular, the acyltransferase molecules of the present invention are Glycerol-3-phosphate acyltransferase molecules and, accordingly, can be referred to interchangebly as GPAT protein and to protein molecules. The ACTR-1 nucleic acid and protein molecules of the present invention are useful as modulating agents in regulating a variety of cellular processes, e.g., cellular metabolism, (e.g., lipid or energy metabolism, in particular triglyceride and/or phospholipid metabolism), energy homeostasis, inter- and intra-cellular signal transduction, and cellular proliferation, growth, differentiation and/or migration. Accordingly, in one aspect, this invention provides isolated nucleic acid molecules encoding ACTR-1 proteins or biologically active portions thereof, as well as nucleic acid fragments suitable as primers or hybridization probes for the detection of ACTR-1-encoding nucleic acids.

In one embodiment, the invention features an isolated nucleic acid molecule that includes the nucleotide sequence set forth in SEQ ID NO:1 or SEQ ID NO:3. In another embodiment, the invention features an isolated nucleic acid molecule that encodes a polypeptide including the amino acid sequence set forth in SEQ ID NO:2.

In still other embodiments, the invention features isolated nucleic acid molecules including nucleotide sequences that are substantially identical (e.g., 60% identical) to the nucleotide sequence set forth as SEQ ID NO:1 or SEQ ID NO:3. The invention further features isolated nucleic acid molecules including at least 30 contiguous nucleotides of the nucleotide sequence set forth as SEQ ID NO:1 or SEQ ID NO:3. In another embodiment, the invention features isolated nucleic acid molecules which encode a polypeptide including an amino acid sequence that is substantially identical (e.g., 60% identical) to the amino acid sequence set forth as SEQ ID NO:2. Also featured are nucleic acid molecules which encode allelic variants of the polypeptide having the amino acid sequence set forth as SEQ ID NO:2. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10 contiguous amino acid residues of the amino acid sequence of SEQ ID NO:2). In still other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., ACTR-1-encoding nucleic acid molecules). Such vectors can optionally include nucleotide sequences encoding heterologous polypeptides. Also featured are host cells including such vectors (e.g., host cells including vectors suitable for producing ACTR-1 nucleic acid molecules and polypeptides).

In another aspect, the invention features isolated ACTR-1 polypeptides and/or biologically active or antigenic fragments thereof. Exemplary embodiments feature a polypeptide including the amino acid sequence set forth as SEQ ID NO:2, a polypeptide including an amino acid sequence at least 60% identical to the amino acid sequence set forth as SEQ ID NO:2, a polypeptide encoded by a nucleic acid molecule including a nucleotide sequence at least 60% identical to the nucleotide sequence set forth as SEQ ID NO:1 or SEQ ID NO:3. Also featured are fragments of the full-length polypeptides described herein (e.g., fragments including at least 10 contiguous amino acid residues of the sequence set forth as SEQ ID NO:2) as well as allelic variants of the polypeptide having the amino acid sequence set forth as SEQ ID NO:2.

The ACTR-1 polypeptides and/or biologically active or antigenic fragments thereof, are useful, for example, as reagents or targets in assays applicable to treatment and/or diagnosis of ACTR-1 mediated or related disorders. In one embodiment, an ACTR-1 polypeptide or fragment thereof has an ACTR-1 activity. In another embodiment, an ACTR-1 polypeptide or fragment thereof has at least one or more of the following domains and/or motifs: an acyltransferase domain, an acyltransferase catalytic motif, an acyltransferase signature motif, and a transmembrane domain, and optionally, has an ACTR-1 activity. In a related aspect, the invention features antibodies (e.g., antibodies which specifically bind to any one of the polypeptides, as described herein) as well as fusion polypeptides including all or a fragment of a polypeptide described herein.

The present invention further features methods for detecting ACTR-1 polypeptides and/or ACTR-1 nucleic acid molecules, such methods featuring, for example, a probe, primer or antibody described herein. Also featured are kits for the detection of ACTR-1 polypeptides and/or ACTR-1 nucleic acid molecules. In a related aspect, the invention features methods for identifying compounds which bind to and/or modulate the activity of an ACTR-1 polypeptide or ACTR-1 nucleic acid molecule described herein. Also featured are methods for modulating an ACTR-1 activity.

Other features and advantages of the invention will be apparent from the following detailed description and claims.

BRIEF DESCRIPTION OF THE DRAWINGS

FIG. 1A-E depicts the nucleotide sequence of the human ACTR-1 cDNA and the corresponding amino acid sequence. The nucleotide sequence corresponds to nucleic acids 1 to 3003 of SEQ ID NO:1. The amino acid sequence corresponds to amino acids 828 of SEQ ID NO:2. The coding region without the 5' or 3' untranslated regions of the human ACTR-1 gene is shown in SEQ ID NO:3.

FIGS. 3A-B depicts the results of a search which was performed against the HMM database and which resulted in the identification of an "acyltransferase domain" in the human ACTR-1 protein (SEQ ID NO:2). Amino acid residues 215-412 of ACTR-1 (SEQ ID NO:2) are aligned with the HMM acyltransferase domain (SEQ ID NO:4).

FIG. 4A-G depicts the results of a search which was performed against the ProDom database and which resulted in the local alignment of the human ACTR-1 protein with acyltransferase proteins. Amino acid residues of ACTR-1 (SEQ ID NO:2) (Query) are aligned with acyltransferase proteins: PD042760 acyltransferase phospholipid biosynthesis precursor transmembrane glycerol-3 phosphate GPAT mitochondrion mitochondrial (SEQ ID NO:5), PD353751 acyltransferase phospholipid biosynthesis precursor transmembrane glycerol-3-phosphate GPAT mitochondrion mitochondrial (SEQ ID NO:6), PD025192 acyltransferase phospholipid mitochondrial biosynthesis precursor transmembrane glycerol-3-phosphate GPAT mitochondrion (SEQ ID NO:7), PD042466 acyltransferase glycerol-3-phosphate biosynthesis phospholipid GPAT precursor mitochondrial transmembrane mitochondrion (SEQ ID NO:8 and SEQ ID NO:9), PD037846 acyltransferase glycerol-3-phosphate phospholipid GPAT biosynthesis mitochondrial transmembrane precursor mitochondrion (SEQ ID NO:10), PD347660 acyltransferase phospholipid biosynthesis precursor transmembrane glycerol-3-phosphate GPAT mitochondrion mitochondrial (SEQ ID NO:11), PD042027 acyltransferase glycerol-3-phosphate membrane phospholipid GPAT biosynthesis mutant (SEQ ID NO:12 and SEQ ID NO:13), and PD087501 AIP2-DLD1(SEQ ID NO:14).

FIG. 5A-C depicts a multiple sequence alignment of the amino acid sequence human ACTR-1 protein (SEQ ID NO:2) with the amino acid sequences of mouse and rat glycerol-3-phosphate acyltransferase (GENBANK™ Accession Nos. AAA37647 and AAB71605, set forth as SEQ ID NO:10 and SEQ ID NO:11, accordingly.) The alignment was generated using the Clustal algorithm which is part of the MEGALIGN™ software package. The multiple alignment parameters are as follows: Gap Penalty=10; Gap Length Penalty=10. The pairwise alignment parameters are as follows: K-tuple=1; Gap Penalty=3; Window=5; Diagonals Saved=5; Weight Residue Table=PAM250.

FIG. 6 depicts an alignment of the amino acid residues of various acetyltransferase catalytic and/or signature motifs (catalytic motif-I of 56919, MouseGPAT, RatGPAT (SEQ ID NO:17) and EcoliGPAT (SEQ ID NO:18); catalytic motif-II of 56919, MouseGPAT, RatGPAT (SEQ ID NO:19) and EcoliGPAT (SEQ ID NO:20); catalytic motif-III 56919 (SEQ ID NO:21) and MouseGPAT, RatGPAT (SEQ ID NO:22) and EcoliGPAT (SEQ ID NO:23); and signature motif of 56919, MouseGPAT, RatGPAT (SEQ ID NO:24) and EcoliGPAT (SEQ ID NO:25).

FIG. 8A-D is a graph depicting the relative expression of ACTR-1 in various human tissues as determined by a TAQMAN® Quantitative Polymerase Chain Reaction analysis.

FIG. 9A-D is a graph depicting the relative expression of ACTR-1 various liver, heart and adipose tissues as determined by a TAQMAN® Quantitative Polymerase Chain Reaction analysis.

DETAILED DESCRIPTION OF THE INVENTION

Figure 2:
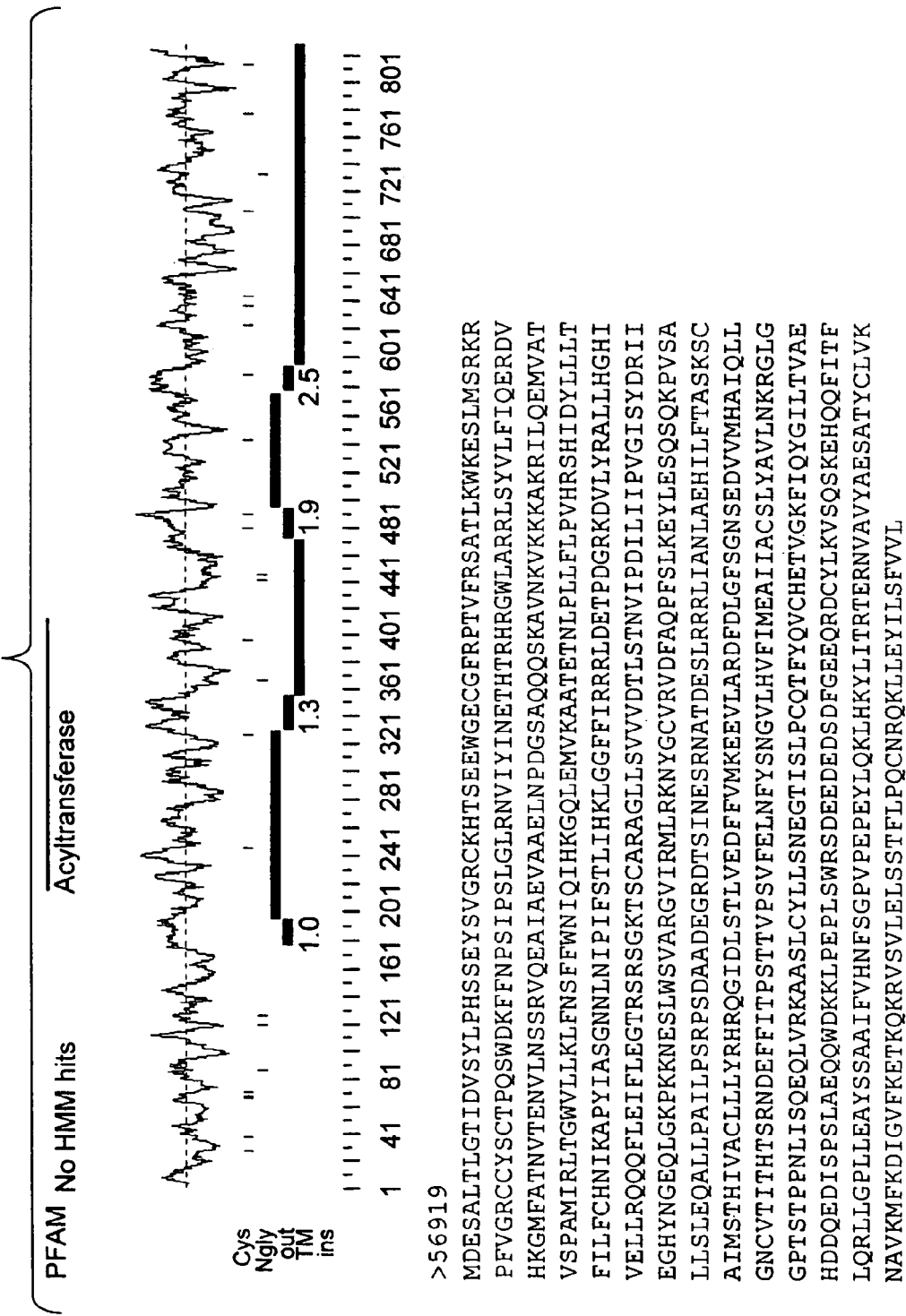
FIG. 2 depicts a structural, hydrophobicity, and antigenicity analysis of the human ACTR-1 protein.
Figure 7A:
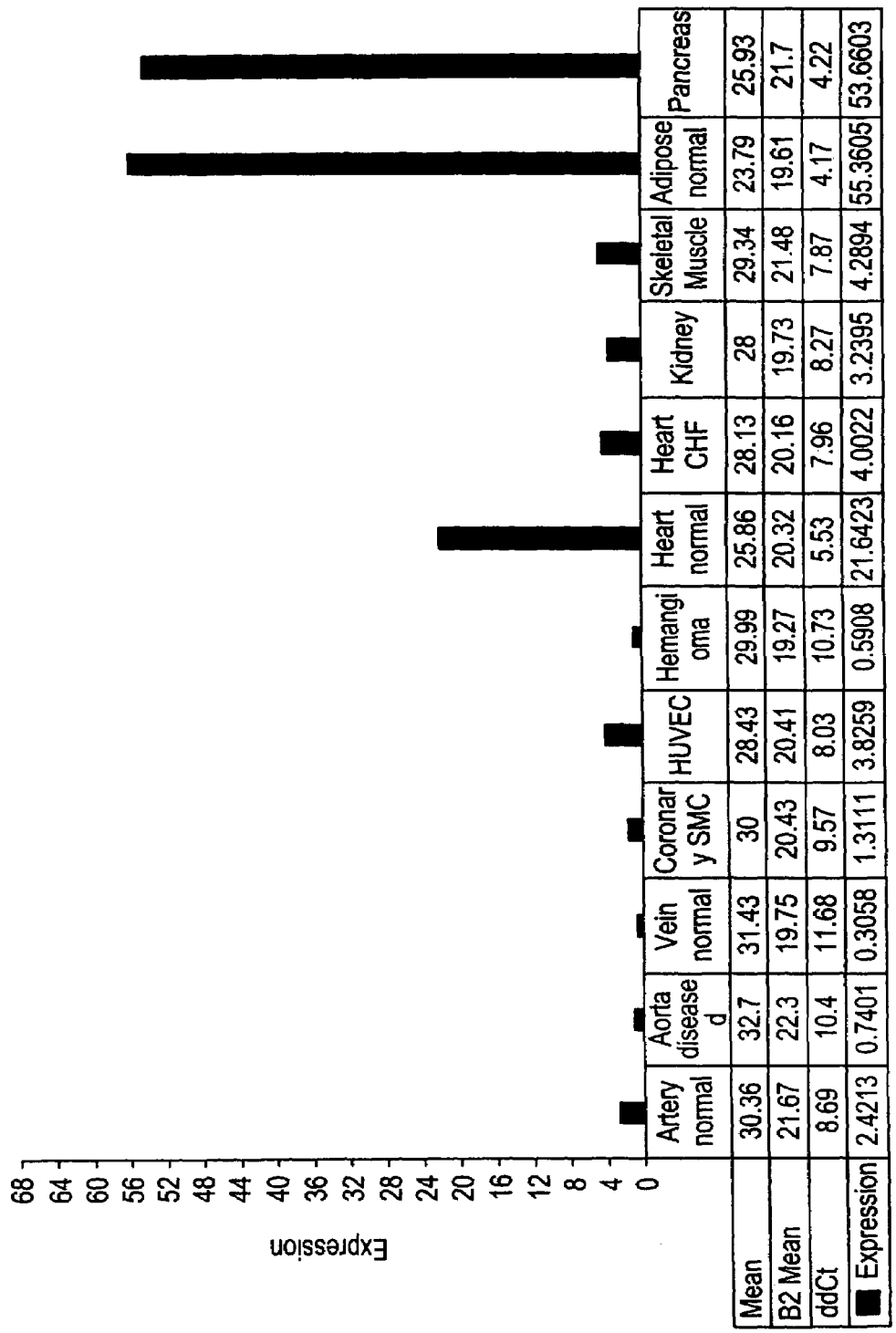
FIG. 7A-D is a graph depicting the relative expression of ACTR-1 in various human tissues as determined by a TAQMAN® Quantitative Polymerase Chain Reaction analysis.
Figure 7B:
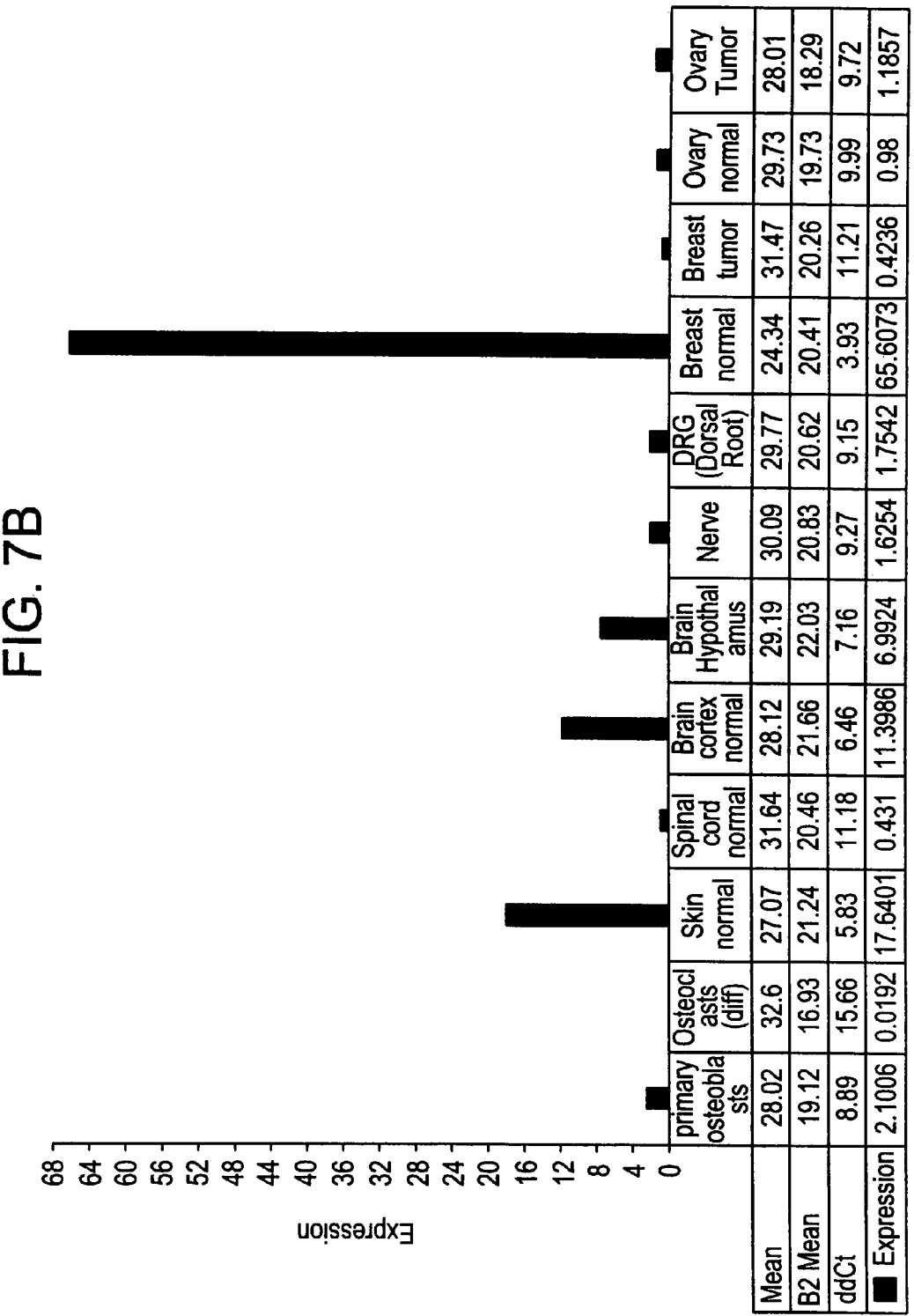
Figure 7C:
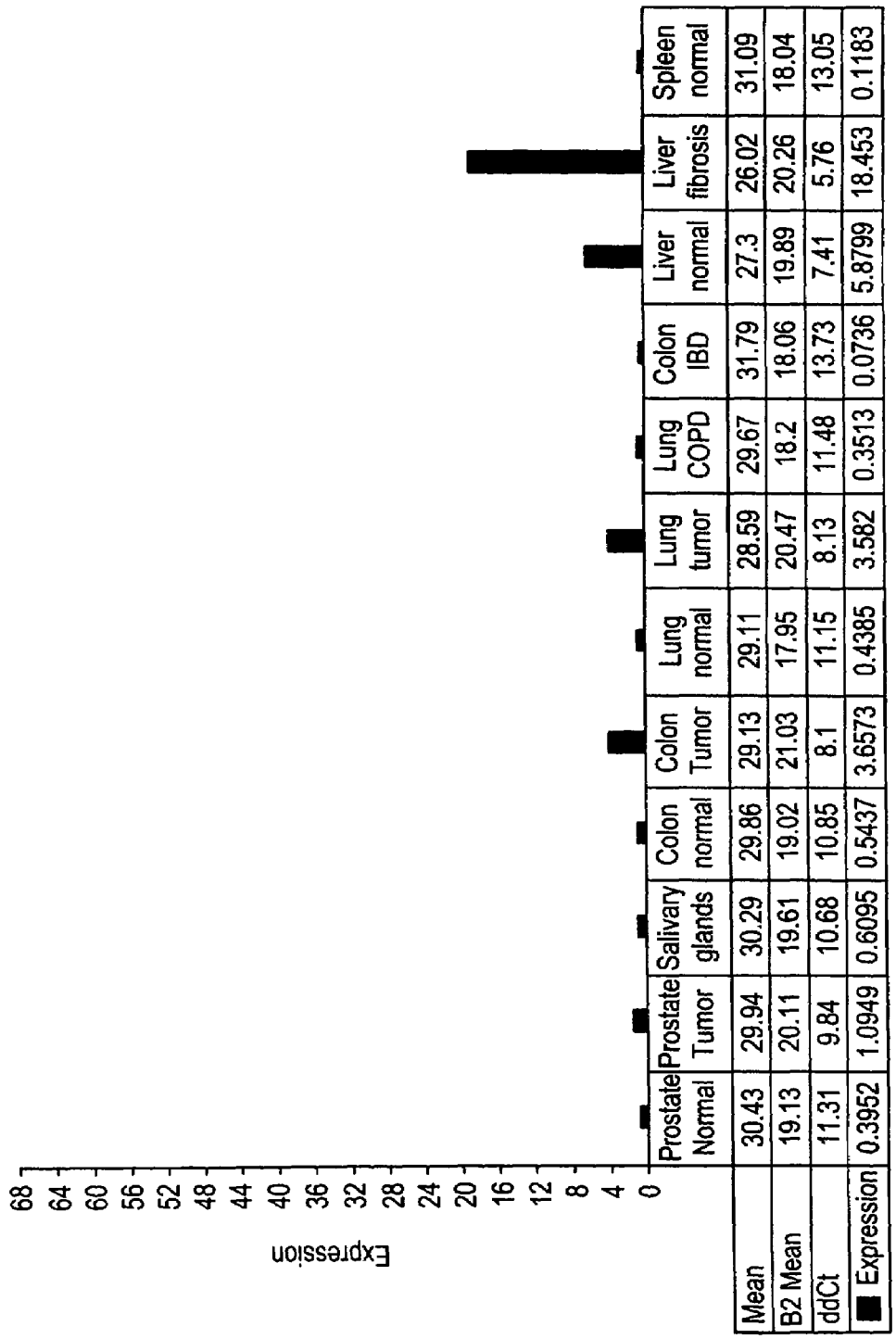
Figure 7D:
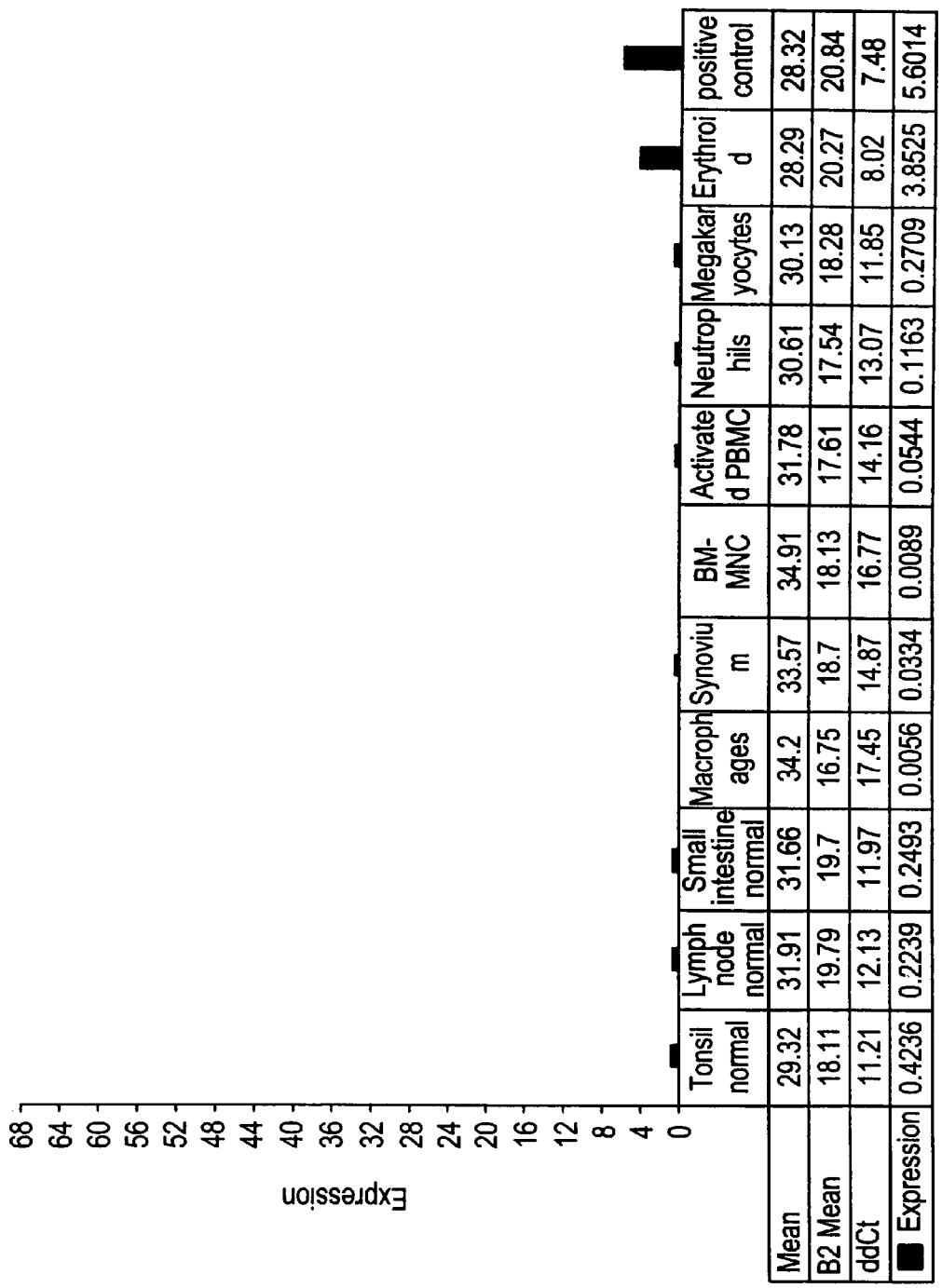

The present invention is based, at least in part, on the discovery of novel acyltransferase family members, referred to herein as "Acyltransferase-1" or "ACTR-1" nucleic acid and protein molecules. Based on their homology to mouse and rat Glycerol-3-phosphate acyltransferases (see e.g., FIG.

5) the ACTR-1 proteins of the present invention can be referred to interchangeably throughout as human GPAT protein and/or nucleic acid molecules. These molecules are novel members of a family of enzymes which are capable of catalyzing the transfer of an acyl group to biological molecules (e.g., lipids, polypeptides) and, thus, play a role in or function in a variety of metabolic and cellular processes, e.g., lipid and protein acylation, intra- or inter-cellular communication (e.g., signal transduction), gene expression, hormonal responses, immune responses, energy homeostasis (e.g., the metabolism of biochemical molecules necessary for energy production or storage), and/or cellular proliferation, growth, differentiation, homeostasis, or migration. In particular, the ACTR-1 molecules of the invention are capable of catalyzing the transfer of a fatty acyl CoA to the sn-1 position of glycerol-3-phosphate, i:e., during the synthesis of triglyceride. Thus, the ACTR-1 molecules of the present invention provide novel diagnostic targets and therapeutic agents to control ACTR-1-associated or acyltransferase-associated disorders and/or triglyceride-associated disorders, as defined herein.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

For example, the family of ACTR-1 proteins of the present invention comprises at least one "acyltransferase domain." As used herein, the term "acyltransferase domain" includes a protein domain having at least about 100-300 amino acid residues and a bit score of at least 80 when compared against an acyltransferase Hidden Markov Model (HMM), e.g., PFAM Accession Number PF01553. Preferably, an acyltransferase domain includes a protein having an amino acid sequence of about 130-270, 160-240, 190-210, or more preferably about 198 amino acid residues, and a bit score of at least 90, 100, 110, 120, or more preferably, 126. To identify the presence of an acyltransferase domain in an ACTR-1 protein, and make the determination that a protein of interest has a particular profile, the amino acid sequence of the protein is searched against a database of known protein domains (e.g., the HMM database). The acyltransferase domain (HMM) has been assigned the PFAM Accession number PF01553. A search was performed against the HMM database resulting in the identification of an acyltransferase domain in the amino acid sequence of human ACTR-1 at about residues 215-412 of SEQ ID NO:2. The results of the search are set forth in FIG. 3.

Preferably an "acyltransferase domain" is at least about 100-300 amino acid residues and has an "acyltransferase domain activity," for example, the ability to interact with a substrate molecule (e.g., a lipid, protein, or nucleic acid), transfer an acyl group to a substrate, modulate inter- and/or intra-cellular signaling mechanisms, modulate cellular metabolism (e.g. lipid metabolism), and/or modulate cellular growth, differentiation, homeostasis and/or migration. In a preferred embodiment, an acyltransferase domain catalyzes the transfer of an acyl group to a substrate, for example, a substrate selected from the group consisting of: glycerol-3-phosphate, 1-acylglycerol-3-phosphate (lysophosphatidic acid), and dihydroxyacetone phosphate.

Accordingly, identifying the presence of an "acyltransferase domain" can include isolating a fragment of an ACTR-1 molecule (e.g., an ACTR-1 polypeptide) and assaying for the ability of the fragment to exhibit one of the aforementioned acyltransferase domain activities.

A description of the Pfam database can be found in Sonhammer et al. (1997) *Proteins* 28:405-420, and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

In another embodiment, members of the ACTR-1 family of proteins include at least one "acyltransferase catalytic motif" in the protein molecule or the nucleic acid molecule encoding the protein molecule. Acyltransferases comprise several conserved regions that contribute to catalysis, referred to herein as "acyltransferase catalytic motif-I, -II and -III". As used herein, the term "acyltransferase catalytic motif" includes the "acyltransferase catalytic motif-I, -II and -III" signature patterns, as described herein.

The "acyltransferase catalytic motif-r" is characterized by a conserved glycine and arginine residues believed to be important for catalytic activity (Lewin, T M et al. (1999) *Biochemistry* 38:5764-71; Dircks, L and Sul H S (1999) *Prog. Lipid Res.* 38:461-479), and in one embodiment has the following signature pattern:

F-[PLI]-E-G-[TG]-R-[SX]-[RX]        (SEQ ID NO:4)

ACTR-1 has such a signature pattern at about amino acids 313-320 of SEQ ID NO:2.

In another embodiment, the acyltransferase catalytic motif-I has the following signature pattern:

I-F-L-E-G-T-R        (SEQ ID NO:5)

ACTR-1 has such a signature pattern at about amino acids 312-318 of SEQ ID NO:2.

The "acyltransferase catalytic motif-H" is characterized by conserved histidine and aspartate residues believed to be important for catalytic activity (Lewin, T M et al. (1999) *Biochemistry* 38:5764-71; Dircks, L and Sul H S (1999) *Prog. Lipid Res.* 38:461-479), and in one embodiment has the following signature pattern:

H-X(4)-D        (SEQ ID NO:6)

ACTR-1 has such a signature pattern at about amino acids 230-235 of SEQ ID NO:2 (H-R-S-H-I-D).

In another embodiment, the acyltransferase catalytic motif-II has the following signature pattern:

H-[RQ]-S-X-[LYIM]-D        (SEQ ID NO:7)

ACTR-1 has such a signature pattern at about amino acids 230-235 of SEQ ID NO:2.

The "acyltransferase catalytic motif-III" is characterized by a conserved proline residue believed to be important for catalytic activity (Lewin, T M et al. (1999) *Biochemistry* 38:5764-71), and in one embodiment has the following signature pattern:

[VI]-[PX]-[IVL]-[IV]-P-[VI]         (SEQ ID NO:8)

ACTR-1 has such a signature pattern at about amino acids 347-352 of SEQ ID NO:2.

In another embodiment, members of the ACTR-1 family of proteins include at least one "acyltransferase signature motif" in the protein molecule or the nucleic acid molecule encoding the protein molecule. The "acyltransferase signature motif" is characterized by conserved phenylalanine and arginine residues believed to be important for substrate binding (Lewin, T M et al. (1999) *Biochemistry* 38:5764-71; Heath, R and Rock, Colo. (1999) *J. Bacteriol.* 181:1944-46), and in one embodiment has the following signature pattern:

G-X-[IF]-F-I-[RD]-R         (SEQ ID NO:9)

ACTR-1 has such a signature pattern at about amino acids 272-278 of SEQ ID NO:2.

The signature patterns or consensus patterns described herein are described according to the following designation: all amino acids are indicated according to their universal single letter designation; "x" designates any amino acid; x(n) designates n number of amino acids, e.g., x (2) designates any two amino acids, e.g., x (1-3) designates any of one to three amino acids; and, amino acids in brackets indicates any one of the amino acids within the brackets, e.g., [RK] indicates any of one of either R (arginine) or K (lysine).

In yet another embodiment, members of the ACTR-1 family of proteins include at least one "transmembrane domain" in the protein or corresponding nucleic acid molecule. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) *Annual Rev. Neurosci.* 19:235-263, the contents of which are incorporated herein by reference. Amino acid residues 177-194, 330-354, 472-494 and 576-594 of the human ACTR-1 protein (SEQ ID NO:2) are predicted to comprise a transmembrane domain.

Isolated proteins of the present invention, preferably ACTR-1 proteins, have an amino acid sequence sufficiently homologous to the amino acid sequence of SEQ ID NO:2, or are encoded by a nucleotide sequence sufficiently homologous to SEQ ID NO:1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 91%, 92%, 93%, 94%, 95%, 96%, 97%, 98%, 99% or more homology or identity across the amino acid sequences of the domains and contain at least one and preferably two structural domains or motifs, are defined herein as sufficiently homologous. Furthermore, amino acid or nucleotide sequences which share at least 50%, 55%, 60%, 65%, 70%, 75%, 80%, 85%, 85%, 90%, 91%, 92%, 93%, 94%, 95%, 96%, 97%, 98%, 99% or more homology or identity and share a common functional activity are defined herein as sufficiently homologous.

In a preferred embodiment, an ACTR-1 protein includes at least one or more of the following domains and/or motifs: an acyltransferase domain, an acyltransferase catalytic motif, an acyltransferase signature motif, and a transmembrane domain, and has an amino acid sequence at least about 50%, 55%, 60%, 65%, 70%, 75%, 80%, 85%, 85%, 90%, 91%, 92%, 93%, 94%, 95%, 96%, 97%, 98%, 99% or more homologous or identical to the amino acid sequence of SEQ ID NO:2. In yet another preferred embodiment, an ACTR-1 protein includes at least one or more of the following domains and/or motifs: an acyltransferase domain, an acyltransferase catalytic motif, an acyltransferase signature motif, and a transmembrane domain, and is encoded by a nucleic acid molecule having a nucleotide sequence which hybridizes under stringent hybridization conditions to a complement of a nucleic acid molecule comprising the nucleotide sequence of SEQ ID NO:1 or 3. In another preferred embodiment, an ACTR-1 protein includes at least one or more of the following domains and/or motifs: an acyltransferase domain, an acyltransferase catalytic motif, an acyltransferase signature motif, and a transmembrane domain, and has an ACTR-1 activity.

As used interchangeably herein, an "ACTR-1 activity", "biological activity of ACTR-1" or "functional activity of ACTR-1", includes an activity exerted or mediated by an ACTR-1 protein, polypeptide or nucleic acid molecule on an ACTR-1 responsive cell or on an ACTR-1 substrate, as determined in vivo or in vitro, according to standard techniques. In one embodiment, an ACTR-1 activity is a direct activity, such as an association with an ACTR-1 target molecule. As used herein, a "target molecule" or "binding partner" is a molecule with which an ACTR-1 protein binds or interacts in nature, such that ACTR-1-mediated function is achieved. An ACTR-1 target molecule can be a non-ACTR-1 molecule or an ACTR-1 protein or polypeptide of the present invention. In an exemplary embodiment, an ACTR-1 target molecule is an ACTR-1 substrate (e.g., glycerol-3-phosphate and/or acyl CoA). An ACTR-1 activity can also be an indirect activity, such as a cellular signaling or metabolic activity mediated by interaction of the ACTR-1 protein with an ACTR-1 substrate or ligand.

In a preferred embodiment, an ACTR-1 activity is at least one of the following activities: (i) interaction with an ACTR-1 substrate or target molecule (e.g., a non-ACTR-1 protein, e.g., a lipid); (ii) conversion of an ACTR-1 substrate or target molecule to a product (e.g., transfer of an acyl group to the substrate or target molecule); (iii) modulation of lipid (e.g. phospholipid and triacylglycerol) biosynthesis and or metabolism; (iv) modulation of fatty acid remodeling of phospholipids; (v) modulation of intra- or inter-cellular signaling and/or gene transcription (e.g., either directly or indirectly); (vi) modulation of cell proliferation, growth, homeostasis, differentiation, and/or migration; (vii) modulation of energy homeostasis (e.g., the metabolism of biochemical molecules necessary for energy production or storage); and (viii) modulation of the anabolism and/or catabolism of metabolically important biomolecules. In another preferred embodiment, an ACTR-1 activity is a glycerol-3-phosphate acyltransferase activity.

The present invention also provides methods and compositions for the diagnosis and treatment of cardiovascular disease or disorder which affects the heart and the blood vessels by which blood is pumped and circulated through the body. "Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, the small molecules, peptides, antibodies, ribozymes and antisense oligonucleotides described herein. As used herein, "cardiovascular disease" or a "cardiovascular disorder" includes a disease or disorder that affects the cardiovascular system, e.g., the heart or the blood vessels, for example, arteriosclerosis, in particular, atherosclerosis. Also provided are methods and compositions for the treatment of disorders of triglyceride and or phospholipid metabolism, including but not limited to hypertriglyceridaemia and obesity.

The present invention provides methods for identifying the presence of an ACTR-1 nucleic acid or polypeptide molecule associated with a cardiovascular disorder or a triglyceride metabolism disorder. In addition, the invention provides methods for identifying a subject at risk for a cardiovascular disorder, or a triglyceride metabolism disorder, by detecting the presence of an ACTR-1 nucleic acid or polypeptide molecule.

The invention also provides a method for identifying a compound capable of treating a cardiovascular disorder or triglyceride metabolism disorder, characterized by aberrant ACTR-1 nucleic acid expression or ACTR-1 protein activity by assaying the ability of the compound to modulate the expression of an ACTR-1 nucleic acid or the activity of an ACTR-1 protein. Furthermore, the invention provides a method for treating a subject having a cardiovascular disorder or a triglyceride metabolism disorder characterized by aberrant ACTR-1 protein activity or aberrant ACTR-1 nucleic acid expression by administering to the subject an ACTR-1 modulator which is capable of modulating ACTR-1 protein activity or ACTR-1 nucleic acid expression.

In a preferred embodiment, the ACTR-1 molecules of the present invention are useful in methods for identifying modulators or are useful themselves as compositions for the diagnosis and treatment of disease or disorder that arise from malfunction of the regulation of triacylglycerol (triglyceride) and phospholipid biosynthesis (e.g., atherosclerosis) as the molecules this invention are closely related to (e.g., orthologs of) the murine and rodent mitochondrial glycerol-3-phosphate acyltransferase (mGPAT), these proteins sharing greater than 90 percent sequence homology. There are two major forms of GPAT in mammalian tissues, microsomal and mitochondrial (Bell, R. M., and Coleman, R. A. (1983) in *The Enzymes* (Boyer, P. D., ed) pp. 87-89, Academic Press, New York). In liver, 50% of GPAT activity is found in the mitochondrial fraction, while in most other tissues microsomal GPAT activity is about 10 times that of the mitochondrial fraction (Schlossman, D. M., and Bell, R. M. (1976) *J. Biol. Chem.* 251, 5738-5744). GPAT, in general, has been shown to play a pivotal role in the regulation of triacylglycerol and phospholipid biosynthesis (Bell, R. M., and Coleman, R. A. supra). Triacylglycerol concentration is further involved in cardiovascular disease, including, but not limited to atherosclerosis. For example, increase in triacylglycerol level is a major risk factor for the development of atherosclerotic heart disease (Coleman R A et al. (2000) *Annu Rev Nutr* 20:77-103) and is also implicated in high blood pressure (Orchard T J (2001) *Diabetes Care* 24:1053-9).

The nucleotide sequence of the isolated human ACTR-1 cDNA and the predicted amino acid sequence encoded by the ACTR-1 cDNA are shown in FIG. 1 and in SEQ ID NO: 1 and 2, respectively.

The human ACTR-1 gene, which is approximately 3003 nucleotides in length, encodes a protein having a molecular weight of approximately 91 kD and which is approximately 828 amino acid residues in length.

Various aspects of the invention are described in further detail in the following subsections:

I. Isolated Nucleic Acid Molecules

One aspect of the invention pertains to isolated nucleic acid molecules that encode ACTR-1 proteins or biologically active portions thereof, as well as nucleic acid fragments sufficient for use as hybridization probes to identify ACTR-1-encoding nucleic acid molecules (e.g., ACTR-1 mRNA) and fragments for use as PCR primers for the amplification or mutation of ACTR-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ACTR-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. Using all or a portion of the nucleic acid sequence of SEQ ID NO:1 or 3, as hybridization probes, ACTR-1 nucleic acid molecules can be isolated using standard hybridization and cloning techniques (e.g., as described in Sambrook, J., Fritsh, E. F., and Maniatis, T. *Molecular Cloning: A Laboratory Manual.* 2$^{nd}$, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ACTR-1 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1 or 3. This cDNA may comprise sequences encoding the human ACTR-1 protein (e.g., the "coding region", from nucleotides 341-2827), as well as 5' untranslated sequencse (nucleotides 1-340) and 3' untranslated sequences (nucleotides 2828-3003) of SEQ ID NO:1. Alternatively, the nucleic acid molecule can comprise only the coding region of SEQ ID NO:1 (e.g., nucleotides 341-2827, corresponding to SEQ ID NO:3). Accordingly, in another embodiment, an isolated nucleic acid molecule of the invention comprises SEQ ID NO:3 and nucleotides 1-340 of SEQ ID NO:1. In yet another embodiment, the isolated nucleic acid molecule comprises SEQ ID NO:3 and nucleotides 2828-3003 of SEQ ID NO:1. In yet another embodiment, the nucleic acid molecule consists of the nucleotide sequence set forth as SEQ ID NO:1 or SEQ ID NO:3.

In still another embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3 is one which is sufficiently complementary to the nucleotide sequence shown in SEQ ID NO:1 or 3, such that it can hybridize to the nucleotide sequence shown in SEQ ID NO:1 or 3, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99% or more identical to the nucleotide sequence shown in SEQ ID NO:1 or 3 (e.g., to the entire length of the nucleotide sequence) or a portion or complement of any of these nucleotide sequences. In one embodiment, a nucleic acid molecule of the present invention comprises a nucleotide sequence which is at least (or no greater than) 50-100, 100-250, 250-500, 500-750, 750-1000, 1000-1250, 1250-1500, 1500-1750, 1750-2000, 2000-2250, 2250-2500, 2500-2750 or more nucleotides in length and hybridizes under stringent hybridization conditions to a complement of a nucleic acid molecule of SEQ ID NO:1 or 3.

Moreover, the nucleic acid molecule of the invention can comprise only a portion of the nucleic acid sequence of SEQ ID NO:1 or 3, for example, a fragment which can be used as a probe or primer or a fragment encoding a portion of an ACTR-1 protein, e.g., a biologically active portion of an ACTR-1 protein. The nucleotide sequence determined from the cloning of the ACTR-1 gene allows for the generation of probes and primers designed for use in identifying and/or cloning other ACTR-1 family members, as well as ACTR-1 homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3 of an anti-sense sequence of SEQ ID NO:1 or 3 or of a naturally occurring allelic variant or mutant of SEQ ID NO:1 or 3.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleoitdes of an isolated nucleic acid molecule described herein, but for the difference of 1, 2, 3, 4, 5, 6, 7, 8, 9 or 10 bases within the probe or primer sequence. Probes based on the ACTR-1 nucleotide sequences can be used to detect (e.g., specifically detect) transcripts or genomic sequences encoding the same or homologous proteins. In preferred embodiments, the probe further comprises a label group attached thereto, e.g., the label group can be a radio-isotope, a fluorescent compound, an enzyme, or an enzyme co-factor. In another embodiment a set of primers is provided, e.g., primers suitable for use in a PCR, which can be used to amplify a selected region of an ACTR-1 sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress an ACTR-1 protein, such as by measuring a level of an ACTR-1-encoding nucleic acid in a sample of cells from a subject, e.g., detecting ACTR-1 mRNA levels or determining whether a genomic ACTR-1 gene has been mutated or deleted.

A nucleic acid fragment encoding a "biologically active portion of an ACTR-1 protein" can be prepared by isolating a portion of the nucleotide sequence of SEQ ID NO:1 or 3, which encodes a polypeptide having an ACTR-1 biological activity (the biological activities of the ACTR-1 proteins are described herein), expressing the encoded portion of the ACTR-1 protein (e.g., by recombinant expression in vitro) and assessing the activity of the encoded portion of the ACTR-1 protein. In an exemplary embodiment, the nucleic acid molecule is at least 50-100, 100-250, 250-500, 500-700, 750-1000, 1000-1250, 1250-1500, 1500-1750, 1750-2000, 2000-2250, 2250-2500, 2500-2750 or more nucleotides in length and encodes a protein having an ACTR-1 activity (as described herein).

The invention further encompasses nucleic acid molecules that differ from the nucleotide sequence shown in SEQ ID NO:1 or 3 due to degeneracy of the genetic code and thus encode the same ACTR-1 proteins as those encoded by the nucleotide sequence shown in SEQ ID NO:1 or 3.

In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2. In yet another embodiment, the nucleic acid molecule encodes the amino acid sequence of human ACTR-1. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the ACTR-1 proteins. Such genetic polymorphism in the ACTR-1 genes may exist among individuals within a population due to natural allelic variation. As used herein, the terms "gene" and "recombinant gene" refer to nucleic acid molecules which include an open reading frame encoding an ACTR-1 protein, preferably a mammalian ACTR-1 protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, wherein the nucleic acid molecule hybridizes to a complement of a nucleic acid molecule comprising SEQ ID NO:1 or 3, for example, under stringent hybridization conditions.

Allelic variants of ACTR-1, e.g., human ACTR-1, include both functional and non-functional ACTR-1 proteins. Functional allelic variants are naturally occurring amino acid sequence variants of the ACTR-1 protein that maintain the ability to bind an ACTR-1 ligand or substrate, transfer an acyl group to an ACTR-1 substrate, and/or modulate the metabolism of biochemical molecules, signal transduction, and/or cell proliferation, growth and/or differentiation mechanisms. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the ACTR-1 protein, e.g., human ACTR-1, that do not have the ability to either bind or interact with an ACTR-1 ligand or substrate, transfer an acyl group to an ACTR-1 substrate, and/or modulate any of the ACTR-1 activities described herein. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

The present invention further provides non-human orthologues (e.g., non-human orthologues of the human ACTR-1 protein). Orthologues of the human ACTR-1 protein are proteins that are isolated from non-human organisms and possess the same ACTR-1 substrate or ligand binding mechanisms, acyltransferase activity, and/or modulation of cell proliferation, differentiation, signaling, homeostasis and/or metabolism properties of the human ACTR-1 protein. Orthologues of the human ACTR-1 protein can readily be identified as comprising an amino acid sequence that is substantially homologous to SEQ ID NO:2.

Moreover, nucleic acid molecules encoding other ACTR-1 family members and, thus, which have a nucleotide sequence which differs from the ACTR-1 sequences of SEQ ID NO:1 or 3 are intended to be within the scope of the invention. For example, another ACTR-1 cDNA can be identified based on the nucleotide sequence of human ACTR-1. Moreover, nucleic acid molecules encoding ACTR-1 proteins from different species, and which, thus, have a nucleotide sequence which differs from the ACTR-1 sequences of SEQ ID NO:1 or 3 are intended to be within the scope of the invention. For example, a mouse or monkey ACTR-1 cDNA can be identified based on the nucleotide sequence of a human ACTR-1.

Nucleic acid molecules corresponding to natural allelic variants and homologues of the ACTR-1 cDNAs of the invention can be isolated based on their homology to the ACTR-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the ACTR-1 cDNAs of the invention can further be isolated by mapping to the same chromosome or locus as the ACTR-1 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 50-100, 100-250, 250-500, 500-700, 750-1000, 1000-1250, 1250-1500, 1500-1750, 1750-2000, 2000-2250, 2250-2500, 2500-2750, 2750 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10 C. less than the melting temperature ($T_m$) of the hybrid, where $T_m$ is determined according to the following equations. For hybrids less than 18 base pairs in length, $T_m(° C.)=2(\# \text{ of } A+T \text{ bases})+4(\# \text{ of } G+C \text{ bases})$. For hybrids between 18 and 49 base pairs in length, $T_m(° C.)=81.5+16.6(\log_{10}[Na^+])+0.41(\% \text{ } G+C)-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C. (see e.g., Church and Gilbert (1984) Proc. Natl. Acad. Sci. USA 81:1991-1995), or alternatively 0.2×SSC, 1% SDS.

Preferably, an isolated nucleic acid molecule of the invention that hybridizes under stringent conditions to the sequence of SEQ ID NO:1 or 3 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the ACTR-1 sequences that may exist in the population, the skilled artisan will further appreciate that changes can be introduced by mutation into the nucleotide sequences of SEQ ID NO:1 or 3, thereby leading to changes in the amino acid sequence of the encoded ACTR-1 proteins, without altering the functional ability of the ACTR-1 proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of ACTR-1 (e.g., the sequence of SEQ ID NO:2) without altering the biological activity, whereas an "essential" amino acid residue is required for biological activity. For example, amino acid residues that are conserved among the ACTR-1 proteins of the present invention, e.g., those present in an acyltransferase domain, an acyltransferase catalytic motif, or an acyltransferase signature motif, are predicted to be particularly unamenable to alteration. Furthermore, additional amino acid residues that are conserved between the ACTR-1 proteins of the present invention and other members of the acyltransferase family (Lewin, T M et al., supra) are not likely to be amenable to alteration.

Accordingly, another aspect of the invention pertains to nucleic acid molecules encoding ACTR-1 proteins that contain changes in amino acid residues that are not essential for activity. Such ACTR-1 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98% 99% or more homologous to SEQ ID NO:2, e.g., to the entire length of SEQ ID NO:2.

An isolated nucleic acid molecule encoding an ACTR-1 protein homologous to the protein of SEQ ID NO:2 can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an ACTR-1 protein is preferably replaced with another amino acid residue from the same side chain family. Alternatively, in another embodiment, mutations can be introduced randomly along all or part of an ACTR-1 coding sequence, such as by saturation mutagenesis, and the resultant mutants can be screened for ACTR-1 biological activity to identify mutants that retain activity. Following mutagenesis of SEQ ID NO:1 or 3, the encoded protein can be expressed recombinantly and the activity of the protein can be determined.

In a preferred embodiment, a mutant ACTR-1 protein can be assayed for the ability to: (i) interact with an ACTR-1 substrate or target molecule (e.g., a non-ACTR-1 protein, e.g., a lipid); (ii) convert an ACTR-1 substrate or target molecule to a product (e.g., transfer an acyl group to the substrate or target molecule); (iii) modulate lipid biosynthesis and/or metabolism; (iv) modulate fatty acid remodeling of phospholipids; (v) modulate intra- or inter-cellular signaling and/or gene transcription (e.g., either directly or indirectly); (vi) modulate cell proliferation, growth, homeostasis, differentiation, and/or migration; (vii) modulate energy homeostasis (e.g., the metabolism of biochemical molecules necessary for energy production or storage); and (viii) modulate the anabolism and/or catabolism of metabolically important biomolecules.

In addition to the nucleic acid molecules encoding ACTR-1 proteins described above, another aspect of the invention pertains to isolated nucleic acid molecules which are antisense thereto. In an exemplary embodiment, the invention provides an isolated nucleic acid molecule which is antisense to an ACTR-1 nucleic acid molecule (e.g., is antisense to the coding strand of an ACTR-1 nucleic acid molecule). An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire ACTR-1 coding strand, or to only a portion thereof. In one embodiment, an antisense nucleic acid molecule is antisense to "coding region sequences" of the coding strand of a nucleotide sequence encoding ACTR-1. The term "coding region sequences" refers to the region of the nucleotide sequence comprising codons which are translated into amino acid residues (e.g., the coding region sequences of human ACTR-1 corresponding to SEQ ID NO:3). In another embodiment, the antisense nucleic acid molecule is antisense to a "noncoding region" of the coding strand of a nucleotide sequence encoding ACTR-1. The term "noncoding region" refers to 5' and/or 3' sequences which flank the coding region sequences that are not translated into amino acids (also referred to as 5' and 3' untranslated regions).

Given the coding strand sequences encoding ACTR-1 disclosed herein (e.g., SEQ ID NO:3), antisense nucleic acids of the invention can be designed according to the rules of Watson and Crick base pairing. The antisense nucleic acid molecule can be complementary to coding region sequences of ACTR-1 mRNA, but more preferably is an oligonucleotide which is antisense to only a portion of the ACTR-1 mRNA. An antisense oligonucleotide can be, for example, about 5, 10, 15, 20, 25, 30, 35, 40, 45, 50, 55, 60, 65, 70, 75, 80, or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ACTR-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res*. 15:6625-6641). The antisense nucleic acid molecule can also comprise a 2'-o-methylribonucleotide (Inoue et al. (1987) *Nucleic Acids Res*. 15:6131-6148) or a chimeric RNA-DNA analogue (Inoue et al. (1987) *FEBS Lett*. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave ACTR-1 mRNA transcripts to thereby inhibit translation of ACTR-1 mRNA. A ribozyme having specificity for an ACTR-1-encoding nucleic acid can be designed based upon the nucleotide sequence of an ACTR-1 cDNA disclosed herein (i.e., SEQ ID NO:1 or 3). For example, a derivative of a *Tetrahymena* L-19 IVS RNA can be constructed in which the nucleotide sequence of the active site is complementary to the nucleotide sequence to be cleaved in an ACTR-1-encoding mRNA. See, e.g., Cech et al. U.S. Pat. No. 4,987,071; and Cech et al. U.S. Pat. No. 5,116,742. Alternatively, ACTR-1 mRNA can be used to select a catalytic RNA having a specific ribonuclease activity from a pool of RNA molecules. See, e.g., Bartel, D. and Szostak, J. W. (1993) *Science* 261:1411-1418.

Alternatively, ACTR-1 gene expression can be inhibited by targeting nucleotide sequences complementary to the regulatory region of the ACTR-1 (e.g., the ACTR-1 promoter and/or enhancers; e.g., nucleotides 1-340 of SEQ ID NO:1) to form triple helical structures that prevent transcription of the ACTR-1 gene in target cells. See generally, Helene, C. (1991) *Anticancer Drug Des*. 6(6):569-84; Helene, C. et al. (1992) *Ann. N.Y. Acad. Sci*. 660:27-36; and Maher, L. J. (1992) *Bioassays* 14(12):807-15.

In yet another embodiment, the ACTR-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. et al. (1996) *Bioorganic & Medicinal Chemistry* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, B. et al. (1996) supra; Perry-O'Keefe et al. (1996) *Proc. Natl. Acad. Sci. USA* 93:14670-675.

PNAs of ACTR-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of ACTR-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup, B. et al. (1996) supra)); or as probes or primers for DNA sequencing or hybridization (Hyrup, B. et al. (1996) supra; Perry-O'Keefe et al. (1996) supra).

In another embodiment, PNAs of ACTR-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of ACTR-1 nucleic acid molecules can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, B. et al. (1996) supra). The synthesis of PNA-DNA chimeras can be performed as described in Hyrup, B. et al. (1996) supra and Finn, P. J. et al. (1996) Nucleic Acids Res. 24 (17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) Nucleic Acid Res. 17:5973-88). PNA monomers are then coupled in a stepwise manner to produce a chimeric molecule with a 5' PNA segment and a 3' DNA segment (Finn, P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

II. Isolated ACTR-1 Proteins and Anti-ACTR-1 Antibodies

One aspect of the invention pertains to isolated or recombinant ACTR-1 proteins and polypeptides, and biologically active portions thereof, as well as polypeptide fragments suitable for use as immunogens to raise anti-ACTR-1 antibodies. In one embodiment, native ACTR-1 proteins can be isolated from cells or tissue sources by an appropriate purification scheme using standard protein purification techniques. In another embodiment, ACTR-1 proteins are produced by recombinant DNA techniques. Alternative to recombinant expression, an ACTR-1 protein or polypeptide can be synthesized chemically using standard peptide synthesis techniques.

An "isolated" or "purified" protein or biologically active portion thereof is substantially free of cellular material or other contaminating proteins from the cell or tissue source from which the ACTR-1 protein is derived, or substantially free from chemical precursors or other chemicals when chemically synthesized. The language "substantially free of cellular material" includes preparations of ACTR-1 protein in which the protein is separated from cellular components of the cells from which it is isolated or recombinantly produced. In one embodiment, the language "substantially free of cellular material" includes preparations of ACTR-1 protein having less than about 30% (by dry weight) of non-ACTR-1 protein (also referred to herein as a "contaminating protein"), more preferably less than about 20% of non-ACTR-1 protein, still more preferably less than about 10% of non-ACTR-1 protein, and most preferably less than about 5% non-ACTR-1 protein. When the ACTR-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ACTR-1 protein in which the protein is separated from chemical precursors or other chemicals which are involved in the synthesis of the protein. In one embodiment, the language "substantially free of chemical precursors or other chemicals" includes preparations of ACTR-1 protein having less than about 30% (by dry weight) of chemical precursors or non-ACTR-1 chemicals, more preferably less than about 20% chemical precursors or non-ACTR-1 chemicals, still more preferably less than about 10% chemical precursors or non-ACTR-1 chemicals, and most preferably less than about 5% chemical precursors or non-ACTR-1 chemicals.

As used herein, a "biologically active portion" of an ACTR-1 protein includes a fragment of an ACTR-1 protein which participates in an interaction between an ACTR-1 molecule and a non-ACTR-1 molecule (e.g., an ACTR-1 substrate). Biologically active portions of an ACTR-1 protein include peptides comprising amino acid sequences sufficiently homologous to or derived from the ACTR-1 amino acid sequences, e.g., the amino acid sequences shown in SEQ ID NO:2, which include sufficient amino acid residues to exhibit at least one activity of an ACTR-1 protein. Typically, biologically active portions comprise a domain or motif with at least one activity of the ACTR-1 protein, e.g., acyltransferase activity, modulation of cellular metabolism (e.g., lipid metabolism), modulation of intra- or inter-cellular signaling, and/or modulation of cell growth, homeostasis, proliferation, migration, and/or differentiation mechanisms. A biologically active portion of an ACTR-1 protein can be a polypeptide which is, for example, 10, 25, 50, 75, 100, 125, 150, 175, 198, 200, 250, 300 or more amino acids in length. Biologically active portions of an ACTR-1 protein can be used as targets for developing agents which modulate an ACTR-1 mediated activity, e.g., acyltransferase activity, modulation of cellular metabolism (e.g., lipid metabolism), modulation of intra- or inter-cellular signaling, and/or modulation of cell growth, homeostasis, proliferation, migration, and/or differentiation mechanisms.

In one embodiment, a biologically active portion of an ACTR-1 protein comprises at least one or more of the following domains and/or motifs: an acyltransferase domain, an acyltransferase catalytic motif, an acyltransferase signature motif, and a transmembrane domain. Moreover, other biologically active portions, in which other regions of the protein are deleted, can be prepared by recombinant techniques and evaluated for one or more of the functional activities of a native ACTR-1 protein.

Another aspect of the invention features fragments of the protein having the amino acid sequence of SEQ ID NO:2, for example, for use as immunogens. In one embodiment, a fragment comprises at least 5 amino acids (e.g., contiguous or consecutive amino acids) of the amino acid sequence of SEQ ID NO:2. In another embodiment, a fragment comprises at least 10, 15, 20, 25, 30, 35, 40, 45, 50 or more amino acids (e.g., contiguous or consecutive amino acids) of the amino acid sequence of SEQ ID NO:2.

In a preferred embodiment, an ACTR-1 protein has an amino acid sequence shown in SEQ ID NO:2. In other embodiments, the ACTR-1 protein is substantially identical to SEQ ID NO:2, and retains the functional activity of the protein of SEQ ID NO:2, yet differs in amino acid sequence due to natural allelic variation or mutagenesis, as described in detail in subsection I above. In another embodiment, the ACTR-1 protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:2.

In another embodiment, the invention features an ACTR-1 protein which is encoded by a nucleic acid molecule consisting of a nucleotide sequence at least about 50%, 55%, 60%, 65%, 70%, 75%, 80%, 85%, 90%, 91%, 92%, 93%, 94%, 95%, 99% or more identical to a nucleotide sequence of SEQ ID NO:1 or 3, or a complement thereof. This invention further features an ACTR-1 protein which is encoded by a nucleic acid molecule consisting of a nucleotide sequence which hybridizes under stringent hybridization conditions to a complement of a nucleic acid molecule comprising the nucleotide sequence of SEQ ID NO:1 or 3, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the ACTR-1 amino acid sequence of SEQ ID NO:2 having 828 amino acid residues, at least 248, preferably at least 331, more preferably at least 414, even more preferably at least 497, and even more preferably at least 580, 662 or 745 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.*, 4:11-17 (1988)) which has been incorporated into the ALIGN program (version 2.0 or version 2.0 U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to ACTR-1 nucleic acid molecules of the invention. BLAST protein searches can be performed with the XBLAST program, score=50, wordlength=3 to obtain amino acid sequences homologous to ACTR-1 protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The invention also provides ACTR-1 chimeric or fusion proteins. As used herein, an ACTR-1 "chimeric protein" or "fusion protein" comprises an ACTR-1 polypeptide operatively linked to a non-ACTR-1 polypeptide. An "ACTR-1 polypeptide" refers to a polypeptide having an amino acid sequence corresponding to ACTR-1, whereas a "non-ACTR-1 polypeptide" refers to a polypeptide having an amino acid sequence corresponding to a protein which is not substantially homologous to the ACTR-1 protein, e.g., a protein which is different from the ACTR-1 protein and which is derived from the same or a different organism. Within an ACTR-1 fusion protein the ACTR-1 polypeptide can correspond to all or a portion of an ACTR-1 protein. In a preferred embodiment, an ACTR-1 fusion protein comprises at least one biologically active portion of an ACTR-1 protein. In another preferred embodiment, an ACTR-1 fusion protein comprises at least two biologically active portions of an ACTR-1 protein. Within the fusion protein, the term "operatively linked" is intended to indicate that the ACTR-1 polypeptide and the non-ACTR-1 polypeptide are fused in-frame to each other. The non-ACTR-1 polypeptide can be fused to the N-terminus or C-terminus of the ACTR-1 polypeptide.

For example, in one embodiment, the fusion protein is a GST-ACTR-1 fusion protein in which the ACTR-1 sequences are fused to the C-terminus of the GST sequences. Such fusion proteins can facilitate the purification of recombinant ACTR-1. In another embodiment, the fusion protein is an ACTR-1 protein containing a heterologous signal sequence at its N-terminus. In certain host cells (e.g., mammalian host cells), expression and/or secretion of ACTR-1 can be increased through use of a heterologous signal sequence.

The ACTR-1 fusion proteins of the invention can be incorporated into pharmaceutical compositions and administered to a subject in vivo. The ACTR-1 fusion proteins can be used to affect the bioavailability of an ACTR-1 substrate. Use of ACTR-1 fusion proteins may be useful therapeutically for the treatment of disorders caused by, for example, (i) aberrant modification or mutation of a gene encoding an ACTR-1 protein; (ii) mis-regulation of the ACTR-1 gene; and (iii) aberrant post-translational modification of an ACTR-1 protein.

Moreover, the ACTR-1-fusion proteins of the invention can be used as immunogens to produce anti-ACTR-1 antibodies in a subject, to purify ACTR-1 substrates, and in screening assays to identify molecules which inhibit or enhance the interaction of ACTR-1 with an ACTR-1 substrate.

Preferably, an ACTR-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An ACTR-1-encoding nucleic acid can be cloned into such an expression vector such that the fusion moiety is linked in-frame to the ACTR-1 protein.

The present invention also pertains to variants of the ACTR-1 proteins which function as either ACTR-1 agonists (mimetics) or as ACTR-1 antagonists. Variants of the ACTR-1 proteins can be generated by mutagenesis, e.g., discrete point mutation or truncation of an ACTR-1 protein. An agonist of the ACTR-1 proteins can retain substantially the same, or a subset, of the biological activities of the naturally occurring form of an ACTR-1 protein. An antagonist of an ACTR-1 protein can inhibit one or more of the activities of the naturally occurring form of the ACTR-1 protein by, for example, competitively modulating an ACTR-1-mediated activity of an ACTR-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the ACTR-1 protein.

In one embodiment, variants of an ACTR-1 protein which function as either ACTR-1 agonists (mimetics) or as ACTR-1 antagonists can be identified by screening combinatorial libraries of mutants, e.g., truncation mutants, of an ACTR-1 protein for ACTR-1 protein agonist or antagonist activity. In one embodiment, a variegated library of ACTR-1 variants is generated by combinatorial mutagenesis at the nucleic acid level and is encoded by a variegated gene library. A variegated library of ACTR-1 variants can be produced by, for example, enzymatically ligating a mixture of synthetic oligonucleotides into gene sequences such that a degenerate set of potential ACTR-1 sequences is expressible as individual polypeptides, or alternatively, as a set of larger fusion proteins (e.g., for phage display) containing the set of ACTR-1 sequences therein. There are a variety of methods which can be used to produce libraries of potential ACTR-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ACTR-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an ACTR-1 protein coding sequence can be used to generate a variegated population of ACTR-1 fragments for screening and subsequent selection of variants of an ACTR-1 protein. In one embodiment, a library of coding sequence fragments can be generated by treating a double stranded PCR fragment of an ACTR-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ACTR-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ACTR-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify ACTR-1 variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated ACTR-1 library. For example, a library of expression vectors can be transfected into a cell line, e.g., an adipocyte or pre-adipocyte cell line, which ordinarily responds to ACTR-1 in a particular ACTR-1 substrate-dependent manner. The transfected cells are then contacted with ACTR-1 and the effect of the expression of the mutant on signaling by the ACTR-1 substrate can be detected, e.g., by measuring levels of acylated residues in the substrate, or the modulation of ACTR-1 dependent metabolism of biochemical molecules (e.g., lipids), signal transduction, or cell proliferation and/or differentiation mechanisms. Plasmid DNA can then be recovered from the cells which score for inhibition, or alternatively, potentiation of signaling by the ACTR-1 substrate, and the individual clones further characterized.

An isolated ACTR-1 protein, or a portion or fragment thereof, can be used as an immunogen to generate antibodies that bind ACTR-1 using standard techniques for polyclonal and monoclonal antibody preparation. A full-length ACTR-1 protein can be used or, alternatively, the invention provides antigenic peptide fragments of ACTR-1 for use as immunogens. The antigenic peptide of ACTR-1 comprises at least 8 amino acid residues of the amino acid sequence shown in SEQ ID NO:2 and encompasses an epitope of ACTR-1 such that an antibody raised against the peptide forms a specific immune complex with ACTR-1. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of ACTR-1 that are located on the surface of the protein, e.g., hydrophilic regions, as well as regions with high antigenicity (see, for example, FIG. 2).

An ACTR-1 immunogen typically is used to prepare antibodies by immunizing a suitable subject (e.g., rabbit, goat, mouse, or other mammal) with the immunogen. An appropriate immunogenic preparation can contain, for example, recombinantly expressed ACTR-1 protein or a chemically-synthesized ACTR-1 polypeptide. The preparation can further include an adjuvant, such as Freund's complete or incomplete adjuvant, or similar immunostimulatory agent. Immunization of a suitable subject with an immunogenic ACTR-1 preparation induces a polyclonal anti-ACTR-1 antibody response.

Accordingly, another aspect of the invention pertains to anti-ACTR-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as ACTR-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ACTR-1. The term "monoclonal antibody" or "monoclonal antibody composition", as used herein, refers to a population of antibody molecules that contain only one species of an antigen binding site capable of immunoreacting with a particular epitope of ACTR-1. A monoclonal antibody composition thus typically displays a single binding affinity for a particular ACTR-1 protein with which it immunoreacts.

Polyclonal anti-ACTR-1 antibodies can be prepared as described above by immunizing a suitable subject with an ACTR-1 immunogen. The anti-ACTR-1 antibody titer in the immunized subject can be monitored over time by standard techniques, such as with an enzyme linked immunosorbent assay (ELISA) using immobilized ACTR-1. If desired, the antibody molecules directed against ACTR-1 can be isolated from the mammal (e.g., from the blood) and further purified by well known techniques, such as protein A chromatography to obtain the IgG fraction. At an appropriate time after immunization, e.g., when the anti-ACTR-1 antibody titers are highest, antibody-producing cells can be obtained from the subject and used to prepare monoclonal antibodies by standard techniques, such as the hybridoma technique originally described by Kohler and Milstein (1975) *Nature* 256:495-497 (see also Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.*, 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an ACTR-1 immunogen as described above, and the culture supernatants of the resulting hybridoma cells are screened to identify a hybridoma producing a monoclonal antibody that binds ACTR-1.

Any of the many well known protocols used for fusing lymphocytes and immortalized cell lines can be applied for the purpose of generating an anti-ACTR-1 monoclonal antibody (see, e.g., Galfre, G. et al. (1977) *Nature* 266:55052; Gefter et al. *Somatic Cell Genet.*, supra; Lerner (1981) supra; Kenneth, *Monoclonal Antibodies*, supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ACTR-1, e.g., using a standard ELISA assay.

Alternative to preparing monoclonal antibody-secreting hybridomas, a monoclonal anti-ACTR-1 antibody can be identified and isolated by screening a recombinant combinatorial immunoglobulin library (e.g., an antibody phage display library) with ACTR-1 to thereby isolate immunoglobulin library members that bind ACTR-1. Kits for generating and screening phage display libraries are commercially available (e.g., the Pharmacia *Recombinant Phage Antibody System*, Catalog No. 27-9400-01; and the Stratagene *SURFZAP*™ *Phage Display Kit*, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-ACTR-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-ACTR-1 antibody (e.g., monoclonal antibody) can be used to isolate ACTR-1 by standard techniques, such as affinity chromatography or immunoprecipitation. An anti-ACTR-1 antibody can facilitate the purification of natural ACTR-1 from cells and of recombinantly produced ACTR-1 expressed in host cells. Moreover, an anti-ACTR-1 antibody can be used to detect ACTR-1 protein (e.g., in a cellular lysate or cell supernatant) in order to evaluate the abundance and pattern of expression of the ACTR-1 protein. Anti-ACTR-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidintbiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, for example recombinant expression vectors, containing an ACTR-1 nucleic acid molecule or vectors containing a nucleic acid molecule which encodes an ACTR-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ACTR-1 proteins, mutant forms of ACTR-1 proteins, fusion proteins, and the like).

Accordingly, an exemplary embodiment provides a method for producing a protein, preferably an ACTR-1 protein, by culturing in a suitable medium a host cell of the invention (e.g., a mammalian host cell such as a non-human mammalian cell) containing a recombinant expression vector, such that the protein is produced.

The recombinant expression vectors of the invention can be designed for expression of ACTR-1 proteins in prokaryotic or eukaryotic cells. For example, ACTR-1 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in ACTR-1 activity assays, (e.g., direct assays or competitive assays described in detail below), or to generate antibodies specific for ACTR-1 proteins, for example. In a preferred embodiment, an ACTR-1 fusion protein expressed in a retroviral expression vector of the present invention can be utilized to infect bone marrow cells, which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al. (1990) *Methods Enzymol*. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol*. 185:119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res*. 20:2111-2118). Such alteration of nucleic acid sequences of the invention can be carried out by standard DNA synthesis techniques.

In another embodiment, the ACTR-1 expression vector is a yeast expression vector. Examples of vectors for expression in yeast *S. cerivisae* include pYepSec1 (Baldari, et al. (1987) *Embo J*. 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and picZ (InVitrogen Corp., San Diego, Calif.).

Alternatively, ACTR-1 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol*. 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al. *Molecular Cloning: A Laboratory Manual*. $2^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268-277), lymphoid-specific promoters (Calame and Eaton (1988) *Adv. Immunol*. 43:235-275), in particular promoters of T cell receptors (Winoto and Baltimore (1989) *EMBO J*. 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), adipose-specific promoters (U.S. Pat. No. 5,476,926; WO 92/06104), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev*. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ACTR-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., "Antisense RNA as a molecular tool for genetic analysis", *Reviews—Trends in Genetics*, Vol. 1(1) 1986.

Another aspect of the invention pertains to host cells into which an ACTR-1 nucleic acid molecule of the invention is introduced, e.g., an ACTR-1 nucleic acid molecule within a vector (e.g., a recombinant expression vector) or an ACTR-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ACTR-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. $2^{nd}$, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an ACTR-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an ACTR-1 protein. Accordingly, the invention further provides methods for producing an ACTR-1 protein using the host cells of the invention. In one embodiment, the method comprises culturing the host cell of the invention (into which a recombinant expression vector encoding an ACTR-1 protein has been introduced) in a suitable medium such that an ACTR-1 protein is produced. In another embodiment, the method further comprises isolating an ACTR-1 protein from the medium or the host cell.

The host cells of the invention can also be used to produce non-human transgenic animals. For example, in one embodiment, a host cell of the invention is a fertilized oocyte or an embryonic stem cell into which ACTR-1-coding sequences have been introduced. Such host cells can then be used to create non-human transgenic animals in which exogenous ACTR-1 sequences have been introduced into their genome or homologous recombinant animals in which endogenous ACTR-1 sequences have been altered. Such animals are useful for studying the function and/or activity of an ACTR-1 protein and for identifying and/or evaluating modulators of ACTR-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ACTR-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an ACTR-1-encoding nucleic acid into the male pronuclei of a fertilized oocyte, e.g., by microinjection or retroviral infection, and allowing the oocyte to develop in a pseudopregnant female foster animal. The ACTR-1 cDNA sequence of SEQ ID NO:1 can be introduced as a transgene into the genome of a non-human animal. Alternatively, a non-human homologue of a human ACTR-1 gene, such as a rat or mouse ACTR-1 gene, can be used as a transgene. Alternatively, an ACTR-1 gene homologue, such as another ACTR-1 family member, can be isolated based on hybridization to the ACTR-1 cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to an ACTR-1 transgene to direct expression of an ACTR-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an ACTR-1 transgene in its genome and/or expression of ACTR-1 mRNA in tissues or cells of the animals. A transgenic founder animal can then be used to breed additional animals carrying the transgene. Moreover, transgenic animals carrying a transgene encoding an ACTR-1 protein can further be bred to other transgenic animals carrying other transgenes.

To create a homologous recombinant animal, a vector is prepared which contains at least a portion of an ACTR-1 gene into which a deletion, addition or substitution has been introduced to thereby alter, e.g., functionally disrupt, the ACTR-1 gene. The ACTR-1 gene can be a human gene (e.g., the cDNA of SEQ ID NO:3), but more preferably, is a non-human homologue of a human ACTR-1 gene (e.g., a cDNA isolated by stringent hybridization with the nucleotide sequence of SEQ ID NO:1). For example, a mouse ACTR-1 gene can be used to construct a homologous recombination nucleic acid molecule, e.g., a vector, suitable for altering an endogenous ACTR-1 gene in the mouse genome. In a preferred embodiment, the homologous recombination nucleic acid molecule is designed such that, upon homologous recombination, the endogenous ACTR-1 gene is functionally disrupted (i.e., no longer encodes a functional protein; also referred to as a "knock out" vector). Alternatively, the homologous recombination nucleic acid molecule can be designed such that, upon homologous recombination, the endogenous ACTR-1 gene is mutated or otherwise altered but still encodes functional protein (e.g., the upstream regulatory region can be altered to thereby alter the expression of the endogenous ACTR-1 protein). In the homologous recombination nucleic acid molecule, the altered portion of the ACTR-1 gene is flanked at its 5' and 3' ends by additional nucleic acid sequence of the ACTR-1 gene to allow for homologous recombination to occur between the exogenous ACTR-1 gene carried by the homologous recombination nucleic acid molecule and an endogenous ACTR-1 gene in a cell, e.g., an embryonic stem cell. The additional flanking ACTR-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced ACTR-1 gene has homologously recombined with the endogenous ACTR-1 gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach*, Robertson, E. J. ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The ACTR-1 nucleic acid molecules, ACTR-1 proteins, fragments thereof, anti-ACTR-1 antibodies, and ACTR-1 modulators (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an ACTR-1 protein or an anti-ACTR-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of ACTR-1 activity is administered in combination with other agents (e.g., a small molecule), or in conjunction with another, complementary treatment regime. For example, in one embodiment, a modulator of ACTR-1 activity is used to treat a metabolic disorder, e.g., a disorder associated with aberrant lipid metabolism. Accordingly, modulation of ACTR-1 activity may be used in conjunction with, for example, lipid-lowering agents.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, protein fragments, antibodies, peptides, peptidomimetics, and small molecules described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an ACTR-1 protein of the invention has one or more of the following activities: (i) interaction with an ACTR-1 substrate or target molecule (e.g., a non-ACTR-1 protein, a lipid, a nucleic acid molecule (e.g., DNA or RNA), a hormone, a neurotransmitter); (ii) conversion of an ACTR-1 substrate or target molecule to a product (e.g., transfer of an acyl group to the substrate or target molecule); (iii) modulation of lipid (e.g., phospholipid) biosynthesis; (iv) modulation of fatty acid remodeling of phospholipids; (v) modulation of intra- or inter-cellular signaling and/or gene transcription (e.g., either directly or indirectly); (vi) modulation of cell proliferation, growth, homeostasis, differentiation, and/or migration; (vii) modulation of energy homeostasis (e.g., the metabolism of biochemical molecules necessary for energy production or storage); and (viii) modulation of the anabolism and/or catabolism of metabolically important biomolecules.

The isolated nucleic acid molecules of the invention can be used, for example, to express ACTR-1 protein (e.g., via a recombinant expression vector in a host cell in gene therapy applications), to detect ACTR-1 mRNA (e.g., in a biological sample) or a genetic alteration in an ACTR-1 gene, and to modulate ACTR-1 activity, as described further below. The ACTR-1 proteins can be used to treat disorders characterized by insufficient or excessive production of an ACTR-1 substrate or production of ACTR-1 inhibitors, for example, acyltransferase associated disorders.

As used interchangeably herein, an "acyltransferase-associated disorder" or an "ACTR-1-associated disorder" includes a disorder, disease or condition which is caused or characterized by a misregulation (e.g., downregulation or upregulation) of acyltransferase activity or an ACTR-1-mediated activity. Acyltransferase-associated disorders can detrimentally affect cellular functions such as lipid and/or energy homeostasis; tissue function, such as adipose function, liver function or cardiac function; systemic responses in an organism, such as hormonal responses (e.g., insulin response).

ACTR-1 associated disorders include metabolic disorders such as disorders of energy homeostasis, e.g., diabetes, impaired glucose tolerance, insulin resistance, hyperglycemia, hypercholesterolemia, hyperlipoproteinemia, hypertriglyceridemia, and/or hyperlipidemia as well as diabetic complications include atherosclerosis, stroke, retinopathy, nephropathy, and peripheral neuropathy. ACTR-1 associated metabolic disorders also include weight disorders and appetite regulation disorders, e.g., obesity, cachexia, anorexia and bulimia.

ACTR-1-associated or related disorders also include disorders affecting tissues in which ACTR-1 protein is expressed.

In addition, the ACTR-1 proteins can be used to screen for naturally occurring ACTR-1 substrates, to screen for drugs or compounds which modulate ACTR-1 expression activity, as well as to treat disorders characterized by insufficient or excessive production of ACTR-1 protein or production of ACTR-1 protein forms which have decreased, aberrant or unwanted activity compared to ACTR-1 wild type protein (e.g., an ACTR-1-associated disorder).

Moreover, the anti-ACTR-1 antibodies of the invention can be used to detect and isolate ACTR-1 proteins, regulate the bioavailability of ACTR-1 proteins, and modulate ACTR-1 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to ACTR-1 proteins, have a stimulatory or inhibitory effect on, for example, ACTR-1 expression or ACTR-1 activity, or have a stimulatory or inhibitory effect on, for example, levels of an ACTR-1 substrate or product.

In one embodiment, the invention provides assays for screening candidate or test compounds which are substrates of an ACTR-1 protein or polypeptide or biologically active portion thereof. In another embodiment, the invention provides assays for screening candidate or test compounds which bind to or modulate the activity of an ACTR-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:45).

Examples of methods for the synthesis of molecular libraries can be found in the art, for example, in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.).

In one embodiment, an assay is a cell-based assay in which a cell which expresses an ACTR-1 protein or biologically active portion thereof is contacted with a test compound and the ability of the test compound to modulate ACTR-1 activity is determined. Determining the ability of the test compound to modulate ACTR-1 activity can be accomplished by monitoring, for example: (i) interaction with an ACTR-1 substrate or target molecule (e.g., a lipid); (ii) conversion of an ACTR-1 substrate or target molecule to a product (e.g., transfer of an acyl group to the substrate or target molecule); (iii) modulation of lipid (e.g., phospholipid) biosynthesis; (iv) modulation of fatty acid remodeling of phospholipids; (v) modulation of intra- or inter-cellular signaling and/or gene transcription (e.g., either directly or indirectly); (vi) modulation of cell proliferation, growth, homeostasis, differentiation, and/or migration; (vii) modulation of energy homeostasis (e.g., the metabolism of biochemical molecules necessary for energy production or storage); and (viii) modulation of the anabolism and/or catabolism of metabolically important biomolecules. In one embodiment, ACTR-1 activity can be assessed in an assay for acyltransferase activity as described, for example, in Yet, S-F et al. (1993) *Biochemistry* 32:9486-91, Yet, S-F et al. (1995) *Biochemistry* 34:7303-10, and Bhat, B G et al. (1999) *Biochim. Biophys. Acta* 1439:415-23.

The ability of the test compound to modulate ACTR-1 binding to a substrate or to bind to ACTR-1 can also be determined. Determining the ability of the test compound to modulate ACTR-1 binding to a substrate can be accomplished, for example, by coupling the ACTR-1 substrate with a radioisotope or enzymatic label such that binding of the ACTR-1 substrate to ACTR-1 can be determined by detecting the labeled ACTR-1 substrate in a complex. Alternatively, ACTR-1 could be coupled with a radioisotope or enzymatic label to monitor the ability of a test compound to modulate ACTR-1 binding to an ACTR-1 substrate in a complex. Determining the ability of the test compound to bind ACTR-1 can be accomplished, for example, by coupling the compound with a radioisotope or enzymatic label such that binding of the compound to ACTR-1 can be determined by detecting the labeled compound in a complex. For example, compounds (e.g., ACTR-1 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an ACTR-1 substrate) to interact with ACTR-1 without the labeling of any of the interactants. For example, a microphysiometer can be used to detect the interaction of a compound with ACTR-1 without the labeling of either the compound or the ACTR-1. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ACTR-1.

In another embodiment, an assay is a cell-based assay comprising contacting a cell expressing an ACTR-1 target molecule (e.g., an ACTR-1 substrate) with a test compound and determining the ability of the test compound to modulate (e.g. stimulate or inhibit) the activity of the ACTR-1 target molecule. Determining the ability of the test compound to modulate the activity of an ACTR-1 target molecule can be accomplished, for example, by determining the ability of the ACTR-1 protein to bind to or interact with the ACTR-1 target molecule.

Determining the ability of the ACTR-1 protein or a biologically active fragment thereof, to bind to or interact with an ACTR-1 target molecule can be accomplished by one of the methods described above for determining direct binding. In a preferred embodiment, determining the ability of the ACTR-1 protein to bind to or interact with an ACTR-1 target molecule can be accomplished by determining the activity of the target molecule. For example, the activity of the target molecule can be determined by detecting induction of an acylated target molecule, detecting catalytic/enzymatic activity of the target molecule upon an appropriate substrate, detecting the induction of a reporter gene (comprising a target-responsive regulatory element operatively linked to a nucleic acid encoding a detectable marker, e.g., luciferase), or detecting a target-regulated cellular response (i.e., cell proliferation, differentiation, signal transduction, and/or metabolic activity), In yet another embodiment, an assay of the present invention is a cell-free assay in which an ACTR-1 protein or biologically active portion thereof is contacted with a test compound and the ability of the test compound to bind to the ACTR-1 protein or biologically active portion thereof is determined. Preferred biologically active portions of the ACTR-1 proteins to be used in assays of the present invention include fragments which participate in interactions with non-ACTR-1 molecules, e.g., fragments with high surface probability scores (see, for example, FIG. 2). Binding of the test compound to the ACTR-1 protein can be determined either directly or indirectly as described above. In a preferred embodiment, the assay includes contacting the ACTR-1 protein or biologically active portion thereof with a known compound which binds ACTR-1 to form an assay mixture, contacting the assay mixture with a test compound, and determining the ability of the test compound to interact with an ACTR-1 protein, wherein determining the ability of the test compound to interact with an ACTR-1 protein comprises determining the ability of the test compound to preferentially bind to ACTR-1 or biologically active portion thereof as compared to the known compound.

In another embodiment, the assay is a cell-free assay in which an ACTR-1 protein or biologically active portion thereof is contacted with a test compound and the ability of the test compound to modulate (e.g., stimulate or inhibit) the activity of the ACTR-1 protein or biologically active portion thereof is determined. Determining the ability of the test compound to modulate the activity of an ACTR-1 protein can be accomplished, for example, by determining the ability of the ACTR-1 protein to bind to an ACTR-1 target molecule by one of the methods described above for determining direct binding. Determining the ability of the ACTR-1 protein to bind to an ACTR-1 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an ACTR-1 protein can be accomplished by determining the ability of the ACTR-1 protein to further modulate the activity of a downstream effector of an ACTR-1 target molecule. For example, the activity of the effector molecule on an appropriate target can be determined or the binding of the effector to an appropriate target can be determined as previously described.

In yet another embodiment, the cell-free assay involves contacting an ACTR-1 protein or biologically active portion thereof with a known compound which binds the ACTR-1 protein to form an assay mixture, contacting the assay mixture with a test compound, and determining the ability of the test compound to interact with the ACTR-1 protein, wherein determining the ability of the test compound to interact with the ACTR-1 protein comprises determining the ability of the ACTR-1 protein to preferentially bind to or modulate the activity of an ACTR-1 target molecule.

The cell-free assays of the present invention are amenable to use of both soluble and/or membrane-bound forms of isolated proteins (e.g., ACTR-1 proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100, TRITON® X-114, THESIT®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either ACTR-1 or its target molecule to facilitate separation of complexed from uncomplexed forms of one or both of the proteins, as well as to accommodate automation of the assay. Binding of a test compound to an ACTR-1 protein, or interaction of an ACTR-1 protein with a substrate or target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-5-transferase/ACTR-1 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or ACTR-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of ACTR-1 binding or activity determined using standard techniques.

Other techniques for immobilizing proteins on matrices can also be used in the screening assays of the invention. For example, either an ACTR-1 protein or an ACTR-1 substrate or target molecule can be immobilized utilizing conjugation of biotin and streptavidin. Biotinylated ACTR-1 protein, substrates, or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with ACTR-1 protein or target molecules but which do not interfere with binding of the ACTR-1 protein to its target molecule can be derivatized to the wells of the plate, and unbound target or ACTR-1 protein trapped in the wells by antibody conjugation. Methods for detecting such complexes, in addition to those described above for the GST-immobilized complexes, include immunodetection of complexes using antibodies reactive with the ACTR-1 protein or target molecule, as well as enzyme-linked assays which rely on detecting an enzymatic activity associated with the ACTR-1 protein or target molecule.

In another embodiment, modulators of ACTR-1 expression are identified in a method wherein a cell is contacted with a candidate compound and the expression of ACTR-1 mRNA or protein in the cell is determined. The level of expression of ACTR-1 mRNA or protein in the presence of the candidate compound is compared to the level of expression of ACTR-1 mRNA or protein in the absence of the candidate compound. The candidate compound can then be identified as a modulator of ACTR-1 expression based on this comparison. For example, when expression of ACTR-1 mRNA or protein is greater (statistically significantly greater) in the presence of the candidate compound than in its absence, the candidate compound is identified as a stimulator of ACTR-1 mRNA or protein expression. Alternatively, when expression of ACTR-1 mRNA or protein is less (statistically significantly less) in the presence of the candidate compound than in its absence, the candidate compound is identified as an inhibitor of ACTR-1 mRNA or protein expression. The level of ACTR-1 mRNA or protein expression in the cells can be determined by methods described herein for detecting ACTR-1 mRNA or protein.

In yet another aspect of the invention, the ACTR-1 proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300) to identify other proteins which bind to or interact with ACTR-1 ("ACTR-1-binding proteins" or "ACTR-1-bp") and are involved in ACTR-1 activity. Such ACTR-1-binding proteins are also likely to be involved in the propagation of signals by the ACTR-1 proteins or ACTR-1 targets as, for example, downstream elements of an ACTR-1-mediated signaling pathway. Alternatively, such ACTR-1-binding proteins may be ACTR-1 inhibitors.

The two-hybrid system is based on the modular nature of most transcription factors, which consist of separable DNA-binding and activation domains. Briefly, the assay utilizes two different DNA constructs. In one construct, the gene that codes for an ACTR-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ACTR-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ACTR-1 protein.

In another aspect, the invention pertains to a combination of two or more of the assays described herein. For example, a modulating agent can be identified using a cell-based or a cell-free assay, and the ability of the agent to modulate the activity of an ACTR-1-protein can be confirmed in vivo, e.g., in an animal such as an animal model for a metabolic disorder, e.g., obesity (ob/ob mouse; Zhang, Y et al. (1994) *Science* 372:425-432) or diabetes, or for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an ACTR-1 modulating agent, an antisense ACTR-1 nucleic acid molecule, an ACTR-1-specific antibody, or an ACTR-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the ACTR-1 nucleotide sequences, described herein, can be used to map the location of the ACTR-1 genes on a chromosome. The mapping of the ACTR-1 sequences to chromosomes is an important first step in correlating these sequences with genes associated with.

Briefly, ACTR-1 genes can be mapped to chromosomes by preparing PCR primers (preferably 15-25 bp in length) from the ACTR-1 nucleotide sequences. Computer analysis of the ACTR-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the ACTR-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the ACTR-1 nucleotide sequences to design oligonucleotide primers, sublocalization can be achieved with panels of fragments from specific chromosomes. Other mapping strategies which can similarly be used to map an ACTR-1 sequence to its chromosome include in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome-specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the ACTR-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The ACTR-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the ACTR-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The ACTR-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500-2,000.

If a panel of reagents from ACTR-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial ACTR-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the ACTR-1 nucleotide sequences or portions thereof, e.g., fragments derived from the noncoding regions of SEQ ID NO:1 having a length of at least 20 bases, preferably at least 30 bases.

The ACTR-1 nucleotide sequences described herein can further be used to provide polynucleotide reagents, e.g., labeled or labelable probes which can be used in, for example, an in situ hybridization technique, to identify a specific tissue, e.g., a tissue which expresses ACTR-1. This can be very useful in cases where a forensic pathologist is presented with a tissue of unknown origin. Panels of such ACTR-1 probes can be used to identify tissue by species and/or by organ type.

In a similar fashion, these reagents, e.g., ACTR-1 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining ACTR-1 protein and/or nucleic acid expression as well as ACTR-1 activity, in the context of a biological sample (e.g., blood, serum, cells, or tissue) to thereby determine whether an individual is afflicted with a disease or disorder, or is at risk of developing a disorder, associated with aberrant or unwanted ACTR-1 expression or activity. The invention also provides for prognostic (or predictive) assays for determining whether an individual is at risk of developing a disorder associated with ACTR-1 protein, nucleic acid expression, or activity. For example, mutations in an ACTR-1 gene can be assayed in a biological sample. Such assays can be used for prognostic or predictive purpose to thereby prophylactically treat an individual prior to the onset of a disorder characterized by or associated with ACTR-1 protein, nucleic acid expression or activity.

Another aspect of the invention pertains to monitoring the influence of agents (e.g., drugs, compounds) on the expression or activity of ACTR-1 in clinical trials.

These and other agents are described in further detail in the following sections.

1. Diagnostic Assays

An exemplary method for detecting the presence or absence of ACTR-1 protein, polypeptide or nucleic acid in a biological sample involves obtaining a biological sample from a test subject and contacting the biological sample with a compound or an agent capable of detecting ACTR-1 protein, polypeptide or nucleic acid (e.g., mRNA, genomic DNA) that encodes ACTR-1 protein such that the presence of ACTR-1 protein or nucleic acid is detected in the biological sample. In another aspect, the present invention provides a method for detecting the presence of ACTR-1 activity in a biological sample by contacting the biological sample with an agent capable of detecting an indicator of ACTR-1 activity such that the presence of ACTR-1 activity is detected in the biological sample. A preferred agent for detecting ACTR-1 mRNA or genomic DNA is a labeled nucleic acid probe capable of hybridizing to ACTR-1 mRNA or genomic DNA. The nucleic acid probe can be, for example, a full-length ACTR-1 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to ACTR-1 mRNA or genomic DNA. Other suitable probes for use in the diagnostic assays of the invention are described herein.

A preferred agent for detecting ACTR-1 protein is an antibody capable of binding to ACTR-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect ACTR-1 mRNA, protein, or genomic DNA in a biological sample in vitro as well as in vivo. For example, in vitro techniques for detection of ACTR-1 mRNA include Northern hybridizations and in situ hybridizations. In vitro techniques for detection of ACTR-1 protein include enzyme linked immunosorbent assays (ELISAs), Western blots, immunoprecipitations and immunofluorescence. In vitro techniques for detection of ACTR-1 genomic DNA include Southern hybridizations. Furthermore, in vivo techniques for detection of an ACTR-1 protein include introducing into a subject a labeled anti-ACTR-1 antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding an ACTR-1 protein; (ii) aberrant expression of a gene encoding an ACTR-1 protein; (iii) mis-regulation of the gene; and (iv) aberrant post-translational modification of an ACTR-1 protein, wherein a wild-type form of the gene encodes a protein with an ACTR-1 activity. "Misexpression or aberrant expression", as used herein, refers to a non-wild type pattern of gene expression, at the RNA or protein level. It includes, but is not limited to, expression at non-wild type levels (e.g., over or under expression); a pattern of expression that differs from wild type in terms of the time or stage at which the gene is expressed (e.g., increased or decreased expression (as compared with wild type) at a pre-determined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting ACTR-1 protein, mRNA, or genomic DNA, such that the presence of ACTR-1 protein, mRNA or genomic DNA is detected in the biological sample, and comparing the presence of ACTR-1 protein, mRNA or genomic DNA in the control sample with the presence of ACTR-1 protein, mRNA or genomic DNA in the test sample.

The invention also encompasses kits for detecting the presence of ACTR-1 in a biological sample. For example, the kit can comprise a labeled compound or agent capable of detecting ACTR-1 protein or mRNA in a biological sample; means for determining the amount of ACTR-1 in the sample; and means for comparing the amount of ACTR-1 in the sample with a standard. The compound or agent can be packaged in a suitable container. The kit can further comprise instructions for using the kit to detect ACTR-1 protein or nucleic acid.

2. Prognostic Assays

The diagnostic methods described herein can furthermore be utilized to identify subjects having or at risk of developing a disease or disorder associated with aberrant or unwanted ACTR-1 expression or activity. As used herein, the term "aberrant" includes an ACTR-1 expression or activity which deviates from the wild type ACTR-1 expression or activity. Aberrant expression or activity includes increased or decreased expression or activity, as well as expression or activity which does not follow the wild type developmental pattern of expression or the subcellular pattern of expression. For example, aberrant ACTR-1 expression or activity is intended to include the cases in which a mutation in the ACTR-1 gene causes the ACTR-1 gene to be under-expressed or over-expressed and situations in which such mutations result in a non-functional ACTR-1 protein or a protein which does not function in a wild-type fashion, e.g., a protein which does not interact with an ACTR-1 substrate, or one which interacts with a non-ACTR-1 substrate. As used herein, the term "unwanted" includes an unwanted phenomenon involved in a biological response such as deregulated cell proliferation or seizure suceptibility. For example, the term unwanted includes an ACTR-1 expression or activity which is undesirable in a subject.

The assays described herein, such as the preceding diagnostic assays or the following assays, can be utilized to identify a subject having or at risk of developing a disorder associated with a misregulation in ACTR-1 protein activity or nucleic acid expression, such as a metabolic disorder, a cardiovascular disorder, a cell proliferation, growth or differentiation disorder, a central nervous system disorder, a hormonal disorder, or an inflammatory or immune system disorder. Alternatively, the prognostic assays can be utilized to identify a subject having or at risk for developing a disorder associated with a misregulation in ACTR-1 protein activity or nucleic acid expression, such as a metabolic disorder, a cardiovascular disorder, a cell proliferation, growth or differentiation disorder, a central nervous system disorder, a hormonal disorder, or an inflammatory or immune system disorder. Thus, the present invention provides a method for identifying a disease or disorder associated with aberrant or unwanted ACTR-1 expression or activity in which a test sample is obtained from a subject and ACTR-1 protein or nucleic acid (e.g., mRNA or genomic DNA) is detected, wherein the presence of ACTR-1 protein or nucleic acid is diagnostic for a subject having or at risk of developing a disease or disorder associated with aberrant or unwanted ACTR-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted ACTR-1 expression or activity. For example, such methods can be used to determine whether a subject can be effectively treated with an agent for a metabolic disorder, a cardiovascular disorder, a cell proliferation, growth or differentiation disorder, a central nervous system disorder, a hormonal disorder, or an inflammatory or immune system disorder. Thus, the present invention provides methods for determining whether a subject can be effectively treated with an agent for a disorder associated with aberrant or unwanted ACTR-1 expression or activity in which a test sample is obtained and ACTR-1 protein or nucleic acid expression or activity is detected (e.g., wherein the abundance of ACTR-1 protein or nucleic acid expression or activity is diagnostic for a subject that can be administered the agent to treat a disorder associated with aberrant or unwanted ACTR-1 expression or activity).

The methods of the invention can also be used to detect genetic alterations in an ACTR-1 gene, thereby determining if a subject with the altered gene is at risk for a disorder characterized by misregulation in ACTR-1 protein activity or nucleic acid expression, such as a metabolic disorder, a cardiovascular disorder, a cell proliferation, growth or differentiation disorder, a central nervous system disorder, a hormonal disorder, or an inflammatory or immune system disorder. In preferred embodiments, the methods include detecting, in a sample of cells from the subject, the presence or absence of a genetic alteration characterized by at least one of an alteration affecting the integrity of a gene encoding an ACTR-1-protein, or the mis-expression of the ACTR-1 gene. For example, such genetic alterations can be detected by ascertaining the existence of at least one of 1) a deletion of one or more nucleotides from an ACTR-1 gene; 2) an addition of one or more nucleotides to an ACTR-1 gene; 3) a substitution of one or more nucleotides of an ACTR-1 gene, 4) a chromosomal rearrangement of an ACTR-1 gene; 5) an alteration in the level of a messenger RNA transcript of an ACTR-1 gene, 6) aberrant modification of an ACTR-1 gene, such as of the methylation pattern of the genomic DNA, 7) the presence of a non-wild type splicing pattern of a messenger RNA transcript of an ACTR-1 gene, 8) a non-wild type level of an ACTR-1-protein, 9) allelic loss of an ACTR-1 gene, and 10) inappropriate post-translational modification of an ACTR-1-protein. As described herein, there are a large number of assays known in the art which can be used for detecting alterations in an ACTR-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the ACTR-1-gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to an ACTR-1 gene under conditions such that hybridization and amplification of the ACTR-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874-1878), transcriptional amplification system (Kwoh, D. Y. et al. (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ACTR-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in ACTR-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7:244-255; Kozal, M. J. et al. (1996) *Nature Medicine* 2:753-759). For example, genetic mutations in ACTR-1 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the ACTR-1 gene and detect mutations by comparing the sequence of the sample ACTR-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the ACTR-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type ACTR-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ACTR-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on an ACTR-1 sequence, e.g., a wild-type ACTR-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in ACTR-1 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125-144; and Hayashi (1992) *Genet. Anal. Tech. Appl.* 9:73-79). Single-stranded DNA fragments of sample and control ACTR-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an ACTR-1 gene.

Furthermore, any cell type or tissue in which ACTR-1 is expressed may be utilized in the prognostic assays described herein.

3. Monitoring of Effects During Clinical Trials

Monitoring the influence of agents (e.g., drugs) on the expression or activity of an ACTR-1 protein (e.g., the modulation of cellular signaling mechanisms, the modulation of lipid metabolism, or the modulation of cell proliferation and/or differentiation) can be applied not only in basic drug screening, but also in clinical trials. For example, the effectiveness of an agent determined by a screening assay as described herein to increase ACTR-1 gene expression, protein levels, or upregulate ACTR-1 activity, can be monitored in clinical trials of subjects exhibiting decreased ACTR-1 gene expression, protein levels, or downregulated ACTR-1 activity. Alternatively, the effectiveness of an agent determined by a screening assay to decrease ACTR-1 gene expression, protein levels, or downregulate ACTR-1 activity, can be monitored in clinical trials of subjects exhibiting increased ACTR-1 gene expression, protein levels, or upregulated ACTR-1 activity. In such clinical trials, the expression or activity of an ACTR-1 gene, and preferably, other genes that have been implicated in, for example, an ACTR-1-associated disorder can be used as a "read out" or markers of the phenotype of a particular cell.

For example, and not by way of limitation, genes, including ACTR-1, that are modulated in cells by treatment with an agent (e.g., compound, drug or small molecule) which modulates ACTR-1 activity (e.g., identified in a screening assay as described herein) can be identified. Thus, to study the effect of agents on ACTR-1-associated disorders (e.g., disorders characterized by deregulated acyltransferase activity, lipid metabolism, cellular signaling, and/or cell growth, proliferation, or differentiation mechanisms), for example, in a clinical trial, cells can be isolated and RNA prepared and analyzed for the levels of expression of ACTR-1 and other genes implicated in the ACTR-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of ACTR-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ACTR-1 protein, mRNA, or genomic DNA in the preadministration sample; (iii) obtaining one or more post-administration samples from the subject; (iv) detecting the level of expression or activity of the ACTR-1 protein, mRNA, or genomic DNA in the post-administration samples; (v) comparing the level of expression or activity of the ACTR-1 protein, mRNA, or genomic DNA in the pre-administration sample with the ACTR-1 protein, mRNA, or genomic DNA in the post administration sample or samples; and (vi) altering the administration of the agent to the subject accordingly. For example, increased administration of the agent may be desirable to increase the expression or activity of ACTR-1 to higher levels than detected, i.e., to increase the effectiveness of the agent. Alternatively, decreased administration of the agent may be desirable to decrease expression or activity of ACTR-1 to lower levels than detected, i.e. to decrease the effectiveness of the agent. According to such an embodiment, ACTR-1 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having an ACTR-1-associated disorder, e.g., a disorder associated with aberrant or unwanted ACTR-1 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the ACTR-1 molecules of the present invention or ACTR-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted ACTR-1 expression or activity, by administering to the subject an ACTR-1 or an agent which modulates ACTR-1 expression or at least one ACTR-1 activity. Subjects at risk for a disease which is caused or contributed to by aberrant or unwanted ACTR-1 expression or activity can be identified by, for example, any or a combination of diagnostic or prognostic assays as described herein. Administration of a prophylactic agent can occur prior to the manifestation of symptoms characteristic of the ACTR-1 aberrancy, such that a disease or disorder is prevented or, alternatively, delayed in its progression. Depending on the type of ACTR-1 aberrancy, for example, an ACTR-1, ACTR-1 agonist or ACTR-1 antagonist agent can be used for treating the subject. The appropriate agent can be determined based on screening assays described herein.

2. Therapeutic Methods

Another aspect of the invention pertains to methods of modulating ACTR-1 expression or activity for therapeutic purposes. Accordingly, in an exemplary embodiment, the modulatory method of the invention involves contacting a cell capable of expressing ACTR-1 with an agent that modulates one or more of the activities of ACTR-1 protein activity associated with the cell, such that ACTR-1 activity in the cell is modulated. An agent that modulates ACTR-1 protein activity can be an agent as described herein, such as a nucleic acid or a protein, a naturally-occurring target molecule of an ACTR-1 protein (e.g., an ACTR-1 substrate), an ACTR-1 antibody, an ACTR-1 agonist or antagonist, a peptidomimetic of an ACTR-1 agonist or antagonist, or other small molecule. In one embodiment, the agent stimulates one or more ACTR-1 activities. Examples of such stimulatory agents include active ACTR-1 protein and a nucleic acid molecule encoding ACTR-1 that has been introduced into the cell. In another embodiment, the agent inhibits one or more ACTR-1 activities. Examples of such inhibitory agents include anti-sense ACTR-1 nucleic acid molecules, anti-ACTR-1 antibodies, and ACTR-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an ACTR-1 protein or nucleic acid molecule. In one embodiment, the method involves administering an agent (e.g., an agent identified by a screening assay described herein), or combination of agents that modulates (e.g., upregulates or downregulates) ACTR-1 expression or activity. In another embodiment, the method involves administering an ACTR-1 protein or nucleic acid molecule as therapy to compensate for reduced, aberrant, or unwanted ACTR-1 expression or activity.

Stimulation of ACTR-1 activity is desirable in situations in which ACTR-1 is abnormally downregulated and/or in which increased ACTR-1 activity is likely to have a beneficial effect. For example, stimulation of ACTR-1 activity is desirable in situations in which an ACTR-1 is downregulated and/or in which increased ACTR-1 activity is likely to have a beneficial effect. Likewise, inhibition of ACTR-1 activity is desirable in situations in which ACTR-1 is abnormally upregulated and/or in which decreased ACTR-1 activity is likely to have a beneficial effect.

3. Pharmacogenomics

The ACTR-1 molecules of the present invention, as well as agents, or modulators which have a stimulatory or inhibitory effect on ACTR-1 activity (e.g., ACTR-1 gene expression) as identified by a screening assay described herein can be administered to individuals to treat (prophylactically or therapeutically) ACTR-1-associated disorders (e.g., disorders characterized by aberrant acyltransferase activity, a metabolic disorder, a cardiovascular disorder, or a cell proliferation, growth or differentiation disorder) associated with aberrant or unwanted ACTR-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an ACTR-1 molecule or ACTR-1 modulator as well as tailoring the dosage and/or therapeutic regimen of treatment with an ACTR-1 molecule or ACTR-1 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11):983-985 and Linder, M. W. et al. (1997) Clin. Chem. 43(2):254-266. In two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate methyltransferase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., an ACTR-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-methyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an ACTR-1 molecule or ACTR-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an ACTR-1 molecule or ACTR-1 modulator, such as a modulator identified by one of the exemplary screening assays described herein.

4. Use of ACTR-1 Molecules as Surrogate Markers

The ACTR-1 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the ACTR-1 molecules of the invention may be detected, and may be correlated with one or more biological states in vivo. For example, the ACTR-1 molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

The ACTR-1 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an ACTR-1 marker) transcription or expression, the amplified marker may be in a quantity which is more readily detectable than the drug itself. Also, the marker may be more easily detected due to the nature of the marker itself; for example, using the methods described herein, anti-ACTR-1 antibodies may be employed in an immune-based detection system for an ACTR-1 protein marker, or ACTR-1-specific radiolabeled probes may be used to detect an ACTR-1 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3:S21-S24; and Nicolau (1999) *Am. J. Health-Syst. Pharm.* 56 Suppl. 3:S21-S24; and Nicolau (1999) *Am. J. Health-Syst. Pharm.* 56 *Suppl.* 3:S16-S20.

The ACTR-1 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., ACTR-1 protein or RNA) for specific tumor markers in a subject, a drug or course of treatment may be selected that is optimized for the treatment of the specific tumor likely to be present in the subject. Similarly, the presence or absence of a specific sequence mutation in ACTR-1 DNA may correlate ACTR-1 drug response. The use of pharmacogenomic markers therefore permits the application of the most appropriate treatment for each subject without having to administer the therapy.

5. Electronic Apparatus Readable Media and Arrays

Electronic apparatus readable media comprising ACTR-1 sequence information is also provided. As used herein, "ACTR-1 sequence information" refers to any nucleotide and/or amino acid sequence information particular to the ACTR-1 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said ACTR-1 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon ACTR-1 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the ACTR-1 sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the ACTR-1 sequence information.

By providing ACTR-1 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a ACTR-1 associated disease or disorder or a pre-disposition to a ACTR-1 associated disease or disorder, wherein the method comprises the steps of determining ACTR-1 sequence information associated with the subject and based on the ACTR-1 sequence information, determining whether the subject has a ACTR-1 associated disease or disorder or a pre-disposition to a ACTR-1 associated disease or disorder, and/or recommending a particular treatment for the disease, disorder, or pre-disease condition.

The present invention further provides in an electronic system and/or in a network, a method for determining whether a subject has a ACTR-1 associated disease or disorder or a pre-disposition to a disease associated with ACTR-1 wherein the method comprises the steps of determining ACTR-1 sequence information associated with the subject, and based on the ACTR-1 sequence information, determining whether the subject has a ACTR-1 associated disease or disorder or a pre-disposition to a ACTR-1 associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a ACTR-1 associated disease or disorder or a pre-disposition to a ACTR-1 associated disease or disorder associated with ACTR-1, said method comprising the steps of receiving ACTR-1 sequence information from the subject and/or information related thereto, receiving phenotypic information associated with the subject, acquiring information from the network corresponding to ACTR-1 and/or a ACTR-1 associated disease or disorder, and based on one or more of the phenotypic information, the ACTR-1 information (e.g., sequence information and/or information related thereto), and the acquired information, determining whether the subject has a ACTR-1 associated disease or disorder or a pre-disposition to a ACTR-1 associated disease or disorder. The method may further comprise the step of recommending a particular treatment for the disease, disorder or pre-disease condition.

The present invention also provides a business method for determining whether a subject has a ACTR-1 associated disease or disorder or a pre-disposition to a ACTR-1 associated disease or disorder, said method comprising the steps of receiving information related to ACTR-1 (e.g., sequence information and/or information related thereto), receiving phenotypic information associated with the subject, acquiring information from the network related to ACTR-1 and/or related to a ACTR-1 associated disease or disorder, and based on one or more of the phenotypic information, the ACTR-1 information, and the acquired information, determining whether the subject has a ACTR-1 associated disease or disorder or a pre-disposition to a ACTR-1 associated disease or disorder. The method may further comprise the step of recommending a particular treatment for the disease, disorder or pre-disease condition.

The invention also includes an array comprising a ACTR-1 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be ACTR-1. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a ACTR-1 associated disease or disorder, progression of ACTR-1 associated disease or disorder, and processes, such a cellular transformation associated with the ACTR-1 associated disease or disorder.

The array is also useful for ascertaining the effect of the expression of a gene on the expression of other genes in the same cell or in different cells (e.g., ascertaining the effect of ACTR-1 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including ACTR-1) that could serve as a molecular target for diagnosis or therapeutic intervention.

This invention is further illustrated by the following examples which should not be construed as limiting. The contents of all references, patents and published patent applications cited throughout this application, as well as the figures and the appendices, are incorporated herein by reference.

EXAMPLES

Example 1

Identification and Characterization of Human ACTR-1 cDNA

In this example, the identification and characterization of the gene encoding human ACTR-1 (also referred to interchangeably as "clone 56919" or "human GPAT", herein) is described.

Isolation of the Human ACTR-1 cDNA

The invention is based, at least in part, on the discovery of genes encoding novel members of the acyltransferase family. The entire sequence of human clone 56919 was determined and found to contain an open reading frame termed human "ACTR-1".

The nucleotide sequence encoding the human ACTR-1 is shown in FIG. 1 and is set forth as SEQ ID NO:1. The protein encoded by this nucleic acid comprises about 828 amino acids and has the amino acid sequence shown in FIG. 1 and set forth as SEQ ID NO:2. The coding region (open reading frame) of SEQ ID NO:1 is set forth as SEQ ID NO:3.

Analysis of the Human ACTR-1 Molecules

Homology searching using the amino acid and/or nucleotide sequence of human ACTR-1 revealed that the protein was significantly homologous (92%) to murine mitochondrial GPAT indicating that clone 56919 represents the human mitochondrial GPAT gene. Mitochondrial GPAT (mGPAT) catalyzes the initial step in the biosynthesis of triglycerides. Triglycerides have been identified as independent risk factor for the development of atherosclerosis. Inhibitors of rodent mGPAT (endogenous and small molecules) have been described in the literature to exhibit triglyceride-lowering effects in vivo. Thus, human mGPAT is predicted to play a pivotal role in the regulation of triglyceride biosynthesis/metabolism in humans. Moreover, inhibition of human mitochondrial GPAT is predicted to result in decreased levels of serum triglyceride, which in turn will be beneficial in the treatment of atherosclerosis.

The amino acid sequence of human ACTR-1 was analyzed using the program PSORT to predict the localization of the proteins within the cell. This program assesses the presence of different targeting and localization amino acid sequences within the query sequence. The results of the analyses show that human ACTR-1 may be localized to the nucleus, to the mitochondria, or to the cytoplasm. Based on homology to mouse and rat GPATS, human ACTR-1 is believed to be mitochondrial.

Analysis of the amino acid sequence of human ACTR-1 was performed using MEMSAT. This analysis resulted in the identification of transmembrane domains in the amino acid sequence of human ACTR-1 at residues 177-194, 330-354, 472-494 and 576-594 of SEQ ID NO:2.

Searches of the amino acid sequence of human ACTR-1 were also performed against the HMM database (FIG. 3). These searches resulted in the identification of a "acyltransferase domain" at about residues 215-412 of SEQ ID NO:2 (score=126.1).

Searches of the amino acid sequence of human ACTR-1 were further performed against the Prosite database, and resulted in the identification of several possible phosphorylation sites within the amino acid sequence of human ACTR-1 (SEQ ID NO:2). Protein kinase C phosphorylation sites were identified at residues 48-50, 57-59, 136-138, 321-323, 405-407, 414-416, 459-461, 549-551, 685-687 and 763-765; cAMP and cGMP dependent protein kinase phosphorylation sites were identified at residues 107-110 and 798-801; casein kinase II phosphorylation sites were identified at residues 30-33, 232-235, 405-408, 448-451, 504-507, 550-553, 565-568, 657-660, 670-673, 688-691, 761-764 and 801-804; and a tyrosine kinase phosphorylation site was identified at residues 358-364 of human ACTR-1. The search also identified the presence of N-glycosylation site motifs at amino acid residues 95-98, 128-131, 135-138, 375-378, 450-453, 454-457 and 741-744; N-myristoylation site motifs at amino acid residues 123-128, 256-261, 499-504, 541-546 and 600-605; and an amidation site at amino acid residues 285-288 of human ACTR-1.

A search of the amino acid sequence of human ACTR-1 performed against the ProDom database results in the local alignment of the human ACTR-1 protein various known with glycerol-3-phosphate acyltransferase proteins (FIG. 4).

Tissue Distribution of ACTR-1 mRNA

This example describes the tissue distribution of ACTR-1 mRNA, as may be determined using in situ hybridization anaylsis. For in situ analysis, various tissues, e.g. human or mouse tissue samples, are first frozen on dry ice. Ten-micrometer-thick sections of the tissues are postfixed with 4% formaldehyde in DEPC-treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15 M NaCl plus 0.015 M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5 \times 10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 2

Expression of Recombinant ACTR-1 Protein in Bacterial Cells

In this example, human ACTR-1 is expressed as a recombinant glutathione-S-transferase (GST) fusion polypeptide in E. coli and the fusion polypeptide is isolated and characterized. Specifically, human ACTR-1 is fused to GST and this fusion polypeptide is expressed in E. coli, e.g., strain PEB199. Expression of the GST-ACTR-1 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant ACTR-1 Protein in COS Cells

To express the ACTR-1 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire ACTR-1 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the ACTR-1 DNA sequence is amplified by PCR using two primers. The 5' primer contains the restriction site of interest followed by approximately twenty nucleotides of the ACTR-1 coding sequence starting from the initiation codon; the 3' end sequence contains complementary sequences to the other restriction site of interest, a translation stop codon, the HA tag or FLAG tag and the last 20 nucleotides of the ACTR-1 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the ACTR-1 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the ACTR-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* $2^{nd}$, ed., Cold Spring Harbor Laboratory, Cold Spring Harbor Laboratory Press, Cold Spring Harbor, N.Y., 1989. The expression of the ACTR-1 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the ACTR-1 coding sequence is cloned directly into the polylinker of the pCDNA/Amp vector using the appropriate restriction sites. The resulting plasmid is transfected into COS cells in the manner described above, and the expression of the ACTR-1 polypeptide is detected by radiolabelling and immunoprecipitation using an ACTR-1 specific monoclonal antibody.

Example 4

Tissue Distribution of Human ACTR-1 mRNA Using TAQMAN™ Analysis

This example describes the tissue distribution of human ACTR-1 mRNA in a variety of cells and tissues, as determined using the TAQMAN™ procedure. The TAQMAN™ procedure is a quantitative, reverse transcription PCR-based approach for detecting mRNA. The RT-PCR reaction exploits the 5' nuclease activity of AMPLITAQ GOLD™ DNA Polymerase to cleave a TAQMAN™ probe during PCR. Briefly, cDNA was generated from the samples of interest, e.g., various human tissue samples, and used as the starting material for PCR amplification. In addition to the 5' and 3' gene-specific primers, a gene-specific oligonucleotide probe (complementary to the region being amplified) was included in the reaction (i.e., the TAQMAN™ probe). The TAQMAN™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AMPLITAQ™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Figure 8A:
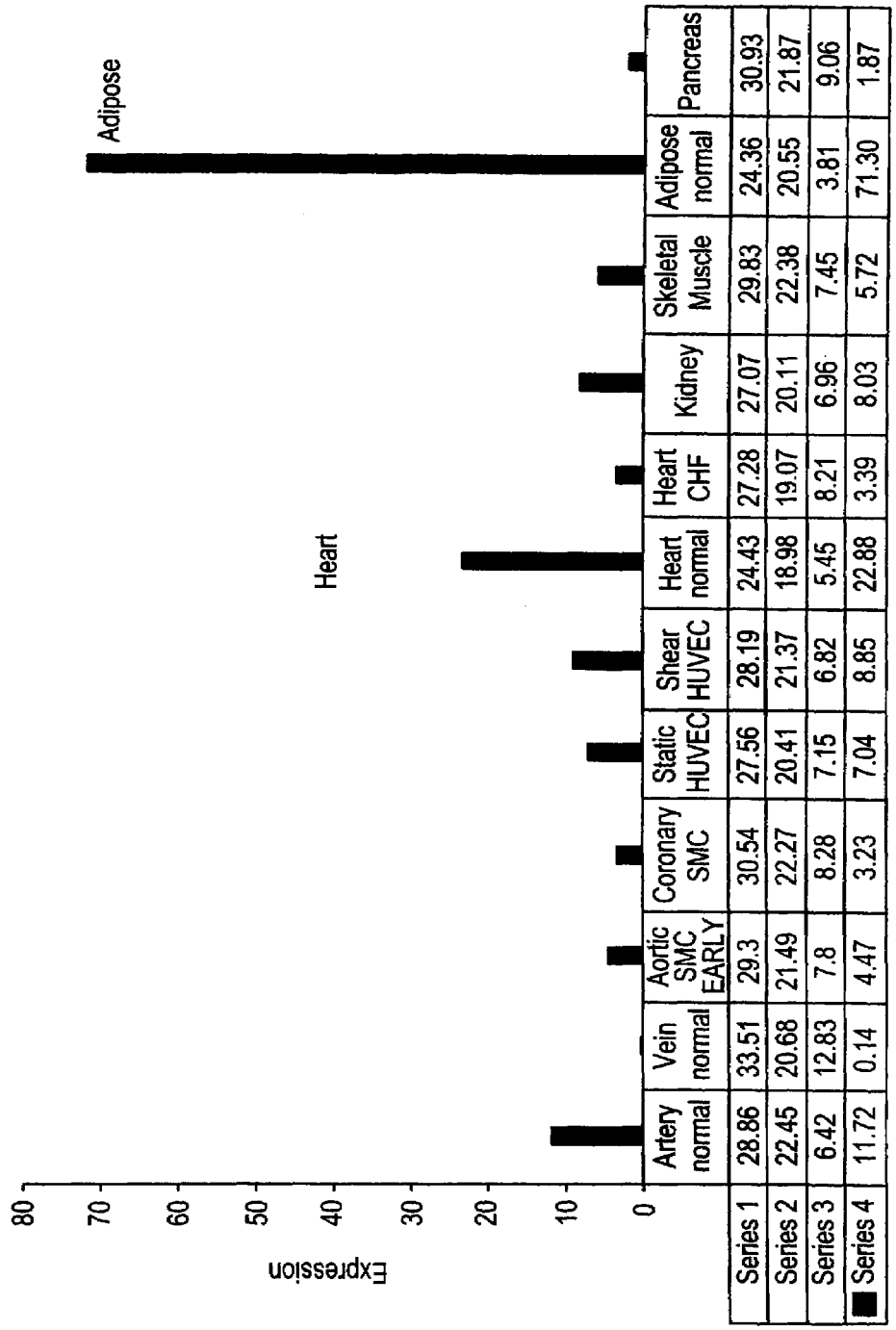
Figure 8B:
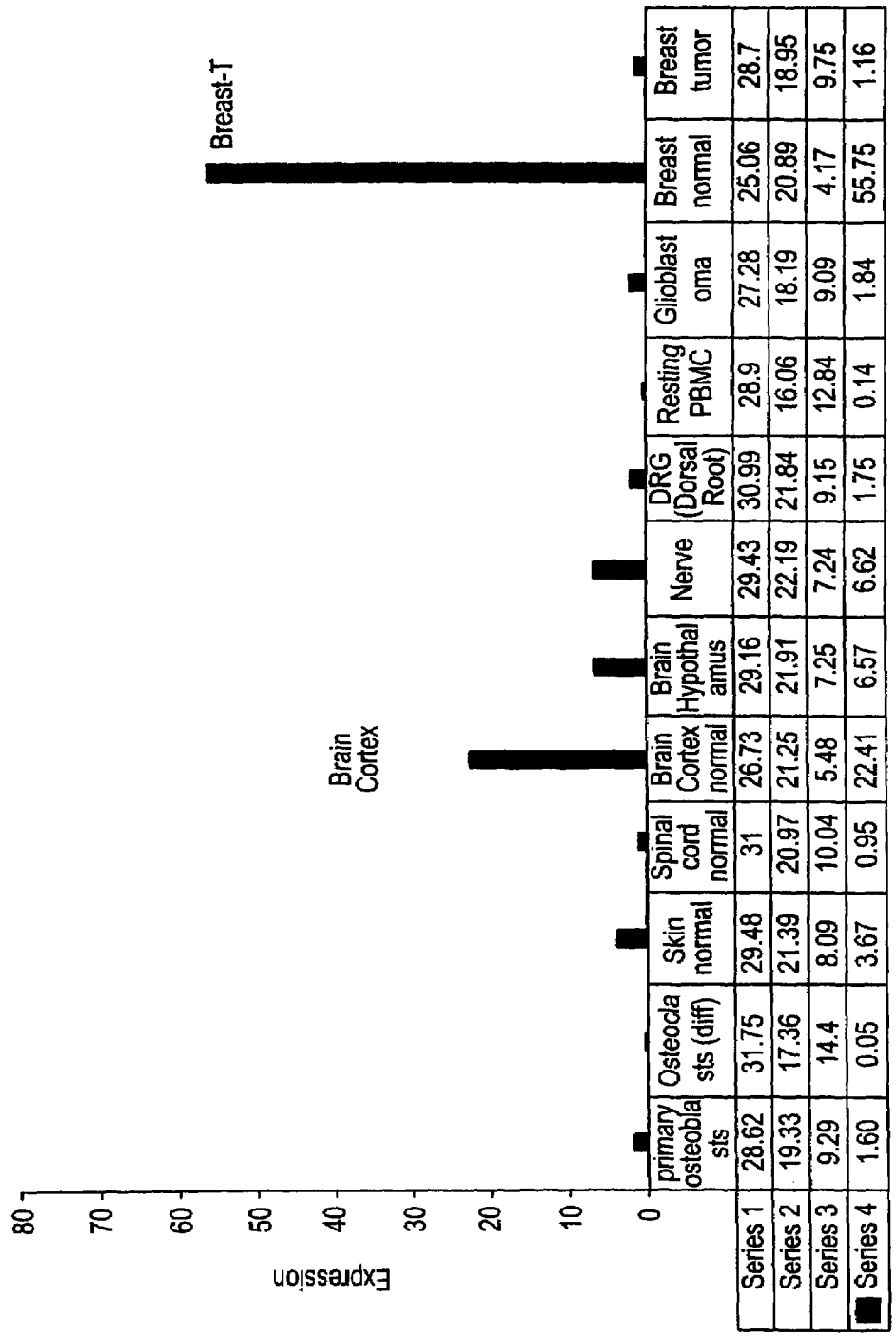
Figure 8D:
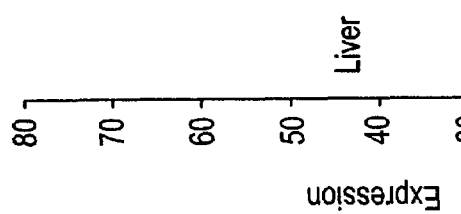
Figure 9A:
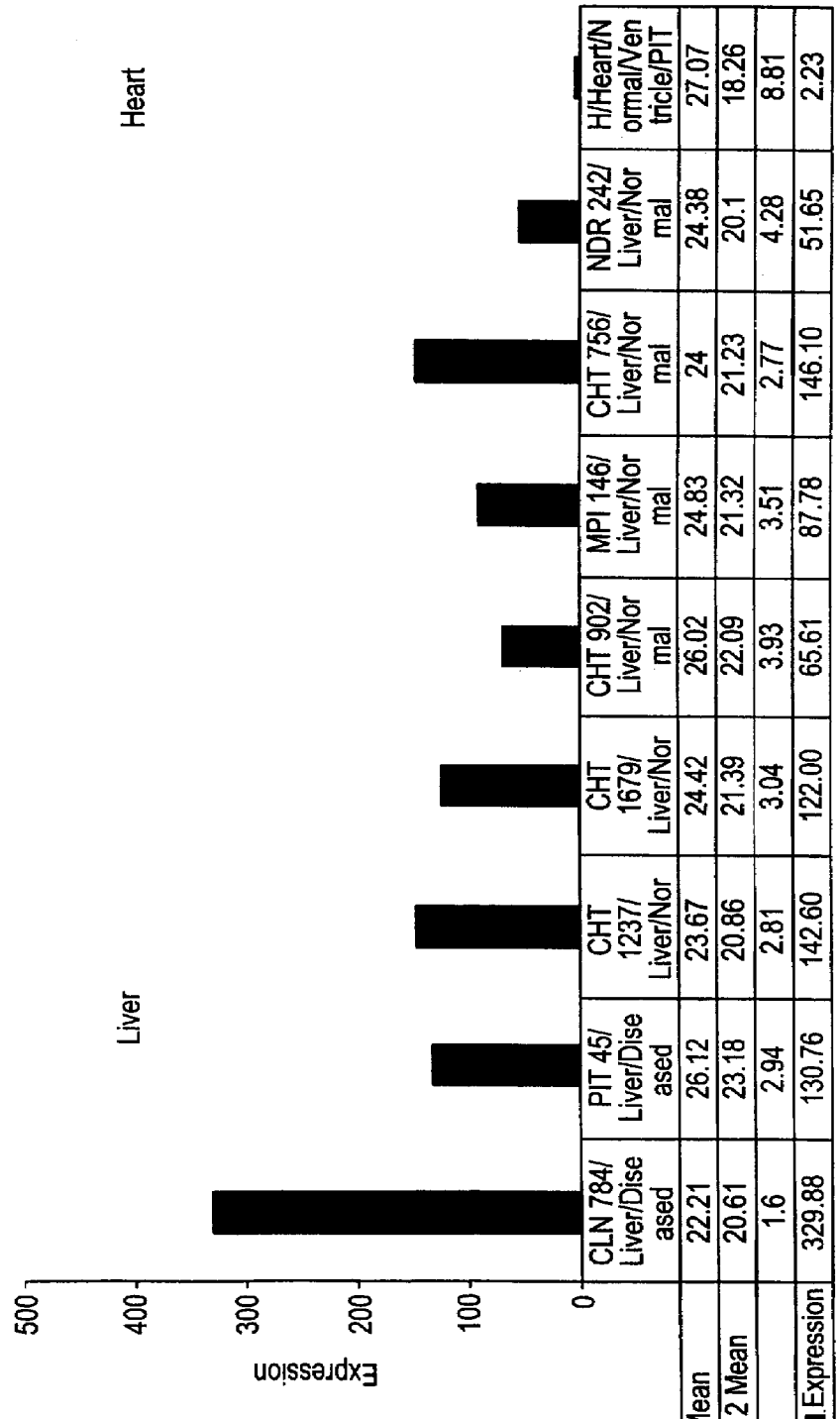
Figure 9B:
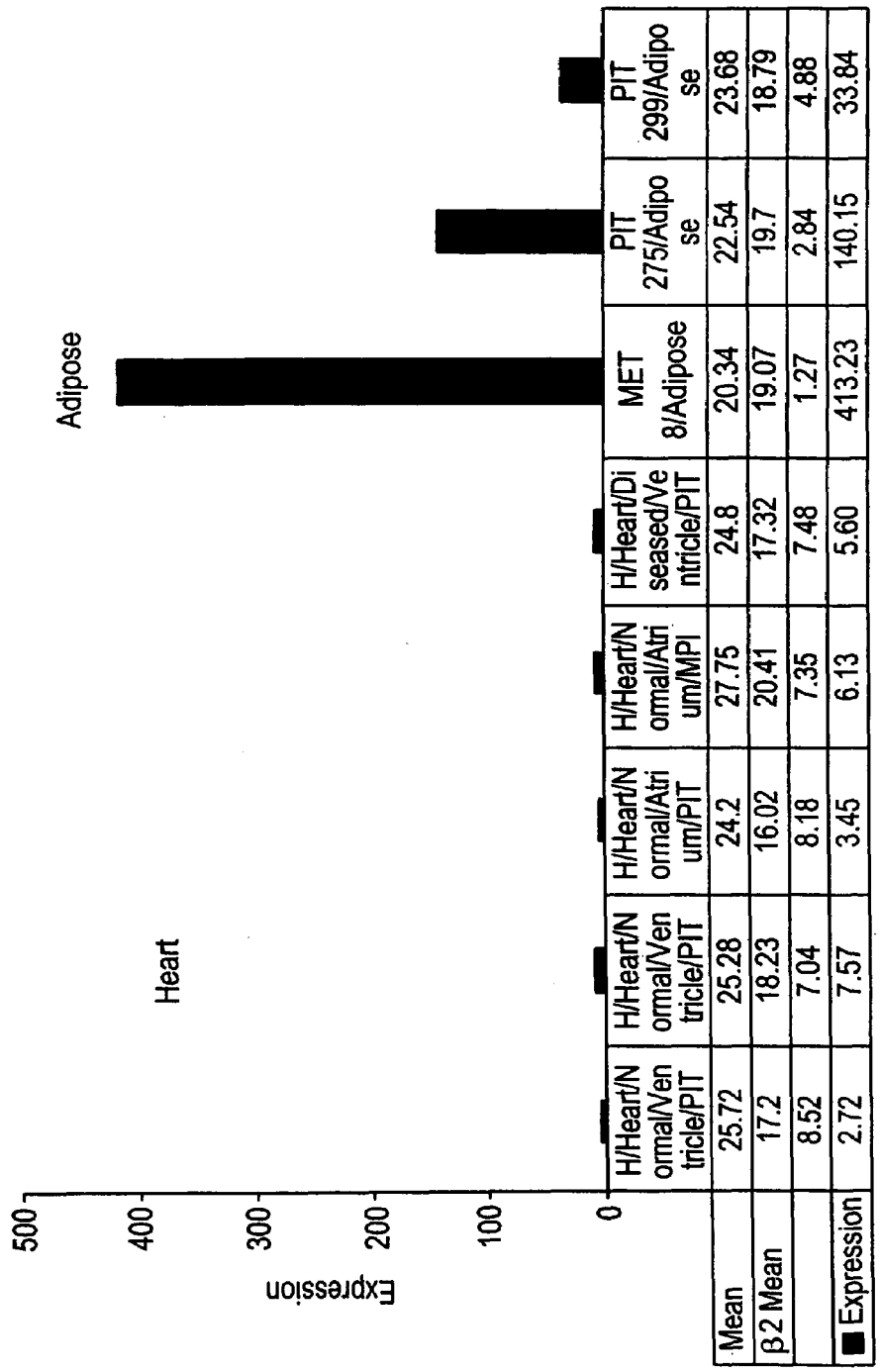

As indicated in FIGS. 7 and 8, strong expression of ACTR-1 was detected in the normal liver, adipose, heart and brain tissues. Moreover, as indicated in FIG. 9, strong expression of the ACTR-1 was detected across a broad panel of human liver tissue samples.

Example 5

Upregulation of ACTR-1 in an In Vivo Marmoset Cholestyramine Model

Figure 10A:
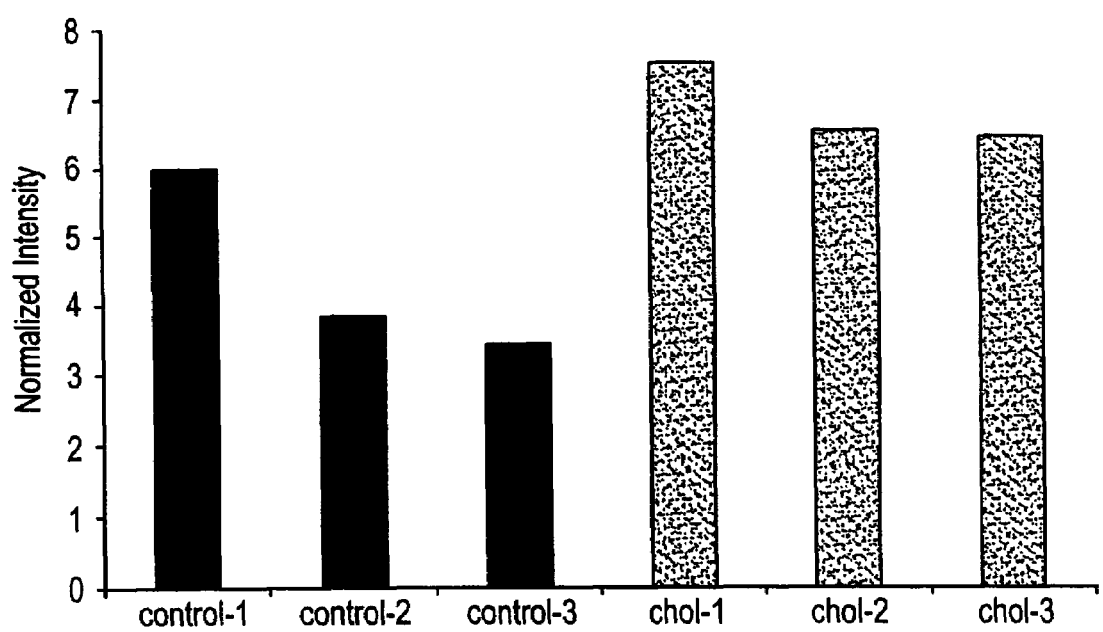
FIG. 10A is a graph depicting cholestyramine regulation of ACTR-1 expression in a marmoset animal model.
Figure 10B:
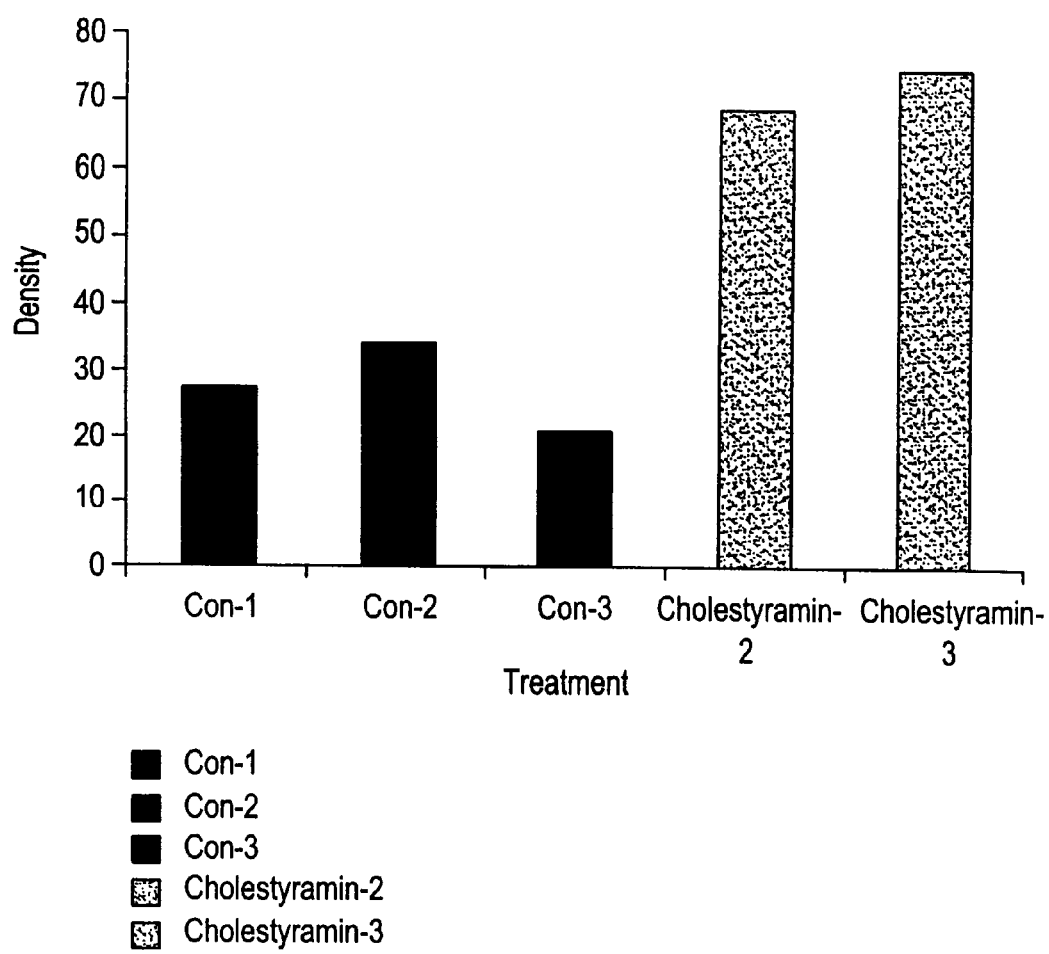
FIG. 10B is a graph depicting the results of a slot blot validation of cholestyramine regulation of ACTR-1 in the marmoset animal model.

In addition to bioinformatic analysis, TxP studies indicate that MINE 56919 is upregulated in the in vivo marmoset cholestyramine model (FIGS. 10 A and B). Cholestyramine is a current therapy for the treatment of hypercholesterolemia. Cholesteryamine is a soluble resin that acts by sequestering bile acid and promoting its excretion from the body. This results in the increased conversion of cholesterol to bile acid with the ultimate benefit of decreasing total serum cholesterol (TC). However, it has been shown that short-term cholestyramine treatment results in elevated serum triglyceride levels (Garg A, Grundy S M. (1994) *Ann Intern Med* 121:416-22; Kuroki S et al., (1999) *Lipids* 34:817-23). The induction of 56919, the predicted human mGPAT, in the marmoset cholestyramine model is consistent with this gene playing a key role in the regulation of triglyceride biosynthesis.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated polypeptide selected from the group consisting of:
   a) a polypeptide comprising the amino acid sequence of SEQ ID) NO:2; and
   b) a polypeptide encoded by a nucleic acid comprising the nucleotide sequence of SEQ ID NO:1 or SEQ ID NO:3.

2. The isolated polypeptide of claim 1 comprising the amino acid sequence of SEQ ID) NO:2.

3. The polypeptide of claim 1 further comprising heterologous amino acid sequences.

4. The polypeptide of claim 1, wherein the polypeptide is encoded by a nucleic acid comprising the nucleotide sequence of SEQ ID NO:1 or SEQ ID NO:3.

5. The polypeptide of claim 1, wherein the polypeptide consists of the amino acid sequence of SEQ ID) NO:2.

6. The polypeptide of claim 1, wherein the polypeptide is encoded by a nucleic acid consisting of the nucleotide sequence of SEQ ID NO:1 or SEQ ID NO:3.

7. The polypeptide of claim 2, further comprising heterologous amino acid sequences.

8. The polypeptide of claim 4, further comprising heterologous amino acid sequences.

* * * * *

SEQUENCE LISTING

```
<160> NUMBER OF SEQ ID NOS: 16

<210> SEQ ID NO 1
<211> LENGTH: 3003
<212> TYPE: DNA
<213> ORGANISM: Homo sapiens
<220> FEATURE:
<221> NAME/KEY: CDS
<222> LOCATION: (341)...(2827)
<220> FEATURE:
<221> NAME/KEY: misc_feature
<222> LOCATION: 2939, 2973
<223> OTHER INFORMATION: n = A,T,C or G

<400> SEQUENCE: 1
ttcggcacca ggctgctgcg gggggactct ttctgaggtt actgtggagc acccaaagtc      60
tgtcagcctc tggccgtgca aacaggcacc cagaggaacc agaccttgct tattcaccca     120
cagcctggga ctgtcttctc cagagtctcc atcagctttg ctaatcgact gattggaaat     180
aattcctcaa acaccaccaa gtcaaggata caggcagcag cggctcccct gttgtatgga     240
cattctgcac ccgaaactga tagctgagtc ctgaagtttt atgttatgaa acagaagaac     300
tttcatccca gcacatgatt tgggaattac actttgtgac atg gat gaa tct gca      355
                                              Met Asp Glu Ser Ala
                                              1               5 ctg acc ctt ggt aca ata gat gtt tct tat ctg cca cat tca tca gaa      403
Leu Thr Leu Gly Thr Ile Asp Val Ser Tyr Leu Pro His Ser Ser Glu
               10                  15                  20 tac agt gtt ggt cga tgt aag cac aca agt gag gaa tgg ggt gag tgt      451
Tyr Ser Val Gly Arg Cys Lys His Thr Ser Glu Glu Trp Gly Glu Cys
           25                  30                  35 ggc ttt aga ccc acc gtc ttc aga tct gca act tta aaa tgg aaa gaa      499
Gly Phe Arg Pro Thr Val Phe Arg Ser Ala Thr Leu Lys Trp Lys Glu
       40                  45                  50 agc cta atg agt cgg aaa agg cca ttt gtt gga aga tgt tgt tac tcc      547
Ser Leu Met Ser Arg Lys Arg Pro Phe Val Gly Arg Cys Cys Tyr Ser
   55                  60                  65 tgc act ccc cag agc tgg gac aaa ttt ttc aac ccc agt atc ccg tct      595
Cys Thr Pro Gln Ser Trp Asp Lys Phe Phe Asn Pro Ser Ile Pro Ser
70                  75                  80                  85 ttg ggt ttg cgg aat gtt att tat atc aat gaa act cac aca aga cac      643
Leu Gly Leu Arg Asn Val Ile Tyr Ile Asn Glu Thr His Thr Arg His
               90                  95                 100 cgc gga tgg ctt gca aga cgc ctt tct tac gtt ctt ttt att caa gag      691
Arg Gly Trp Leu Ala Arg Arg Leu Ser Tyr Val Leu Phe Ile Gln Glu
           105                 110                 115
```

```
cga gat gtg cat aag ggc atg ttt gcc acc aat gtg act gaa aat gtg    739
Arg Asp Val His Lys Gly Met Phe Ala Thr Asn Val Thr Glu Asn Val
        120                 125                 130 ctg aac agc agt aga gta caa gag gca att gca gaa gtg gct gct gaa    787
Leu Asn Ser Ser Arg Val Gln Glu Ala Ile Ala Glu Val Ala Ala Glu
    135                 140                 145 tta aac cct gat ggt tct gcc cag cag caa tca aaa gcc gtt aac aaa    835
Leu Asn Pro Asp Gly Ser Ala Gln Gln Gln Ser Lys Ala Val Asn Lys
150                 155                 160                 165 gtg aaa aag aaa gct aaa agg att ctt caa gaa atg gtt gcc act gtc    883
Val Lys Lys Lys Ala Lys Arg Ile Leu Gln Glu Met Val Ala Thr Val
            170                 175                 180 tca ccg gca atg atc aga ctg act ggg tgg gtg ctg cta aaa ctg ttc    931
Ser Pro Ala Met Ile Arg Leu Thr Gly Trp Val Leu Leu Lys Leu Phe
                185                 190                 195 aac agc ttc ttt tgg aac att caa att cac aaa ggt caa ctt gag atg    979
Asn Ser Phe Phe Trp Asn Ile Gln Ile His Lys Gly Gln Leu Glu Met
            200                 205                 210 gtt aaa gct gca act gag acg aat ttg ccg ctt ctg ttt cta cca gtt   1027
Val Lys Ala Ala Thr Glu Thr Asn Leu Pro Leu Leu Phe Leu Pro Val
    215                 220                 225 cat aga tcc cat att gac tat ctg ctg ctc act ttc att ctc ttc tgc   1075
His Arg Ser His Ile Asp Tyr Leu Leu Leu Thr Phe Ile Leu Phe Cys
230                 235                 240                 245 cat aac atc aaa gca cca tac att gct tca ggc aat aat ctc aac atc   1123
His Asn Ile Lys Ala Pro Tyr Ile Ala Ser Gly Asn Asn Leu Asn Ile
            250                 255                 260 cca atc ttc agt acc ttg atc cat aag ctt ggg ggc ttc ttc ata cga   1171
Pro Ile Phe Ser Thr Leu Ile His Lys Leu Gly Gly Phe Phe Ile Arg
                265                 270                 275 cga agg ctc gat gaa aca cca gat gga cgg aaa gat gtt ctc tat aga   1219
Arg Arg Leu Asp Glu Thr Pro Asp Gly Arg Lys Asp Val Leu Tyr Arg
            280                 285                 290 gct ttg ctc cat ggg cat ata gtt gaa tta ctt cga cag cag caa ttc   1267
Ala Leu Leu His Gly His Ile Val Glu Leu Leu Arg Gln Gln Gln Phe
    295                 300                 305 ttg gag atc ttc ctg gaa ggc aca cgt tct agg agt gga aaa acc tct   1315
Leu Glu Ile Phe Leu Glu Gly Thr Arg Ser Arg Ser Gly Lys Thr Ser
310                 315                 320                 325 tgt gct cgg gca gga ctt ttg tca gtt gtg gta gat act ctg tct acc   1363
Cys Ala Arg Ala Gly Leu Leu Ser Val Val Val Asp Thr Leu Ser Thr
            330                 335                 340 aat gtc atc cca gac atc ttg ata ata cct gtt gga atc tcc tat gat   1411
Asn Val Ile Pro Asp Ile Leu Ile Ile Pro Val Gly Ile Ser Tyr Asp
                345                 350                 355 cgc att atc gaa ggt cac tac aat ggt gaa caa ctg ggc aaa cct aag   1459
Arg Ile Ile Glu Gly His Tyr Asn Gly Glu Gln Leu Gly Lys Pro Lys
            360                 365                 370 aag aat gag agc ctg tgg agt gta gca aga ggt gtt att aga atg tta   1507
Lys Asn Glu Ser Leu Trp Ser Val Ala Arg Gly Val Ile Arg Met Leu
    375                 380                 385 cga aaa aac tat ggt tgt gtc cga gtg gat ttt gca cag cca ttt tcc   1555
Arg Lys Asn Tyr Gly Cys Val Arg Val Asp Phe Ala Gln Pro Phe Ser
390                 395                 400                 405 tta aag gaa tat tta gaa agc caa agt cag aaa ccg gtg tct gct cta   1603
Leu Lys Glu Tyr Leu Glu Ser Gln Ser Gln Lys Pro Val Ser Ala Leu
            410                 415                 420 ctt tcc ctg gag caa gcg ttg tta cca gct ata ctt cct tca aga ccc   1651
Leu Ser Leu Glu Gln Ala Leu Leu Pro Ala Ile Leu Pro Ser Arg Pro
```

-continued

```
                425                     430                     435
agt gat gct gct gat gaa ggt aga gac acg tcc att aat gag tcc aga      1699
Ser Asp Ala Ala Asp Glu Gly Arg Asp Thr Ser Ile Asn Glu Ser Arg
            440                     445                     450 aat gca aca gat gaa tcc cta cga agg agg ttg att gca aat ctg gct      1747
Asn Ala Thr Asp Glu Ser Leu Arg Arg Arg Leu Ile Ala Asn Leu Ala
    455                     460                     465 gag cat att cta ttc act gct agc aag tcc tgt gcc att atg tcc aca      1795
Glu His Ile Leu Phe Thr Ala Ser Lys Ser Cys Ala Ile Met Ser Thr
470                     475                     480                     485 cac att gtg gct tgc ctg ctc ctc tac aga cac agg cag gga att gat      1843
His Ile Val Ala Cys Leu Leu Leu Tyr Arg His Arg Gln Gly Ile Asp
                490                     495                     500 ctc tcc aca ttg gtc gaa gac ttc ttt gtg atg aaa gag gaa gtc ctg      1891
Leu Ser Thr Leu Val Glu Asp Phe Phe Val Met Lys Glu Glu Val Leu
        505                     510                     515 gct cgt gat ttt gac ctg ggg ttc tca gga aat tca gaa gat gta gta      1939
Ala Arg Asp Phe Asp Leu Gly Phe Ser Gly Asn Ser Glu Asp Val Val
    520                     525                     530 atg cat gcc ata cag ctg ctg gga aat tgt gtc aca atc acc cac act      1987
Met His Ala Ile Gln Leu Leu Gly Asn Cys Val Thr Ile Thr His Thr
535                     540                     545 agc agg aac gat gag ttt ttt atc acc ccc agc aca act gtc cca tca      2035
Ser Arg Asn Asp Glu Phe Phe Ile Thr Pro Ser Thr Thr Val Pro Ser
550                     555                     560                     565 gtc ttc gaa ctc aac ttc tac agc aat ggg gta ctt cat gtc ttt atc      2083
Val Phe Glu Leu Asn Phe Tyr Ser Asn Gly Val Leu His Val Phe Ile
                570                     575                     580 atg gag gcc atc ata gct tgc agc ctt tat gca gtt ctg aac aag agg      2131
Met Glu Ala Ile Ile Ala Cys Ser Leu Tyr Ala Val Leu Asn Lys Arg
        585                     590                     595 gga ctg ggg ggt ccc act agc acc cca cct aac ctg atc agc cag gag      2179
Gly Leu Gly Gly Pro Thr Ser Thr Pro Pro Asn Leu Ile Ser Gln Glu
    600                     605                     610 cag ctg gtg cgg aag gcg gcc agc ctg tgc tac ctt ctc tcc aat gaa      2227
Gln Leu Val Arg Lys Ala Ala Ser Leu Cys Tyr Leu Leu Ser Asn Glu
615                     620                     625 ggc acc atc tca ctg cct tgc cag aca ttt tac caa gtc tgc cat gaa      2275
Gly Thr Ile Ser Leu Pro Cys Gln Thr Phe Tyr Gln Val Cys His Glu
630                     635                     640                     645 aca gta gga aag ttt atc cag tat ggc att ctt aca gtg gca gag cac      2323
Thr Val Gly Lys Phe Ile Gln Tyr Gly Ile Leu Thr Val Ala Glu His
                650                     655                     660 gat gac cag gaa gat atc agt cct agt ctt gct gag cag cag tgg gac      2371
Asp Asp Gln Glu Asp Ile Ser Pro Ser Leu Ala Glu Gln Gln Trp Asp
        665                     670                     675 aag aag ctt cca gaa cct ttg tct tgg aga agt gat gaa gat gaa          2419
Lys Lys Leu Pro Glu Pro Leu Ser Trp Arg Ser Asp Glu Glu Asp Glu
    680                     685                     690 gac agt gac ttt ggg gag gaa cag cga gat tgc tac ctg aag gtg agc      2467
Asp Ser Asp Phe Gly Glu Glu Gln Arg Asp Cys Tyr Leu Lys Val Ser
695                     700                     705 caa tcc aag gag cac cag cag ttt atc acc ttc tta cag aga ctc ctt      2515
Gln Ser Lys Glu His Gln Gln Phe Ile Thr Phe Leu Gln Arg Leu Leu
710                     715                     720                     725 ggg cct ttg ctg gag gcc tac agc tct gct gcc atc ttt gtt cac aac      2563
Gly Pro Leu Leu Glu Ala Tyr Ser Ser Ala Ala Ile Phe Val His Asn
                730                     735                     740 ttc agt ggt cct gtt cca gaa cct gag tat ctg caa aag ttg cac aaa      2611
```

```
                Phe Ser Gly Pro Val Pro Glu Pro Glu Tyr Leu Gln Lys Leu His Lys
                            745                 750                 755 tac cta ata acc aga aca gaa aga aat gtt gca gta tat gct gag agt           2659
Tyr Leu Ile Thr Arg Thr Glu Arg Asn Val Ala Val Tyr Ala Glu Ser
            760                 765                 770 gcc aca tat tgt ctt gtg aag aat gct gtg aaa atg ttt aag gat att           2707
Ala Thr Tyr Cys Leu Val Lys Asn Ala Val Lys Met Phe Lys Asp Ile
        775                 780                 785 ggg gtt ttc aag gag acc aaa caa aag aga gtg tct gtt tta gaa ctg           2755
Gly Val Phe Lys Glu Thr Lys Gln Lys Arg Val Ser Val Leu Glu Leu
790                 795                 800                 805 agc agc act ttt cta cct caa tgc aac cga caa aaa ctt cta gaa tat           2803
Ser Ser Thr Phe Leu Pro Gln Cys Asn Arg Gln Lys Leu Leu Glu Tyr
                810                 815                 820 att ctg agt ttt gtg gtg ctg tag gtaacgtgtg cactgctgg caaatgaagg           2857
Ile Leu Ser Phe Val Val Leu  *
                825 tcatgagatg agttccttgt aggtaccagc ttctggctca agagtttgaa ggtgccttcg         2917 cagggggtcag gcctgccctg tnccgaagtg atctcctgga agacaagtgc cttctncctc        2977 catggatctg agatcttccc agcttt                                              3003

<210> SEQ ID NO 2
<211> LENGTH: 828
<212> TYPE: PRT
<213> ORGANISM: Homo sapiens

<400> SEQUENCE: 2

Met Asp Glu Ser Ala Leu Thr Leu Gly Thr Ile Asp Val Ser Tyr Leu
  1               5                  10                  15

Pro His Ser Ser Glu Tyr Ser Val Gly Arg Cys Lys His Thr Ser Glu
                 20                  25                  30

Glu Trp Gly Glu Cys Gly Phe Arg Pro Thr Val Phe Arg Ser Ala Thr
             35                  40                  45

Leu Lys Trp Lys Glu Ser Leu Met Ser Arg Lys Arg Pro Phe Val Gly
         50                  55                  60

Arg Cys Cys Tyr Ser Cys Thr Pro Gln Ser Trp Asp Lys Phe Phe Asn
 65                  70                  75                  80

Pro Ser Ile Pro Ser Leu Gly Leu Arg Asn Val Ile Tyr Ile Asn Glu
                 85                  90                  95

Thr His Thr Arg His Arg Gly Trp Leu Ala Arg Arg Leu Ser Tyr Val
            100                 105                 110

Leu Phe Ile Gln Glu Arg Asp Val His Lys Gly Met Phe Ala Thr Asn
        115                 120                 125

Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Ser
145                 150                 155                 160

Lys Ala Val Asn Lys Val Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220
```

```
Leu Phe Leu Pro Val His Arg Ser His Ile Asp Tyr Leu Leu Thr
225                 230                 235                 240

Phe Ile Leu Phe Cys His Asn Ile Lys Ala Pro Tyr Ile Ala Ser Gly
            245                 250                 255

Asn Asn Leu Asn Ile Pro Ile Phe Ser Thr Leu Ile His Lys Leu Gly
                260                 265                 270

Gly Phe Phe Ile Arg Arg Leu Asp Glu Thr Pro Asp Gly Arg Lys
            275                 280                 285

Asp Val Leu Tyr Arg Ala Leu Leu His Gly His Ile Val Glu Leu Leu
        290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430

Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
        530                 535                 540

Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
        610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
```

```
                    645                 650                 655
Thr Val Ala Glu His Asp Asp Gln Glu Asp Ile Ser Pro Ser Leu Ala
                660                 665                 670
Glu Gln Gln Trp Asp Lys Lys Leu Pro Glu Pro Leu Ser Trp Arg Ser
            675                 680                 685
Asp Glu Glu Asp Glu Asp Ser Asp Phe Gly Glu Gln Arg Asp Cys
        690                 695                 700
Tyr Leu Lys Val Ser Gln Ser Lys Glu His Gln Gln Phe Ile Thr Phe
705                 710                 715                 720
Leu Gln Arg Leu Leu Gly Pro Leu Leu Glu Ala Tyr Ser Ser Ala Ala
                725                 730                 735
Ile Phe Val His Asn Phe Ser Gly Pro Val Pro Glu Pro Glu Tyr Leu
                740                 745                 750
Gln Lys Leu His Lys Tyr Leu Ile Thr Arg Thr Glu Arg Asn Val Ala
            755                 760                 765
Val Tyr Ala Glu Ser Ala Thr Tyr Cys Leu Val Lys Asn Ala Val Lys
770                 775                 780
Met Phe Lys Asp Ile Gly Val Phe Lys Glu Thr Lys Gln Lys Arg Val
785                 790                 795                 800
Ser Val Leu Glu Leu Ser Ser Thr Phe Leu Pro Gln Cys Asn Arg Gln
                805                 810                 815
Lys Leu Leu Glu Tyr Ile Leu Ser Phe Val Val Leu
            820                 825

<210> SEQ ID NO 3
<211> LENGTH: 2484
<212> TYPE: DNA
<213> ORGANISM: Homo sapiens

<400> SEQUENCE: 3
```

| | | | | | |
|---|---|---|---|---|---|
| atggatgaat | ctgcactgac | ccttggtaca | atagatgttt | cttatctgcc | acattcatca | 60 |
| gaatacagtg | ttggtcgatg | taagcacaca | agtgaggaat | ggggtgagtg | tggctttaga | 120 |
| cccaccgtct | tcagatctgc | aactttaaaa | tggaaagaaa | gcctaatgag | tcggaaaagg | 180 |
| ccatttgttg | gaagatgttg | ttactcctgc | actccccaga | gctgggacaa | atttttcaac | 240 |
| cccagtatcc | cgtctttggg | tttgcggaat | gttatttata | tcaatgaaac | tcacacaaga | 300 |
| caccgcggat | ggcttgcaag | acgcctttct | tacgttcttt | ttattcaaga | gcgagatgtg | 360 |
| cataagggca | tgtttgccac | caatgtgact | gaaaatgtgc | tgaacagcag | tagagtacaa | 420 |
| gaggcaattg | cagaagtggc | tgctgaatta | accctgatg | ttctgccca | gcagcaatca | 480 |
| aaagccgtta | acaaagtgaa | aaagaaagct | aaaaggattc | ttcaagaaat | ggttgccact | 540 |
| gtctcaccgg | caatgatcag | actgactggg | tgggtgctgc | taaaactgtt | caacagcttc | 600 |
| ttttggaaca | ttcaaattca | caaaggtcaa | cttgagatgg | ttaaagctgc | aactgagacg | 660 |
| aatttgccgc | ttctgtttct | accagttcat | agatcccata | ttgactatct | gctgctcact | 720 |
| ttcattctct | tctgccataa | catcaaagca | ccatacattg | cttcaggcaa | taatctcaac | 780 |
| atcccaatct | tcagtaccct | tgatccataag | cttgggggct | tcttcatacg | acgaaggctc | 840 |
| gatgaaacac | cagatggacg | gaaagatgtt | ctctatagag | ctttgctcca | tgggcatata | 900 |
| gttgaattac | ttcgacagca | gcaattcttg | gagatcttcc | tggaaggcac | acgttctagg | 960 |
| agtggaaaaa | cctcttgtgc | tcgggcagga | ctttttgtcag | ttgtggtaga | tactctgtct | 1020 |
| accaatgtca | tcccagacat | cttgataata | cctgttggaa | tctccatatga | tcgcattatc | 1080 |

```
gaaggtcact acaatggtga acaactgggc aaacctaaga agaatgagag cctgtggagt    1140
gtagcaagag gtgttattag aatgttacga aaaaactatg gttgtgtccg agtggatttt    1200
gcacagccat tttccttaaa ggaatattta gaaagccaaa gtcagaaacc ggtgtctgct    1260
ctactttccc tggagcaagc gttgttacca gctatacttc cttcaagacc cagtgatgct    1320
gctgatgaag gtagagacac gtccattaat gagtccagaa atgcaacaga tgaatcccta    1380
cgaaggaggt tgattgcaaa tctggctgag catattctat tcactgctag caagtcctgt    1440
gccattatgt ccacacacat gtgtggcttgc ctgctcctct acagacacag gcagggaatt    1500
gatctctcca cattggtcga agacttcttt gtgatgaaag aggaagtcct ggctcgtgat    1560
tttgacctgg ggttctcagg aaattcagaa gatgtagtaa tgcatgccat acagctgctg    1620
ggaaattgtg tcacaatcac ccacactagc aggaacgatg agttttttat cacccccagc    1680
acaactgtcc catcagtctt cgaactcaac ttctacagca atggggtact tcatgtcttt    1740
atcatggagg ccatcatagc ttgcagcctt tatgcagttc tgaacaagag gggactgggg    1800
ggtcccacta gcaccccacc taacctgatc agccaggagc agctggtgcg aaggcggcc    1860 agcctgtgct accttctctc caatgaaggc accatctcac tgccttgcca gacattttac    1920
caagtctgcc atgaaacagt aggaaagttt atccagtatg gcattcttac agtggcagag    1980
cacgatgacc aggaagatat cagtcctagt cttgctgagc agcagtggga caagaagctt    2040 ccagaaccc tgtcttggag aagtgatgaa gaagatgaag acagtgactt tggggaggaa    2100
cagcgagatt gctacctgaa ggtgagccaa tccaaggagc accagcagtt tatcaccttc    2160
ttacagagac tccttgggcc tttgctggag gcctacagct ctgctgccat ctttgttcac    2220
aacttcagtg gtcctgttcc agaacctgag tatctgcaaa agttgcacaa atacctaata    2280
accagaacag aaagaaatgt tgcagtatat gctgagagtg ccacatattg tcttgtgaag    2340
aatgctgtga aaatgtttaa ggatattggg gttttcaagg agaccaaaca aaagagagtg    2400
tctgttttag aactgagcag cacttttcta cctcaatgca accgacaaaa acttctagaa    2460
tatattctga gttttgtggt gctg                                           2484
```

<210> SEQ ID NO 4
<211> LENGTH: 18
<212> TYPE: PRT
<213> ORGANISM: Artificial Sequence
<220> FEATURE:
<223> OTHER INFORMATION: HMM database acyltransferase domain

<400> SEQUENCE: 4

Asn His Ser Asp Pro Gly Arg Phe Pro Glu Gly Thr Arg Lys Gly Ala
 1               5                  10                  15

Pro Leu

<210> SEQ ID NO 5
<211> LENGTH: 179
<212> TYPE: PRT
<213> ORGANISM: Artificial Sequence
<220> FEATURE:
<223> OTHER INFORMATION: Prodom database acyltransferase protein

<400> SEQUENCE: 5

Phe Ile Gln Tyr Gly Ile Leu Thr Val Ala Glu Gln Asp Asp Gln Glu
 1               5                  10                  15

Asp Val Ser Pro Gly Leu Ala Glu Gln Gln Trp Asn Lys Lys Leu Pro
            20                  25                  30

```
Glu Pro Leu Asn Trp Arg Ser Asp Glu Glu Asp Glu Asp Ser Asp Phe
            35                  40                  45

Gly Glu Glu Gln Arg Asp Cys Tyr Leu Lys Val Ser Gln Ala Lys Glu
 50                  55                  60

His Gln Gln Phe Ile Thr Phe Leu Gln Arg Leu Leu Gly Pro Leu Leu
 65                  70                  75                  80

Glu Ala Tyr Ser Ser Ala Ala Ile Phe Val His Asn Phe Arg Gly Pro
                 85                  90                  95

Val Pro Glu Ser Glu Tyr Leu Gln Lys Leu His Arg Tyr Leu Ile Thr
                100                 105                 110

Arg Thr Glu Arg Asn Val Ala Val Tyr Ala Glu Ser Ala Thr Tyr Cys
                115                 120                 125

Leu Val Lys Asn Ala Val Lys Met Phe Lys Asp Ile Gly Val Phe Lys
130                 135                 140

Glu Thr Lys Gln Lys Arg Ala Ser Val Leu Glu Leu Ser Thr Thr Phe
145                 150                 155                 160

Leu Pro Gln Cys Asn Arg Gln Lys Leu Leu Glu Tyr Ile Leu Ser Phe
                165                 170                 175

Val Val Leu

<210> SEQ ID NO 6
<211> LENGTH: 97
<212> TYPE: PRT
<213> ORGANISM: Artificial Sequence
<220> FEATURE:
<223> OTHER INFORMATION: Prodom database acyltransferase protein

<400> SEQUENCE: 6

Met Ser Arg Lys Arg Pro Phe Val Gly Arg Cys Cys Tyr Ser Cys Thr
 1               5                  10                  15

Pro Gln Ser Trp Glu Arg Phe Phe Asn Pro Ser Ile Pro Ser Leu Gly
                20                  25                  30

Leu Arg Asn Val Ile Tyr Ile Asn Glu Thr His Thr Arg His Arg Gly
            35                  40                  45

Trp Leu Ala Arg Arg Leu Ser Tyr Ile Leu Phe Val Gln Glu Arg Asp
 50                  55                  60

Val His Lys Gly Met Phe Ala Thr Ser Ile Thr Asp Asn Val Leu Asn
 65                  70                  75                  80

Ser Ser Arg Val Gln Glu Ala Ile Ala Glu Val Ala Ala Glu Leu Asn
                 85                  90                  95

Pro

<210> SEQ ID NO 7
<211> LENGTH: 192
<212> TYPE: PRT
<213> ORGANISM: Artificial Sequence
<220> FEATURE:
<223> OTHER INFORMATION: Prodom database acyltransferase protein

<400> SEQUENCE: 7

Arg Asn Leu Ile Arg Ser Ile Gly Glu His Val Val Phe Asp Cys Ser
 1               5                  10                  15

Met Met Cys Ser Ile Met Ser Thr His Val Val Ala Cys Leu Leu Leu
                20                  25                  30

Thr Arg Trp Arg Asn Gly Val His Arg Ser Thr Leu Glu Glu Asp Cys
            35                  40                  45

Asp Trp Leu Cys Glu Lys Ile Leu Ala Glu Gly Gly Asp Ile Val Gly
```

```
                    50                  55                  60
Phe Ser Gly Lys Ser Thr Lys Gly Ser Gln Ile Val Lys Tyr Ala Cys
 65                  70                  75                  80

Glu Leu Leu Gly Ser Cys Val Thr Val Thr Asp Glu Asp Arg Asn Asp
                 85                  90                  95

Glu Phe Tyr Ile Ser Pro Lys Asn Ser Val Pro Ser Phe Ile Glu Leu
            100                 105                 110

Ala Tyr Tyr Ser Asn Ser Val Ile Cys His Phe Ala Leu Lys Ser Ile
            115                 120                 125

Ile Ala Cys Thr Ile Tyr Ser Leu Pro Asn Lys Thr Lys Asn Gly Gly
        130                 135                 140

Glu Ala Gly Gly Leu Gly Asn Leu Ile Ser Gln Glu Gln Leu Val Glu
145                 150                 155                 160

Asp Ala Leu Ser Leu Cys Asp Trp Leu Gln Tyr Glu Phe Met Phe Cys
                165                 170                 175

Arg Pro Cys Gln Thr Leu Arg Glu Leu Cys His Asn Thr Leu Gly Lys
            180                 185                 190

<210> SEQ ID NO 8
<211> LENGTH: 152
<212> TYPE: PRT
<213> ORGANISM: Artificial Sequence
<220> FEATURE:
<223> OTHER INFORMATION: Prodom database acyltransferase protein

<400> SEQUENCE: 8

Leu Ser Met Pro Ile Met Gly Ser Leu Leu Arg Arg Thr Gly Ala Phe
  1               5                  10                  15

Phe Ile Arg Arg Ser Phe Asp Pro Thr Pro Glu Gly Lys Gly Asp Gln
             20                  25                  30

Leu Tyr Arg Ala Val Phe His Glu Tyr Val Ala Gln Leu Ile Ser Lys
         35                  40                  45

Gly Tyr Asn Ile Glu Phe Phe Ile Glu Gly Thr Arg Ser Arg Thr Gly
     50                  55                  60

Lys Met Leu Pro Pro Lys Thr Gly Leu Leu Ser Met Val Val Glu Ala
 65                  70                  75                  80

Phe Leu Arg Gly Ser Val Pro Asp Ile Leu Leu Val Pro Val Ser Ile
                 85                  90                  95

Ser Tyr Asp Arg Ile Ile Glu Gly Asn Thr Tyr Ala His Glu Leu Arg
            100                 105                 110

Gly Ala Pro Lys Lys Lys Glu Ser Leu Trp Gln Leu Phe Arg Gly Val
        115                 120                 125

Arg Lys Met Leu Lys Arg Asn Tyr Gly Gln Val Tyr Val Asp Phe Gly
    130                 135                 140

Glu Pro Ile Ser Leu Arg Glu Tyr
145                 150

<210> SEQ ID NO 9
<211> LENGTH: 139
<212> TYPE: PRT
<213> ORGANISM: Artificial Sequence
<220> FEATURE:
<223> OTHER INFORMATION: Prodom database acyltransferase protein

<400> SEQUENCE: 9

Arg Asn Thr Tyr Asn Cys Ala Pro Lys Arg Leu Ala Leu Gln Lys Met
  1               5                  10                  15
```

```
Ser Phe Glu Val Ala Trp Arg Ile Leu Gln Ala Thr Pro Val Thr Ala
            20                  25                  30

Thr Gly Leu Val Ser Ala Leu Leu Thr Thr Arg Gly Thr Ala Leu
        35                  40                  45

Thr Leu Asp Gln Leu His His Thr Leu Gln Asp Ser Leu Asp Tyr Leu
    50                  55                  60

Glu Arg Lys Gln Ser Pro Val Ser Thr Ser Ala Leu Arg Leu Arg Ser
65                  70                  75                  80

Arg Glu Gly Val Arg Ala Ala Asp Ala Leu Ser Asn Gly His Pro
                85                  90                  95

Val Thr Arg Val Asp Ser Gly Arg Glu Pro Val Trp Tyr Ile Ala Pro
            100                 105                 110

Asp Asp Glu His Ala Ala Ala Phe Tyr Arg Asn Ser Val Ile His Ala
            115                 120                 125

Phe Leu Glu Thr Ser Ile Val Glu Leu Ala Leu
            130                 135
```

<210> SEQ ID NO 10
<211> LENGTH: 123
<212> TYPE: PRT
<213> ORGANISM: Artificial Sequence
<220> FEATURE:
<223> OTHER INFORMATION: Prodom database acyltransferase protein

<400> SEQUENCE: 10

```
Asn Leu Lys Lys Asn Val Leu Asn Ser Glu Glu Ile His Tyr Val Ile
1               5                   10                  15

Glu Gln Glu Ala Lys Glu Ser Ser Thr Ser Ile Asp Lys Val Arg Arg
            20                  25                  30

Glu Ala Arg Glu Ile Leu Asp Glu Met Ser His Thr Leu Asn Met Gly
        35                  40                  45

Met Ile Arg Phe Cys Gly Trp Val Leu Ser Lys Ile Phe Asn Arg Ile
    50                  55                  60

Phe Ser Gly Ile Cys Val Asn Glu Gln Ile Glu Lys Ile Lys Arg
65                  70                  75                  80

Ala Thr Glu Gln Gly His Pro Val Ile Tyr Leu Pro Ser His Arg Ser
                85                  90                  95

His Ile Asp Tyr Leu Leu Leu Ser Phe Ile Leu Tyr His Tyr Asp Ile
            100                 105                 110

Lys Val Pro His Ile Ala Ala Gly Met Asn Leu
            115                 120
```

<210> SEQ ID NO 11
<211> LENGTH: 55
<212> TYPE: PRT
<213> ORGANISM: Artificial Sequence
<220> FEATURE:
<223> OTHER INFORMATION: Prodom database acyltransferase protein

<400> SEQUENCE: 11

```
Met Glu Glu Ser Ser Val Thr Ile Gly Thr Ile Asp Val Ser Tyr Leu
1               5                   10                  15

Pro Asn Ser Ser Glu Tyr Ser Leu Gly Arg Cys Lys His Thr Asn Glu
            20                  25                  30

Asp Trp Val Asp Cys Gly Phe Lys Pro Thr Phe Phe Arg Ser Ala Thr
        35                  40                  45

Leu Lys Trp Lys Glu Ser Leu
    50                  55
```

<210> SEQ ID NO 12
<211> LENGTH: 123
<212> TYPE: PRT
<213> ORGANISM: Artificial Sequence
<220> FEATURE:
<223> OTHER INFORMATION: Prodom database acyltransferase protein

<400> SEQUENCE: 12

```
Val Asn His Leu Ala Lys Gln Ile Met Thr His Ile Asn Asp Ala Ala
  1               5                  10                  15

Ala Val Asn Pro Met Asn Leu Cys Ala Thr Ala Leu Leu Ser Thr Arg
             20                  25                  30

Gln Arg Ala Leu Gly Glu Glu Gln Leu Ile Glu Gln Leu Asp Cys Tyr
         35                  40                  45

Leu Lys Leu Leu Arg Asn Val Pro Tyr Ser Thr Asp Ala Thr Leu Pro
     50                  55                  60

Asp His Thr Pro Glu Arg Leu Ile Glu His Ala Glu Gln Met Asn Leu
 65                  70                  75                  80

Leu Gly Val Thr Val Glu Lys Asp Thr Leu Gly Asp Ile Leu Arg Leu
                 85                  90                  95

Asp Arg Asp Asn Ala Val Leu Met Thr Tyr Tyr Arg Asn Asn Val Leu
            100                 105                 110

His Leu Phe Ala Leu Pro Ala Leu Val Ala Cys
        115                 120
```

<210> SEQ ID NO 13
<211> LENGTH: 91
<212> TYPE: PRT
<213> ORGANISM: Artificial Sequence
<220> FEATURE:
<223> OTHER INFORMATION: Prodom database acyltransferase protein

<400> SEQUENCE: 13

```
Met Thr Tyr Tyr Arg Asn Asn Val Leu His Leu Phe Ala Leu Pro Ala
  1               5                  10                  15

Leu Val Ala Cys Cys Phe Lys Asn Asn Arg Arg Ile Ser Arg Asp Ala
             20                  25                  30

Leu Leu Arg Phe Val Arg Ala Leu Tyr Pro Phe Leu Gln Ala Glu Leu
         35                  40                  45

Phe Leu Arg Trp Asn Glu Asp Glu Leu Asn Asp His Ile Asp Gln Trp
     50                  55                  60

Ile Asn Glu Phe Val Arg Gln Gly Leu Leu Leu Ser Ala Gly Asn Gln
 65                  70                  75                  80

Glu Asp Asp Thr Leu Thr Arg Asn Thr Ser Gln
                 85                  90
```

<210> SEQ ID NO 14
<211> LENGTH: 110
<212> TYPE: PRT
<213> ORGANISM: Artificial Sequence
<220> FEATURE:
<223> OTHER INFORMATION: Prodom database acyltransferase protein

<400> SEQUENCE: 14

```
Trp Asn Glu Ser Glu Val Leu Val Asp Arg Lys Ser Lys Phe Gln Ala
  1               5                  10                  15

Arg Cys Cys Pro Leu Gln Asn Gln Lys Asp Ile Pro Ser Ile Leu Gln
             20                  25                  30
```

```
Glu Leu Thr Gln Asn Asn Lys Ser Val Ser Lys Ala Ser His Met His
            35                  40                  45

Met Tyr Ala Trp Arg Thr Ala Glu Val Ser Asn Asn Leu His Leu Gln
 50                  55                  60

Gln Glu Gln Lys Lys Gly Asn Lys Ala Asn Lys Ser Asn Asn Ser
 65                  70                  75                  80

His Val Asn Lys Ser Arg Asn Ile Thr Val Gln Pro Lys Asn Ile Glu
            85                  90                  95

Gln Gly Cys Ala Asp Cys Gly Glu Ala Gly Ala Gly Gln Arg
            100                 105                 110

<210> SEQ ID NO 15
<211> LENGTH: 827
<212> TYPE: PRT
<213> ORGANISM: Mus musculus
<220> FEATURE:
<223> OTHER INFORMATION: Prodom database acyltransferase protein

<400> SEQUENCE: 15

Met Glu Glu Ser Ser Val Thr Val Gly Thr Ile Asp Val Ser Tyr Leu
 1               5                  10                  15

Pro Ser Ser Glu Tyr Ser Leu Gly Arg Cys Lys His Thr Ser Glu
                20                  25                  30

Asp Trp Val Asp Cys Gly Phe Lys Pro Thr Phe Phe Arg Ser Ala Thr
            35                  40                  45

Leu Lys Trp Lys Glu Ser Leu Met Ser Arg Lys Arg Pro Phe Val Gly
 50                  55                  60

Arg Cys Cys Tyr Ser Cys Thr Pro Gln Ser Trp Glu Arg Phe Phe Asn
 65                  70                  75                  80

Pro Ser Ile Pro Ser Leu Gly Leu Arg Asn Val Ile Tyr Ile Asn Glu
            85                  90                  95

Thr His Thr Arg His Arg Gly Trp Leu Ala Arg Arg Leu Ser Tyr Ile
            100                 105                 110

Leu Phe Val Gln Glu Arg Asp Val His Lys Gly Met Phe Ala Thr Ser
        115                 120                 125

Val Thr Glu Asn Val Leu Ser Ser Arg Val Gln Glu Ala Ile Ala
        130                 135                 140

Glu Val Ala Ala Glu Leu Asn Pro Asp Gly Ser Ala Gln Gln Ser
145                 150                 155                 160

Lys Ala Ile Gln Lys Val Lys Arg Lys Ala Arg Lys Ile Leu Gln Glu
                165                 170                 175

Met Val Ala Thr Val Ser Pro Gly Met Ile Arg Leu Thr Gly Trp Val
            180                 185                 190

Leu Leu Lys Leu Phe Asn Ser Phe Trp Asn Ile Gln Ile His Lys
        195                 200                 205

Gly Gln Leu Glu Met Val Lys Ala Thr Glu Thr Asn Leu Pro Leu
        210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Val Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285
```

-continued

```
Asp Ile Leu Tyr Arg Ala Leu Leu His Gly His Val Glu Leu Leu
    290                 295                 300
Arg Gln Gln Gln Phe Leu Glu Ile Phe Leu Glu Gly Thr Arg Ser Arg
305                 310                 315                 320
Ser Gly Lys Thr Ser Cys Ala Arg Ala Gly Val Leu Ser Val Val Val
                325                 330                 335
Asn Thr Leu Ser Ser Asn Thr Ile Pro Asp Ile Leu Val Ile Pro Val
                340                 345                 350
Gly Ile Ser Tyr Asp Arg Ile Ile Glu Gly His Tyr Asn Gly Glu Gln
                355                 360                 365
Leu Gly Lys Pro Lys Asn Glu Ser Leu Trp Ser Val Ala Arg Gly
370                 375                 380
Val Ile Arg Met Leu Arg Lys Asn Tyr Gly Tyr Val Arg Val Asp Phe
385                 390                 395                 400
Ala Gln Pro Phe Ser Leu Lys Glu Tyr Leu Glu Gly Gln Ser Gln Lys
                405                 410                 415
Pro Val Ser Ala Pro Leu Ser Leu Glu Gln Ala Leu Leu Pro Ala Ile
                420                 425                 430
Leu Pro Ser Arg Pro Asn Asp Val Ala Asp Glu His Gln Asp Leu Ser
                435                 440                 445
Ile Asn Glu Ser Arg Asn Pro Ala Asp Glu Ala Phe Arg Arg Arg Leu
450                 455                 460
Ile Ala Asn Leu Ala Glu His Ile Leu Phe Thr Ala Ser Lys Ser Cys
465                 470                 475                 480
Ala Ile Met Ser Thr His Ile Val Ala Cys Leu Leu Tyr Arg His
                485                 490                 495
Arg Gln Gly Ile His Leu Ser Thr Leu Val Glu Asp Phe Phe Val Met
                500                 505                 510
Lys Glu Glu Val Leu Ala Arg Asp Phe Asp Leu Gly Phe Ser Gly Asn
                515                 520                 525
Ser Glu Asp Val Val Met His Ala Ile Gln Leu Leu Gly Asn Cys Val
                530                 535                 540
Thr Ile Thr His Thr Ser Arg Lys Asp Glu Phe Phe Ile Thr Pro Ser
545                 550                 555                 560
Thr Thr Val Pro Ser Val Phe Glu Leu Asn Phe Tyr Ser Asn Gly Val
                565                 570                 575
Leu His Val Phe Ile Met Glu Ala Ile Ala Cys Ser Leu Tyr Ala
                580                 585                 590
Val Leu Asn Lys Arg Cys Ser Gly Gly Pro Thr Ser Thr Pro Pro Asn
                595                 600                 605
Leu Ile Ser Gln Glu Gln Leu Val Arg Lys Ala Ala Ser Leu Cys Tyr
                610                 615                 620
Leu Leu Ser Asn Glu Gly Thr Ile Ser Leu Pro Cys Gln Thr Phe Tyr
625                 630                 635                 640
Gln Val Cys His Glu Thr Val Gly Lys Phe Ile Gln Tyr Gly Ile Leu
                645                 650                 655
Thr Val Ala Glu Gln Asp Gln Glu Asp Val Ser Pro Gly Leu Ala
                660                 665                 670
Glu Gln Gln Trp Asp Lys Lys Leu Pro Glu Leu Asn Trp Arg Ser Asp
                675                 680                 685
Glu Glu Asp Glu Asp Ser Asp Phe Gly Glu Glu Gln Arg Asp Cys Tyr
690                 695                 700
Leu Lys Val Ser Gln Ser Lys Glu His Gln Gln Phe Ile Thr Phe Leu
```

```
                705                 710                 715                 720
Gln Arg Leu Leu Gly Pro Leu Leu Glu Ala Tyr Ser Ala Ala Ile
                    725                 730                 735

Phe Val His Asn Phe Ser Gly Pro Val Pro Glu Pro Glu Tyr Leu Gln
                    740                 745                 750

Arg Leu His Lys Tyr Leu Ile Thr Arg Thr Glu Arg Asn Val Ala Val
                    755                 760                 765

Tyr Ala Glu Ser Ala Thr Tyr Cys Leu Val Lys Asn Ala Val Lys Met
                    770                 775                 780

Phe Lys Asp Ile Gly Val Phe Lys Glu Thr Lys Gln Lys Arg Val Ser
785                 790                 795                 800

Val Leu Glu Leu Ser Ser Thr Phe Leu Pro Gln Cys Asn Arg Gln Lys
                    805                 810                 815

Leu Leu Glu Tyr Ile Leu Ser Phe Val Val Leu
                    820                 825

<210> SEQ ID NO 16
<211> LENGTH: 828
<212> TYPE: PRT
<213> ORGANISM: Rattus norvegicus

<400> SEQUENCE: 16

Met Glu Glu Ser Ser Val Thr Ile Gly Thr Ile Asp Val Ser Tyr Leu
1               5                   10                  15

Pro Asn Ser Ser Glu Tyr Ser Leu Gly Arg Cys Lys His Thr Asn Glu
                20                  25                  30

Asp Trp Val Asp Cys Gly Phe Lys Pro Thr Phe Phe Arg Ser Ala Thr
            35                  40                  45

Leu Lys Trp Lys Glu Ser Leu Met Ser Arg Lys Arg Pro Phe Val Gly
        50                  55                  60

Arg Cys Cys Tyr Ser Cys Thr Pro Gln Ser Trp Glu Arg Phe Phe Asn
65                  70                  75                  80

Pro Ser Ile Pro Ser Leu Gly Leu Arg Asn Val Ile Tyr Ile Asn Glu
                85                  90                  95

Thr His Thr Arg His Arg Gly Trp Leu Ala Arg Arg Leu Ser Tyr Ile
                100                 105                 110

Leu Phe Val Gln Glu Arg Asp Val His Lys Gly Met Phe Ala Thr Ser
                115                 120                 125

Ile Thr Asp Asn Val Leu Asn Ser Ser Arg Val Gln Glu Ala Ile Ala
            130                 135                 140

Glu Val Ala Ala Glu Leu Asn Pro Asp Gly Ser Ala Gln Gln Gln Ser
145                 150                 155                 160

Lys Ala Ile Gln Lys Val Lys Arg Lys Ala Arg Lys Ile Leu Gln Glu
                165                 170                 175

Met Val Ala Thr Val Ser Pro Gly Met Ile Arg Leu Thr Gly Trp Val
                180                 185                 190

Leu Leu Lys Leu Phe Asn Ser Phe Phe Trp Asn Ile Gln Ile His Lys
                195                 200                 205

Gly Gln Leu Glu Met Val Lys Ala Ala Thr Glu Thr Asn Leu Pro Leu
            210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255
```

-continued

```
Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Ile Leu Tyr Arg Ala Leu Leu His Gly His Ile Val Glu Leu Leu
        290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Ser Asn Thr Ile Pro Asp Ile Leu Val Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Tyr Val Arg Val Asp Phe
385                 390                 395                 400

Ala Gln Pro Phe Ser Leu Lys Glu Tyr Leu Glu Gly Gln Ser Gln Lys
                405                 410                 415

Pro Val Ser Ala Pro Leu Ser Leu Glu Gln Ala Leu Leu Pro Ala Ile
            420                 425                 430

Leu Pro Ser Arg Pro Asp Ala Ala Ala Glu His Glu Asp Met Ser
        435                 440                 445

Ile Asn Glu Ser Arg Asn Ala Ala Asp Glu Ala Phe Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile His Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540

Thr Ile Thr His Thr Ser Arg Lys Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Gln Asn Lys Arg Gly Ser Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys Gln Glu Thr Val Gly Lys Phe Ile Gln Tyr Gly Ile Leu
                645                 650                 655

Thr Val Ala Glu Gln Asp Asp Gln Glu Asp Val Ser Pro Gly Leu Ala
            660                 665                 670

Glu Gln Gln Trp Asn Lys Lys Leu Pro Glu Pro Leu Asn Trp Arg Ser
```

-continued

```
            675                 680                 685
Asp Glu Glu Asp Glu Asp Ser Asp Phe Gly Glu Gln Arg Asp Cys
    690                 695                 700

Tyr Leu Lys Val Ser Gln Ala Lys Glu His Gln Gln Phe Ile Thr Phe
705                 710                 715                 720

Leu Gln Arg Leu Leu Gly Pro Leu Leu Glu Ala Tyr Ser Ser Ala Ala
                725                 730                 735

Ile Phe Val His Thr Phe Arg Gly Pro Val Pro Glu Pro Glu Tyr Leu
            740                 745                 750

Gln Arg Leu His Lys Tyr Leu Ile Thr Arg Thr Glu Arg Asn Val Ala
        755                 760                 765

Val Tyr Ala Glu Ser Ala Thr Tyr Cys Leu Val Lys Asn Ala Val Lys
    770                 775                 780

Met Phe Lys Asp Ile Gly Val Phe Lys Glu Thr Lys Gln Lys Arg Ala
785                 790                 795                 800

Ser Val Leu Glu Leu Ser Ser Thr Phe Leu Pro Gln Cys Asn Arg Gln
                805                 810                 815

Lys Leu Leu Glu Tyr Ile Leu Ser Phe Val Val Leu
            820                 825
```